US011587673B2

(12) United States Patent
Pillai et al.

(10) Patent No.: US 11,587,673 B2
(45) Date of Patent: *Feb. 21, 2023

(54) SYSTEMS, METHODS AND ARTICLES FOR ENHANCING WELLNESS ASSOCIATED WITH HABITABLE ENVIRONMENTS

(71) Applicant: Delos Living LLC, New York, NY (US)

(72) Inventors: Dana S. Pillai, New York, NY (US); Nathan B. Stodola, New York, NY (US); Renato P. Termale, New York, NY (US); Richard A. Macary, New York, NY (US)

(73) Assignee: Delos Living LLC, New York, NY (US)

( * ) Notice: Subject to any disclaimer, the term of this patent is extended or adjusted under 35 U.S.C. 154(b) by 255 days.

This patent is subject to a terminal disclaimer.

(21) Appl. No.: 17/060,975

(22) Filed: Oct. 1, 2020

(65) Prior Publication Data

US 2021/0035686 A1  Feb. 4, 2021

Related U.S. Application Data

(63) Continuation of application No. 16/444,877, filed on Jun. 18, 2019, now Pat. No. 10,928,842, and a
(Continued)

(51) Int. Cl.
*G16H 40/67* (2018.01)
*G05D 27/02* (2006.01)
(Continued)

(52) U.S. Cl.
CPC ............... *G16H 40/67* (2018.01); *A61L 2/00* (2013.01); *A61L 9/00* (2013.01); *A61L 9/20* (2013.01);
(Continued)

(58) Field of Classification Search
CPC .......... G16H 40/67; G16H 40/20; A61L 2/00; A61L 9/00; A61L 9/20; A61L 2209/11;
(Continued)

(56) References Cited

U.S. PATENT DOCUMENTS

| 628,351 A | 7/1899 | Gibson |
| 828,733 A | 8/1906 | Fuller |

(Continued)

FOREIGN PATENT DOCUMENTS

| CA | 2307458 | 11/2001 |
| CA | 2740939 | 3/2010 |

(Continued)

OTHER PUBLICATIONS

Communication pursuant to Article 94(3) EPC issued in EP Application No. 20191237.5 dated Jun. 14, 2021 (13 pages).
(Continued)

*Primary Examiner* — Mohammad Ali
*Assistant Examiner* — Sheela Rao
(74) *Attorney, Agent, or Firm* — Fitch, Even, Tabin & Flannery LLP

(57) ABSTRACT

Environmental characteristics of habitable environments (e.g., hotel or motel rooms, spas, resorts, cruise boat cabins, offices, hospitals and/or homes, apartments or residences) are controlled to eliminate, reduce or ameliorate adverse or harmful aspects and introduce, increase or enhance beneficial aspects in order to improve a "wellness" or sense of "wellbeing" provided via the environments. Control of intensity and wavelength distribution of passive and active Illumination addresses various issues, symptoms or syndromes, for instance to maintain a circadian rhythm or cycle, adjust for "jet lag" or season affective disorder, etc. Air quality and attributes are controlled. Scent(s) may be dispersed. Hypoallergenic items (e.g., bedding, linens) may be
(Continued)

FIG. 1 used. Water quality is controlled. Noise is reduced and sounds (e.g., masking, music, natural) may be provided. Passive and active pathogen controls are employed. Controls are provided for the occupant and/or facility personnel, as is instruction, and surveys, including assessing wellness.

22 Claims, 7 Drawing Sheets

Related U.S. Application Data continuation of application No. 15/421,022, filed on Jan. 31, 2017, now Pat. No. 10,845,829, said application No. 16/444,877 is a continuation of application No. 15/421,022, filed on Jan. 31, 2017, now Pat. No. 10,845,829, and a continuation of application No. 15/409,233, filed on Jan. 18, 2017, now Pat. No. 10,691,148, which is a continuation of application No. 14/012,444, filed on Aug. 28, 2013, now Pat. No. 9,715,242, said application No. 15/421,022 is a continuation of application No. 14/012,444, filed on Aug. 28, 2013, now Pat. No. 9,715,242.

(60) Provisional application No. 61/694,125, filed on Aug. 28, 2012.

(51) Int. Cl.

| | |
|---|---|
| G16H 40/20 | (2018.01) |
| F24F 11/30 | (2018.01) |
| H04L 12/28 | (2006.01) |
| G05B 15/02 | (2006.01) |
| A61M 21/00 | (2006.01) |
| F24F 3/12 | (2006.01) |
| F24F 11/00 | (2018.01) |
| H05B 47/10 | (2020.01) |
| H05B 47/175 | (2020.01) |
| H05B 47/115 | (2020.01) |
| F24F 11/523 | (2018.01) |
| F24F 11/64 | (2018.01) |
| A61M 21/02 | (2006.01) |
| A61L 9/00 | (2006.01) |
| A61L 2/00 | (2006.01) |
| B60H 3/00 | (2006.01) |
| A61L 9/20 | (2006.01) |
| G05B 19/048 | (2006.01) |
| G06F 3/16 | (2006.01) |
| F24F 120/10 | (2018.01) |
| F24F 120/14 | (2018.01) |
| B05B 1/18 | (2006.01) |
| E03C 1/046 | (2006.01) |
| A61N 5/06 | (2006.01) |
| F24F 8/50 | (2021.01) |

(52) U.S. Cl.
CPC ........ *A61M 21/0094* (2013.01); *A61M 21/02* (2013.01); *B60H 3/0007* (2013.01); *F24F 3/12* (2013.01); *F24F 11/0008* (2013.01); *F24F 11/30* (2018.01); *F24F 11/523* (2018.01); *F24F 11/64* (2018.01); *G05B 15/02* (2013.01); *G05B 19/048* (2013.01); *G05D 27/02* (2013.01); *G06F 3/165* (2013.01); *G16H 40/20* (2018.01); *H04L 12/2816* (2013.01); *H04L 12/2827* (2013.01); *H04L 12/2829* (2013.01); *H05B 47/10* (2020.01); *H05B 47/115* (2020.01); *H05B 47/175* (2020.01); *A61L 2209/11* (2013.01); *A61M 2021/0011* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2021/0083* (2013.01); *A61M 2205/0205* (2013.01); *A61M 2205/0238* (2013.01); *A61M 2205/13* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/42* (2013.01); *A61M 2205/50* (2013.01); *A61M 2205/505* (2013.01); *A61M 2205/52* (2013.01); *A61M 2205/6018* (2013.01); *A61M 2205/6054* (2013.01); *A61M 2205/6063* (2013.01); *A61M 2205/7509* (2013.01); *A61M 2205/7518* (2013.01); *A61M 2205/7545* (2013.01); *A61M 2230/005* (2013.01); *A61M 2230/04* (2013.01); *A61M 2230/50* (2013.01); *A61M 2230/63* (2013.01); *A61N 5/0618* (2013.01); *B05B 1/18* (2013.01); *E03C 1/046* (2013.01); *F24F 8/50* (2021.01); *F24F 2120/10* (2018.01); *F24F 2120/14* (2018.01); *G05B 2219/2642* (2013.01); *Y02A 90/10* (2018.01)

(58) Field of Classification Search
CPC .............. A61M 21/0094; A61M 21/02; A61M 2021/0011; A61M 2021/0016; A61M 2021/0022; A61M 2021/0027; A61M 2021/0044; A61M 2021/0066; A61M 2021/0083; A61M 2205/0205; A61M 2205/0238; A61M 2205/13; A61M 2205/3368; A61M 2205/3553; A61M 2205/3561; A61M 2205/3584; A61M 2205/3592; A61M 2205/42; A61M 2205/50; A61M 2205/505; A61M 2205/52; A61M 2205/6018; A61M 2205/6054; A61M 2205/6063; A61M 2205/7509; A61M 2205/7518; A61M 2205/7545; A61M 2230/005; A61M 2230/04; A61M 2230/50; A61M 2230/63; B60H 3/0007; F24F 3/12; F24F 11/0008; F24F 11/30; F24F 8/50; F24F 2120/10; F24F 2120/14; G05B 15/02; G05B 19/048; G05B 2219/2642; G05B 19/054; G05B 2219/1103; G05D 27/02; G06F 3/165; H04L 12/2816; H04L 12/2827; H04L 12/2829; H05B 47/10; H05B 47/115; H05B 47/175; H05B 47/11; H05B 47/105; A61N 5/0618; B05B 1/18; E03C 1/046; Y02A 90/10; G06Q 30/0203; Y02B 20/40

See application file for complete search history.

(56) References Cited

U.S. PATENT DOCUMENTS

| | | |
|---|---|---|
| 853,033 A | 5/1907 | Roberts |
| 1,648,277 A | 11/1927 | Korb |
| 1,856,969 A | 5/1932 | Reiter |
| 2,184,644 A | 12/1939 | Homberger |
| 3,483,302 A | 12/1969 | Ashkenas |
| RE27,027 E | 1/1971 | Cristofv |
| 3,621,838 A | 11/1971 | Harding |
| 3,678,337 A | 7/1972 | Grauvogel |
| 3,782,006 A | 1/1974 | Symmes |
| 3,901,215 A | 8/1975 | John |
| 3,910,701 A | 10/1975 | Henderson |

(56) References Cited

U.S. PATENT DOCUMENTS

| | | |
|---|---|---|
| 4,074,124 A | 2/1978 | Maute |
| 4,122,334 A | 10/1978 | Owens |
| 4,135,116 A | 1/1979 | Smith |
| 4,233,545 A | 11/1980 | Webster |
| 4,236,101 A | 11/1980 | Luchaco |
| 4,247,766 A | 1/1981 | Warren |
| 4,273,999 A | 6/1981 | Pierpoint |
| 4,308,911 A | 1/1982 | Mandl |
| 4,587,459 A | 5/1986 | Blake |
| 4,638,853 A | 1/1987 | Papak |
| 4,701,669 A | 10/1987 | Head |
| 4,717,343 A | 1/1988 | Densky |
| D295,934 S | 5/1988 | Dyrhood |
| 4,755,140 A | 7/1988 | Rimland |
| 4,770,636 A | 9/1988 | Buschke |
| 4,803,625 A | 2/1989 | Fu |
| 4,828,609 A | 5/1989 | Anderson |
| 4,853,854 A | 8/1989 | Behar |
| 4,858,609 A | 8/1989 | Cole |
| 4,882,166 A | 11/1989 | Graham |
| 4,893,291 A | 1/1990 | Bick |
| 4,911,166 A | 3/1990 | Leighton |
| 4,911,737 A | 3/1990 | Yehl |
| 4,916,642 A | 4/1990 | Kaiser |
| 4,930,505 A | 6/1990 | Hatje |
| 4,938,582 A | 7/1990 | Leslie |
| 4,947,928 A | 8/1990 | Parker |
| 4,953,784 A | 9/1990 | Yasufuku |
| 4,962,687 A | 10/1990 | Belliveau |
| D312,018 S | 11/1990 | Giesy |
| 5,006,985 A | 4/1991 | Ehret |
| 5,010,777 A * | 4/1991 | Yehl .................. B60H 3/00 361/231 |
| 5,017,142 A | 5/1991 | Bemis |
| 5,043,840 A | 8/1991 | Yehl |
| 5,079,682 A | 1/1992 | Roberts |
| 5,079,726 A | 1/1992 | Keller |
| 5,082,173 A | 1/1992 | Poehlman |
| 5,086,385 A | 2/1992 | Launey |
| 5,092,669 A | 3/1992 | Anderson |
| 5,103,391 A | 4/1992 | Barrett |
| 5,103,408 A | 4/1992 | Greenberg |
| 5,121,030 A | 6/1992 | Schott |
| 5,176,133 A | 1/1993 | Czeisler |
| 5,193,900 A | 3/1993 | Yano |
| 5,197,941 A | 3/1993 | Whitaker |
| 5,207,580 A | 5/1993 | Strecher |
| 5,214,736 A | 5/1993 | Uemiya |
| D335,978 S | 6/1993 | Grahn |
| 5,230,629 A | 7/1993 | Buschke |
| 5,250,799 A | 10/1993 | Werner |
| 5,259,553 A | 11/1993 | Shyu |
| 5,285,356 A | 2/1994 | Skene |
| 5,285,430 A | 2/1994 | Decker |
| D345,071 S | 3/1994 | Gould |
| 5,290,200 A | 3/1994 | Kiser |
| 5,292,345 A | 3/1994 | Gerardo |
| 5,295,491 A | 3/1994 | Gevins |
| 5,304,212 A | 4/1994 | Czeisler |
| 5,343,121 A | 8/1994 | Terman |
| 5,344,068 A | 9/1994 | Haessig |
| 5,344,324 A | 9/1994 | O'Donnell |
| 5,350,977 A | 9/1994 | Hamamoto |
| 5,357,170 A | 10/1994 | Luchaco |
| 5,374,876 A | 12/1994 | Horibata |
| 5,377,258 A | 12/1994 | Bro |
| 5,395,042 A | 3/1995 | Riley |
| 5,433,923 A | 7/1995 | Wolverton |
| 5,436,535 A | 7/1995 | Yang |
| 5,462,485 A | 10/1995 | Kinkead |
| D364,762 S | 12/1995 | Compton |
| D365,484 S | 12/1995 | Trattner, Jr |
| 5,473,537 A | 12/1995 | Glazer |
| 5,503,637 A | 4/1996 | Kyricos |
| 5,545,192 A | 8/1996 | Czeisler |
| 5,589,741 A | 12/1996 | Terman |
| 5,596,994 A | 1/1997 | Bro |
| 5,648,656 A | 7/1997 | Begemann |
| 5,692,501 A | 12/1997 | Minturn |
| 5,721,471 A | 2/1998 | Begemann |
| 5,722,418 A | 3/1998 | Bro |
| 5,724,987 A | 3/1998 | Gevins |
| 5,742,516 A | 4/1998 | Olcerst |
| 5,749,365 A | 5/1998 | Magill |
| D396,581 S | 8/1998 | Schubert |
| 5,791,982 A | 8/1998 | Curry |
| 5,805,267 A | 9/1998 | Goldman |
| 5,813,863 A | 9/1998 | Sloane |
| D401,085 S | 11/1998 | Grant |
| 5,833,466 A | 11/1998 | Borg |
| 5,861,717 A | 1/1999 | Begemann |
| 5,892,690 A | 4/1999 | Boatman |
| 5,908,301 A | 6/1999 | Lutz |
| 5,911,581 A | 6/1999 | Reynolds |
| 5,919,217 A | 7/1999 | Hughes |
| 5,937,387 A | 8/1999 | Summerell |
| 5,954,510 A | 9/1999 | Merrill |
| 5,963,294 A | 10/1999 | Schiffer |
| 5,967,789 A | 10/1999 | Segel |
| 5,976,010 A | 11/1999 | Reese |
| 6,053,936 A | 4/2000 | Koyama |
| 6,055,480 A | 4/2000 | Nevo |
| D424,356 S | 5/2000 | Hahn |
| 6,118,230 A | 9/2000 | Fleischmann |
| 6,135,970 A | 10/2000 | Kadhiresan |
| 6,166,496 A | 12/2000 | Lys |
| 6,170,318 B1 | 1/2001 | Lewis |
| 6,197,094 B1 | 3/2001 | Thofelt |
| 6,208,905 B1 | 3/2001 | Giddings |
| 6,235,046 B1 | 5/2001 | Gerdt |
| 6,238,337 B1 | 5/2001 | Kambhatla |
| 6,269,339 B1 | 7/2001 | Silver |
| 6,280,198 B1 | 8/2001 | Calhoun |
| 6,290,140 B1 | 9/2001 | Pesko |
| 6,331,160 B1 | 12/2001 | Bardy |
| 6,340,864 B1 | 1/2002 | Wacyk |
| 6,340,868 B1 | 1/2002 | Lys |
| 6,344,641 B1 | 2/2002 | Blalock |
| 6,348,867 B1 | 2/2002 | Myllymaki |
| 6,350,275 B1 | 2/2002 | Vreman |
| 6,369,716 B1 | 4/2002 | Abbas |
| 6,387,844 B1 | 5/2002 | Fujishima |
| 6,411,046 B1 | 6/2002 | Muthu |
| 6,416,472 B1 | 7/2002 | Cady |
| 6,417,019 B1 | 7/2002 | Mueller |
| 6,419,629 B1 | 7/2002 | Balkin |
| 6,435,878 B1 | 8/2002 | Reynolds |
| 6,439,893 B1 | 8/2002 | Byrd |
| 6,441,558 B1 | 8/2002 | Muthu |
| 6,448,550 B1 | 9/2002 | Nishimura |
| 6,448,978 B1 | 9/2002 | Salvador |
| 6,459,919 B1 | 10/2002 | Lys |
| 6,488,698 B1 | 12/2002 | Hyman |
| 6,498,440 B2 | 12/2002 | Stam |
| 6,503,462 B1 | 1/2003 | Michalakos |
| 6,507,159 B2 | 1/2003 | Muthu |
| 6,507,709 B2 | 1/2003 | Hirai |
| 6,525,658 B2 | 2/2003 | Streetman |
| 6,535,190 B2 | 3/2003 | Evanicky |
| 6,553,252 B2 | 4/2003 | Balkin |
| 6,554,439 B1 | 4/2003 | Teicher |
| 6,565,359 B2 | 5/2003 | Calhoun |
| 6,567,009 B2 | 5/2003 | Ohishi |
| 6,582,380 B2 | 6/2003 | Kazlausky |
| 6,583,573 B2 | 6/2003 | Bierman |
| 6,583,720 B1 | 6/2003 | Quigley |
| D477,158 S | 7/2003 | Calcerano |
| 6,589,912 B2 | 7/2003 | Kawai |
| 6,607,484 B2 | 8/2003 | Suzuki |
| 6,608,453 B2 | 8/2003 | Morgan |
| 6,610,127 B2 | 8/2003 | Lu |
| 6,614,013 B2 | 9/2003 | Pitigoi-Aron |
| 6,618,723 B1 | 9/2003 | Smith |
| 6,623,512 B1 | 9/2003 | Heller |

(56) References Cited

U.S. PATENT DOCUMENTS

| | | |
|---|---|---|
| 6,632,174 B1 | 10/2003 | Breznitz |
| 6,661,798 B2 | 12/2003 | Sano |
| 6,666,567 B1 | 12/2003 | Feldman |
| 6,669,481 B2 | 12/2003 | Winter |
| 6,683,419 B2 | 1/2004 | Kriparos |
| 6,691,070 B1 | 2/2004 | Williams |
| 6,711,470 B1 | 3/2004 | Hartenstein |
| 6,712,615 B2 | 3/2004 | Martin |
| 6,720,745 B2 | 4/2004 | Lys |
| 6,727,091 B2 | 4/2004 | Darlington |
| 6,738,551 B2 | 5/2004 | Noda |
| 6,743,171 B1 | 6/2004 | Bowles |
| 6,755,783 B2 | 6/2004 | Cosentino |
| 6,756,998 B1 | 6/2004 | Bilger |
| 6,757,710 B2 | 6/2004 | Reed |
| 6,769,915 B2 | 8/2004 | Murgia |
| 6,772,016 B1 | 8/2004 | Oern |
| 6,774,802 B2 | 8/2004 | Bachinski |
| 6,782,351 B2 | 8/2004 | Reichel |
| 6,806,659 B1 | 10/2004 | Mueller |
| 6,834,208 B2 | 12/2004 | Gonzales |
| 6,862,529 B2 | 3/2005 | Brown |
| 6,865,428 B2 | 3/2005 | Gonzales |
| 6,872,221 B2 | 3/2005 | Lytle |
| 6,878,191 B2 | 4/2005 | Escaffre |
| 6,879,451 B1 | 4/2005 | Hewlett |
| 6,884,078 B2 | 4/2005 | Wiig |
| 6,888,453 B2 | 5/2005 | Lutz |
| 6,888,779 B2 | 5/2005 | Mollicone |
| 6,904,508 B2 | 6/2005 | Selkirk |
| 6,912,429 B1 | 6/2005 | Bilger |
| 6,923,653 B2 | 8/2005 | Ito |
| 6,933,486 B2 | 8/2005 | Pitigoi-Aron |
| 6,955,684 B2 | 10/2005 | Savage, Jr. |
| 6,964,638 B2 | 11/2005 | Theodoracopulos |
| 6,967,565 B2 | 11/2005 | Lingemann |
| 6,991,029 B2 | 1/2006 | Orfield |
| 6,992,803 B2 | 1/2006 | Chang |
| 7,004,606 B2 | 2/2006 | Schofield |
| 7,014,336 B1 | 3/2006 | Ducharme |
| 7,024,256 B2 | 4/2006 | Krzyzanowski |
| 7,038,399 B2 | 5/2006 | Lys |
| 7,065,280 B2 | 6/2006 | Ogawa |
| 7,067,995 B2 | 6/2006 | Gunter |
| 7,081,128 B2 | 7/2006 | Hart |
| D526,512 S | 8/2006 | Hahn |
| 7,092,101 B2 | 8/2006 | Brady |
| 7,095,056 B2 | 8/2006 | Vitta |
| 7,097,111 B2 | 8/2006 | Riley |
| 7,099,723 B2 | 8/2006 | Gonzales |
| 7,113,086 B2 | 9/2006 | Shorrock |
| D530,940 S | 10/2006 | Raile |
| 7,129,855 B2 | 10/2006 | Krzyzanowski |
| 7,145,295 B1 | 12/2006 | Lee |
| 7,145,614 B2 | 12/2006 | Lee |
| 7,173,384 B2 | 2/2007 | Plotz |
| 7,190,126 B1 | 3/2007 | Paton |
| 7,196,619 B2 | 3/2007 | Perlman |
| 7,202,613 B2 | 4/2007 | Morgan |
| 7,204,611 B2 | 4/2007 | Kupper |
| 7,213,940 B1 | 5/2007 | Van De Ven |
| 7,215,086 B2 | 5/2007 | Maxik |
| 7,224,282 B2 | 5/2007 | Terauchi |
| 7,234,943 B1 | 6/2007 | Aleali |
| 7,256,554 B2 | 8/2007 | Lys |
| 7,260,950 B2 | 8/2007 | Choi |
| 7,274,160 B2 | 9/2007 | Mueller |
| 7,288,902 B1 | 10/2007 | Melanson |
| 7,294,107 B2 | 11/2007 | Simon |
| 7,298,871 B2 | 11/2007 | Lee |
| 7,302,313 B2 | 11/2007 | Sharp |
| 7,308,296 B2 | 12/2007 | Lys |
| 7,319,298 B2 | 1/2008 | Jungwirth |
| 7,324,874 B2 | 1/2008 | Jung |
| 7,327,337 B2 | 2/2008 | Callahan |
| 7,328,243 B2 | 2/2008 | Yeager |
| 7,347,818 B2 | 3/2008 | Simon |
| 7,348,949 B2 | 3/2008 | Lee |
| D566,428 S | 4/2008 | Kester |
| 7,354,172 B2 | 4/2008 | Chemel |
| 7,358,679 B2 | 4/2008 | Lys |
| 7,364,583 B2 | 4/2008 | Rose |
| 7,366,989 B2 | 4/2008 | Naik |
| 7,369,903 B2 | 5/2008 | Diederiks |
| 7,387,405 B2 | 6/2008 | Ducharme |
| 7,415,310 B2 | 8/2008 | Bovee |
| 7,446,303 B2 | 11/2008 | Maniam |
| 7,453,217 B2 | 11/2008 | Lys |
| 7,457,834 B2 | 11/2008 | Jung |
| 7,507,091 B1 | 3/2009 | Aleali |
| 7,520,634 B2 | 4/2009 | Ducharme |
| 7,524,279 B2 | 4/2009 | Auphan |
| 7,534,255 B1 | 5/2009 | Streeter |
| 7,536,388 B2 | 5/2009 | Jung |
| 7,545,267 B2 | 6/2009 | Stortoni |
| 7,553,039 B2 * | 6/2009 | Harris ............... F21S 8/00 362/267 |
| 7,556,604 B2 | 7/2009 | Murata |
| 7,557,521 B2 | 7/2009 | Lys |
| 7,558,546 B2 | 7/2009 | Johnson |
| 7,567,956 B2 | 7/2009 | Yu |
| 7,572,028 B2 | 8/2009 | Mueller |
| 7,573,210 B2 | 8/2009 | Ashdown |
| 7,574,320 B2 | 8/2009 | Corwin |
| 7,577,915 B2 | 8/2009 | Hunter |
| 7,621,871 B2 | 11/2009 | Downs, III |
| 7,624,028 B1 | 11/2009 | Brown |
| 7,647,285 B2 | 1/2010 | Heckerman |
| 7,652,582 B2 | 1/2010 | Littell |
| 7,659,673 B2 | 2/2010 | Lys |
| 7,676,280 B1 | 3/2010 | Bash |
| 7,679,281 B2 | 3/2010 | Kim |
| 7,680,745 B2 | 3/2010 | Hunter |
| 7,689,437 B1 | 3/2010 | Teller |
| 7,725,842 B2 | 5/2010 | Bronkema |
| 7,759,854 B2 | 7/2010 | Miller |
| 7,766,503 B2 | 8/2010 | Heiking |
| 7,767,280 B2 | 8/2010 | Klasen-Memmer |
| 7,772,965 B2 | 8/2010 | Farhan |
| 7,779,097 B2 | 8/2010 | Lamkin |
| 7,792,920 B2 | 9/2010 | Istvan |
| 7,827,039 B2 | 11/2010 | Butcher |
| 7,828,205 B2 | 11/2010 | Cronin |
| 7,837,472 B1 | 11/2010 | Elsmore |
| 7,839,275 B2 | 11/2010 | Spalink |
| 7,840,310 B2 | 11/2010 | Orfield |
| 7,843,353 B2 | 11/2010 | Pan |
| 7,845,823 B2 | 12/2010 | Mueller |
| 7,848,945 B2 | 12/2010 | Rozell |
| D632,102 S | 2/2011 | Sato |
| 7,878,810 B2 | 2/2011 | Kuntz |
| D634,952 S | 3/2011 | Gile |
| 7,901,071 B1 | 3/2011 | Kulas |
| 7,906,789 B2 | 3/2011 | Jung |
| 7,914,172 B2 | 3/2011 | Nagara |
| 7,918,406 B2 | 4/2011 | Rosen |
| 7,918,407 B2 | 4/2011 | Patch |
| 7,925,673 B2 | 4/2011 | Beard |
| 7,953,678 B2 | 5/2011 | Hunter |
| 7,967,731 B2 | 6/2011 | Kil |
| 7,973,759 B2 | 7/2011 | Huang |
| 7,977,904 B2 | 7/2011 | Berman |
| 7,987,490 B2 | 7/2011 | Ansari |
| 8,025,687 B2 | 9/2011 | Streeter |
| 8,028,706 B2 | 10/2011 | Skene |
| 8,035,320 B2 | 10/2011 | Sibert |
| 8,038,615 B2 | 10/2011 | Gobeyn |
| 8,042,049 B2 | 10/2011 | Killian |
| 8,064,295 B2 | 11/2011 | Palmer |
| 8,066,405 B2 | 11/2011 | Simon |
| 8,081,216 B2 | 12/2011 | Cheung |
| 8,083,675 B2 | 12/2011 | Robinson |
| 8,086,407 B2 | 12/2011 | Chan |
| 8,095,153 B2 | 1/2012 | Jenkins |

(56) References Cited

U.S. PATENT DOCUMENTS

| | | |
|---|---|---|
| 8,100,552 B2 | 1/2012 | Spero |
| 8,100,746 B2 | 1/2012 | Heidel |
| 8,137,108 B2 | 3/2012 | Hamway |
| 8,140,391 B2 | 3/2012 | Jacobi |
| 8,143,792 B2 | 3/2012 | Joo |
| 8,147,302 B2 | 4/2012 | Desrochers |
| 8,150,707 B2 | 4/2012 | Hayet |
| 8,154,398 B2 | 4/2012 | Rolf |
| 8,159,150 B2 | 4/2012 | Ashdown |
| 8,172,153 B1 | 5/2012 | Kennedy |
| 8,188,873 B2 | 5/2012 | Barth |
| 8,200,744 B2 | 6/2012 | Jung |
| 8,202,095 B2 | 6/2012 | Shankle |
| 8,219,115 B1 | 7/2012 | Nelissen |
| 8,226,418 B2 | 7/2012 | Lycas |
| D666,123 S | 8/2012 | Sichello |
| 8,253,349 B2 | 8/2012 | Shteynberg |
| 8,271,575 B2 | 9/2012 | Hunter |
| 8,292,468 B2 | 10/2012 | Narendran |
| 8,296,408 B2 | 10/2012 | Anke |
| 8,301,482 B2 | 10/2012 | Reynolds |
| 8,308,784 B2 | 11/2012 | Streeter |
| 8,321,192 B2 | 11/2012 | Boyce |
| 8,344,665 B2 | 1/2013 | Verfuerth |
| 8,352,408 B2 | 1/2013 | Guillama |
| 8,358,214 B2 | 1/2013 | Amigo |
| 8,359,208 B2 | 1/2013 | Slutzky |
| 8,380,359 B2 | 2/2013 | Duchene |
| 8,385,812 B2 | 2/2013 | Bertelsen |
| 8,392,025 B2 | 3/2013 | Orfield |
| 8,429,223 B2 | 4/2013 | Gilley |
| 8,436,556 B2 | 5/2013 | Eisele |
| 8,446,275 B2 | 5/2013 | Utter, II |
| 8,449,300 B2 | 5/2013 | Lycas |
| 8,454,729 B2 | 6/2013 | Mittelmark |
| 8,469,547 B2 | 6/2013 | Paolini |
| 8,484,153 B2 | 7/2013 | Mott |
| 8,490,006 B1 | 7/2013 | Reeser |
| 8,497,871 B2 | 7/2013 | Zulch |
| 8,506,612 B2 | 8/2013 | Ashdown |
| 8,508,169 B2 | 8/2013 | Zaharchuk |
| 8,515,785 B2 | 8/2013 | Clark |
| 8,527,213 B2 | 9/2013 | Kailas |
| 8,540,515 B2 | 9/2013 | Williams |
| 8,543,244 B2 | 9/2013 | Keeling |
| 8,543,665 B2 | 9/2013 | Ansari |
| 8,558,466 B2 | 10/2013 | Curasi |
| 8,558,687 B2 | 10/2013 | Haupt |
| 8,560,344 B2 | 10/2013 | Earles |
| 8,609,121 B2 | 12/2013 | Averett |
| 8,622,560 B2 | 1/2014 | Di Trapani |
| 8,630,741 B1 | 1/2014 | Matsuoka |
| 8,632,209 B2 | 1/2014 | Graeber |
| 8,640,038 B1 | 1/2014 | Reeser |
| 8,655,717 B2 | 2/2014 | Schwarzberg |
| 8,660,861 B2 | 2/2014 | Chun |
| 8,662,897 B2 | 3/2014 | Sims, Jr. |
| 8,666,666 B2 | 3/2014 | Bassa |
| 8,674,608 B2 | 3/2014 | Holland |
| 8,674,842 B2 | 3/2014 | Zishaan |
| 8,690,771 B2 | 4/2014 | Wekell |
| 8,707,619 B2 | 4/2014 | Edwards |
| 8,716,952 B2 | 5/2014 | Van De Ven |
| 8,740,623 B2 | 6/2014 | Walker |
| 8,755,942 B2 | 6/2014 | Bonilla |
| 8,760,370 B2 | 6/2014 | Maxik |
| 8,783,902 B2 | 7/2014 | Takakura |
| 8,795,169 B2 | 8/2014 | Cosentino |
| 8,801,636 B2 | 8/2014 | Lewicke |
| 8,823,507 B1 | 9/2014 | Touloumtzis |
| 8,827,489 B2 | 9/2014 | Li |
| 8,836,243 B2 | 9/2014 | Eisele |
| 8,843,484 B2 | 9/2014 | Gu |
| 8,852,254 B2 | 10/2014 | Moscovici |
| 8,855,757 B2 | 10/2014 | Kapoor |
| 8,862,532 B2 | 10/2014 | Beaulieu |
| 8,870,740 B2 | 10/2014 | Clegg |
| 8,896,427 B1 | 11/2014 | Ramirez |
| 8,907,803 B2 | 12/2014 | Martin |
| 8,924,026 B2 | 12/2014 | Federspiel |
| 8,939,885 B2 | 1/2015 | Martin |
| 8,941,500 B1 | 1/2015 | Faaborg |
| 8,952,626 B2 | 2/2015 | Huang |
| 8,961,414 B2 | 2/2015 | Teller |
| 8,975,827 B2 | 3/2015 | Chobot |
| 8,979,913 B2 | 3/2015 | D Ambrosio |
| 8,986,204 B2 | 3/2015 | Pacey |
| 8,986,427 B2 | 3/2015 | Hauville |
| 9,007,877 B2 | 4/2015 | Godlieb |
| 9,010,019 B2 | 4/2015 | Mittelmark |
| 9,015,610 B2 | 4/2015 | Hunter |
| 9,020,647 B2 | 4/2015 | Johnson |
| 9,032,097 B2 | 5/2015 | Albanese |
| 9,032,215 B2 | 5/2015 | Kalofonos |
| 9,041,530 B2 | 5/2015 | Sprigg |
| 9,044,567 B2 | 6/2015 | Poirrier |
| 9,063,739 B2 | 6/2015 | Ward |
| 9,066,405 B2 | 6/2015 | Van De Ven |
| 9,068,887 B1 | 6/2015 | Bennouri |
| D734,958 S | 7/2015 | Gosling |
| 9,095,029 B2 | 7/2015 | Lu |
| D737,078 S | 8/2015 | McKinney |
| 9,098,114 B2 | 8/2015 | Potter |
| 9,104,183 B2 | 8/2015 | Zheng |
| 9,110,958 B2 | 8/2015 | Brust |
| 9,118,499 B2 | 8/2015 | Hunter |
| 9,125,257 B2 | 9/2015 | Eisele |
| 9,125,274 B1 | 9/2015 | Brunault |
| 9,131,573 B2 | 9/2015 | Maxik |
| 9,147,296 B2 | 9/2015 | Ricci |
| 9,154,559 B1 | 10/2015 | Bovee |
| 9,155,165 B2 | 10/2015 | Chobot |
| 9,204,518 B2 | 12/2015 | Jung |
| 9,220,202 B2 | 12/2015 | Maxik |
| 9,226,371 B2 | 12/2015 | Mohan |
| 9,230,064 B2 | 1/2016 | Yanev |
| 9,230,560 B2 | 1/2016 | Ehsani |
| 9,235,978 B1 | 1/2016 | Charlton |
| 9,236,026 B2 | 1/2016 | Jia |
| 9,248,309 B2 | 2/2016 | Pugh |
| 9,251,716 B2 | 2/2016 | Drane |
| 9,286,442 B2 | 3/2016 | Csoma |
| 9,297,748 B2 | 3/2016 | Risk |
| 9,306,763 B2 | 4/2016 | Tatzel |
| 9,307,608 B2 | 4/2016 | Maxik |
| 9,326,363 B2 | 4/2016 | Godlieb |
| 9,339,227 B2 | 5/2016 | D'Arcy et al. |
| 9,345,091 B2 | 5/2016 | Pickard |
| 9,360,364 B2 | 6/2016 | Hingorani |
| 9,360,731 B2 | 6/2016 | Berman |
| 9,370,689 B2 | 6/2016 | Guillama |
| D761,598 S | 7/2016 | Goodman |
| 9,380,978 B2 | 7/2016 | Reiner |
| 9,392,665 B2 | 7/2016 | Eisele |
| 9,401,098 B2 | 7/2016 | Ellis |
| 9,410,664 B2 | 8/2016 | Krames |
| 9,420,667 B2 | 8/2016 | Mohan |
| 9,420,671 B1 | 8/2016 | Sugimoto |
| 9,426,867 B2 | 8/2016 | Beghelli |
| 9,429,009 B2 | 8/2016 | Paulk |
| 9,430,617 B2 | 8/2016 | Brust |
| 9,430,927 B2 | 8/2016 | Yu |
| 9,450,904 B2 | 9/2016 | Wheeler |
| 9,456,482 B1 | 9/2016 | Pope |
| 9,465,392 B2 | 10/2016 | Bradley |
| 9,471,751 B1 | 10/2016 | Kahn |
| 9,473,321 B1 | 10/2016 | Bazar |
| 9,480,115 B2 | 10/2016 | Bradford |
| 9,493,112 B2 | 11/2016 | Thomas |
| 9,500,325 B2 | 11/2016 | Tong et al. |
| 9,501,049 B2 | 11/2016 | Rajalakshmi |
| 9,510,426 B2 | 11/2016 | Chemel |
| 9,526,455 B2 | 12/2016 | Horseman |
| 9,528,876 B2 | 12/2016 | Micheels |

(56) References Cited

U.S. PATENT DOCUMENTS

| | | |
|---|---|---|
| 9,562,702 B2 | 2/2017 | Law |
| 9,576,939 B2 | 2/2017 | Roth |
| 9,589,475 B2 | 3/2017 | Lycas |
| 9,589,480 B2 | 3/2017 | Ellis |
| 9,593,861 B1 | 3/2017 | Burnett |
| 9,595,118 B2 | 3/2017 | Maxik |
| 9,609,724 B2 | 3/2017 | Bulut |
| 9,615,429 B2 | 4/2017 | Roosli |
| 9,636,520 B2 | 5/2017 | Pedersen |
| 9,642,209 B2 | 5/2017 | Eisele |
| 9,655,195 B2 | 5/2017 | Tseng |
| 9,659,150 B2 | 5/2017 | Greene |
| 9,661,715 B2 | 5/2017 | Van De Ven |
| RE46,430 E | 6/2017 | Sibert |
| 9,672,335 B2 | 6/2017 | Shuart |
| 9,672,472 B2 | 6/2017 | Snyder |
| 9,687,187 B2 | 6/2017 | Dagum |
| 9,693,724 B2 | 7/2017 | Dagum |
| 9,694,496 B2 | 7/2017 | Martinson |
| 9,696,052 B2 | 7/2017 | Malchiondo |
| 9,699,874 B2 | 7/2017 | Phillips |
| 9,703,931 B2 | 7/2017 | Hinkel |
| 9,715,242 B2 | 7/2017 | Pillai |
| 9,717,459 B2 | 8/2017 | Sereno |
| 9,730,298 B2 | 8/2017 | Vangeel |
| 9,734,293 B2 | 8/2017 | Collins, Jr. |
| 9,734,542 B2 | 8/2017 | Ji |
| 9,737,842 B2 | 8/2017 | Matlin |
| 9,750,116 B2 | 8/2017 | Witzgall |
| 9,763,592 B2 | 9/2017 | Le |
| 9,774,697 B2 | 9/2017 | Li |
| 9,788,373 B1 | 10/2017 | Chowdhury |
| 9,791,129 B2 | 10/2017 | Dennis |
| 9,794,355 B2 | 10/2017 | Moghaddam |
| 9,801,259 B2 | 10/2017 | Rasmussen |
| 9,820,656 B2 | 11/2017 | Olivier |
| 9,827,439 B2 | 11/2017 | Maxik |
| 9,839,083 B2 | 12/2017 | Van De Ven |
| 9,842,313 B2 | 12/2017 | B'Far |
| 9,848,811 B2 | 12/2017 | Yasumura |
| 9,870,449 B2 | 1/2018 | Rajan |
| 9,874,317 B2 | 1/2018 | Dijken |
| 9,875,667 B2 | 1/2018 | Thompson |
| 9,881,511 B1 | 1/2018 | Srinivasan |
| 9,883,563 B2 | 1/2018 | Bosua |
| 9,887,854 B2 | 2/2018 | Park |
| 9,890,969 B2 | 2/2018 | Martin |
| 9,894,729 B2 | 2/2018 | Forbis |
| 9,907,149 B1 | 2/2018 | Dolan |
| 9,909,772 B2 | 3/2018 | Bazar |
| 9,913,583 B2 | 3/2018 | Smith, Sr. |
| 9,915,438 B2 | 3/2018 | Cheatham, III |
| 9,916,474 B2 | 3/2018 | Tribble |
| 9,924,243 B2 | 3/2018 | Lupien |
| 9,933,182 B2 | 4/2018 | Alfakhrany |
| 9,939,823 B2 | 4/2018 | Ovadia |
| 9,944,519 B2 | 4/2018 | Bohler |
| 9,949,074 B2 | 4/2018 | Austraat |
| 9,952,614 B2 | 4/2018 | Hunter |
| 9,954,147 B2 | 4/2018 | Pentlehner |
| 9,955,423 B2 | 4/2018 | Kates |
| 9,955,550 B2 | 4/2018 | Baek |
| 9,958,180 B2 | 5/2018 | Mahar |
| 9,959,997 B2 | 5/2018 | Bailey |
| 9,984,590 B2 | 5/2018 | Stevens |
| 9,986,313 B2 | 5/2018 | Schwarzkopf |
| 9,992,292 B2 | 6/2018 | Gunnarsson |
| 9,993,198 B2 | 6/2018 | Dugan |
| 10,001,789 B2 | 6/2018 | Hunka |
| 10,015,865 B2 | 7/2018 | Engelen |
| 10,019,690 B2 | 7/2018 | Oobayashi |
| 10,022,556 B1 | 7/2018 | Holbert |
| 10,024,699 B2 | 7/2018 | Rapetti Mogol |
| 10,030,833 B2 | 7/2018 | Adler |
| 10,031,973 B2 | 7/2018 | Dey |
| 10,039,169 B2 | 7/2018 | Chen |
| 10,042,336 B2 | 8/2018 | Cipollo |
| 10,047,971 B2 | 8/2018 | Nyamjav |
| 10,051,707 B2 | 8/2018 | Deixler |
| 10,052,061 B2 | 8/2018 | Raymann |
| 10,054,534 B1 | 8/2018 | Nourbakhsh |
| 10,057,963 B2 | 8/2018 | Mead |
| 10,060,787 B2 | 8/2018 | Balooch |
| 10,064,255 B2 | 8/2018 | Barroso |
| 10,068,297 B2 | 9/2018 | Hull Roskos |
| 10,072,866 B2 | 9/2018 | Bazar |
| 10,075,757 B2 | 9/2018 | Ugan |
| 10,078,865 B2 | 9/2018 | Joshi |
| 10,088,577 B2 | 10/2018 | Klein |
| 10,091,017 B2 | 10/2018 | Landow |
| 10,091,303 B1 | 10/2018 | Ledvina |
| 10,092,772 B1 | 10/2018 | Makesh |
| 10,129,367 B2 | 11/2018 | Yan |
| 10,139,118 B2 | 11/2018 | Law |
| 10,154,574 B2 | 12/2018 | Yeh |
| 10,178,972 B2 | 1/2019 | Raymann |
| 10,203,267 B2 | 2/2019 | D'Orlando |
| 10,230,538 B2 | 3/2019 | Killian |
| 10,234,162 B2 | 3/2019 | Lu |
| 10,242,757 B2 | 3/2019 | Baughman |
| 10,244,606 B2 | 3/2019 | Wingren |
| 10,265,011 B2 | 4/2019 | Garnavi |
| 10,271,400 B2 | 4/2019 | Parker |
| 10,304,249 B2 | 5/2019 | Cronin |
| 10,420,912 B2 | 9/2019 | Lütz |
| 10,527,490 B2 | 1/2020 | Dumont |
| 10,561,376 B1 | 2/2020 | Kahn |
| 10,602,599 B2 | 3/2020 | Wouhaybi |
| 10,709,899 B1 | 7/2020 | Maa |
| 10,775,068 B2 | 9/2020 | Lee |
| 10,845,829 B2 | 11/2020 | Pillai |
| 10,917,259 B1 | 2/2021 | Chein |
| 10,948,348 B2 | 3/2021 | Rountree |
| 10,972,360 B2 | 4/2021 | Cahill |
| 10,976,065 B2 | 4/2021 | Kohn |
| 10,980,096 B2 | 4/2021 | Summers |
| 11,078,899 B2 | 8/2021 | Mou |
| 11,137,163 B2 | 10/2021 | Nasis |
| 11,141,688 B2 | 10/2021 | Hur |
| 11,187,419 B2 | 11/2021 | Aleti |
| 2002/0072322 A1 | 6/2002 | Sharp |
| 2002/0072859 A1 | 6/2002 | Kajimoto |
| 2002/0096121 A1 | 7/2002 | Ingman |
| 2002/0119281 A1* | 8/2002 | Higgins ............... D06N 7/0073 428/95 |
| 2002/0128864 A1 | 9/2002 | Maus |
| 2002/0163529 A1 | 11/2002 | Evanicky |
| 2002/0187082 A1 | 12/2002 | Wu |
| 2002/0192624 A1 | 12/2002 | Darby |
| 2003/0100837 A1 | 5/2003 | Lys |
| 2003/0133292 A1 | 7/2003 | Mueller |
| 2003/0199244 A1 | 10/2003 | Siddaramanna |
| 2003/0209140 A1 | 11/2003 | Kutt |
| 2003/0209501 A1 | 11/2003 | Leung |
| 2004/0002792 A1 | 1/2004 | Hoffknecht |
| 2004/0052076 A1 | 3/2004 | Mueller |
| 2004/0060677 A1 | 4/2004 | Huang |
| 2004/0065098 A1 | 4/2004 | Choi |
| 2004/0105264 A1 | 6/2004 | Spero |
| 2004/0111036 A1 | 6/2004 | Nissila |
| 2004/0152995 A1 | 8/2004 | Cox |
| 2004/0160199 A1 | 8/2004 | Morgan |
| 2004/0176666 A1 | 9/2004 | Chait |
| 2004/0178751 A1 | 9/2004 | Mueller |
| 2004/0212321 A1 | 10/2004 | Lys |
| 2004/0222307 A1* | 11/2004 | DeLuca ............. G05D 23/1904 236/46 R |
| 2004/0245351 A1 | 12/2004 | Orfield |
| 2004/0264193 A1 | 12/2004 | Okumura |
| 2004/0267385 A1 | 12/2004 | Lingemann |
| 2005/0004942 A1 | 1/2005 | Madsen |
| 2005/0053904 A1 | 3/2005 | Shephard |
| 2005/0057158 A1 | 3/2005 | Chang |
| 2005/0110416 A1 | 5/2005 | Veskovic |

(56) References Cited

U.S. PATENT DOCUMENTS

| | | |
|---|---|---|
| 2005/0125275 A1 | 6/2005 | Wright |
| 2005/0142524 A1 | 6/2005 | Simon |
| 2005/0151489 A1 | 7/2005 | Lys |
| 2005/0177957 A1 | 8/2005 | Long |
| 2005/0191505 A1 | 9/2005 | Akarsu |
| 2005/0200578 A1 | 9/2005 | Lee |
| 2005/0213353 A1 | 9/2005 | Lys |
| 2005/0214533 A1 | 9/2005 | Shimosaki |
| 2005/0218870 A1 | 10/2005 | Lys |
| 2005/0225976 A1 | 10/2005 | Zampini |
| 2005/0231133 A1 | 10/2005 | Lys |
| 2005/0236998 A1 | 10/2005 | Mueller |
| 2005/0253533 A1 | 11/2005 | Lys |
| 2005/0281531 A1 | 12/2005 | Unmehopa |
| 2006/0000257 A1 | 1/2006 | Samadpour |
| 2006/0002110 A1 | 1/2006 | Dowling |
| 2006/0017928 A1 | 1/2006 | Crowther |
| 2006/0018118 A1 | 1/2006 | Lee |
| 2006/0018428 A1 | 1/2006 | Li |
| 2006/0026972 A1 | 2/2006 | Masui |
| 2006/0074340 A1 | 4/2006 | Murata |
| 2006/0092520 A1 | 5/2006 | Buchsbaum |
| 2006/0103728 A1 | 5/2006 | Ishigami |
| 2006/0106437 A1 | 5/2006 | Czeisler |
| 2006/0111944 A1 | 5/2006 | Sirmans |
| 2006/0154596 A1 | 7/2006 | Meneely |
| 2006/0162552 A1 | 7/2006 | Yost |
| 2006/0172579 A1 | 8/2006 | Murphy |
| 2006/0173580 A1 | 8/2006 | Desrochers |
| 2006/0184283 A1 | 8/2006 | Lee |
| 2006/0207730 A1 | 9/2006 | Berman |
| 2006/0246149 A1 | 11/2006 | Buchholz |
| 2006/0252014 A1 | 11/2006 | Simon |
| 2007/0001617 A1 | 1/2007 | Pogodayev |
| 2007/0024210 A1 | 2/2007 | Zwanenburg |
| 2007/0084937 A1 | 4/2007 | Ahmed |
| 2007/0115665 A1 | 5/2007 | Mueller |
| 2007/0162858 A1 | 7/2007 | Hurley |
| 2007/0166676 A1 | 7/2007 | Bird |
| 2007/0198226 A1 | 8/2007 | Lee |
| 2007/0240437 A1 | 10/2007 | Yonezawa |
| 2007/0276270 A1 | 11/2007 | Tran |
| 2007/0288247 A1 | 12/2007 | Mackay |
| 2008/0031832 A1 | 2/2008 | Wakefield |
| 2008/0103561 A1 | 5/2008 | Moscovici |
| 2008/0116780 A1 | 5/2008 | Kupper |
| 2008/0129174 A1 | 6/2008 | Schafer |
| 2008/0146892 A1 | 6/2008 | LeBoeuf |
| 2008/0182506 A1 | 7/2008 | Jackson |
| 2008/0187894 A1 | 8/2008 | Cady |
| 2008/0224121 A1 | 9/2008 | Bose |
| 2008/0225021 A1 | 9/2008 | Hekstra |
| 2008/0246629 A1 | 10/2008 | Tsui |
| 2008/0277486 A1 | 11/2008 | Seem |
| 2008/0294012 A1 | 11/2008 | Kurtz |
| 2008/0297027 A1 | 12/2008 | Miller |
| 2009/0015403 A1 | 1/2009 | Kuris |
| 2009/0053989 A1 | 2/2009 | Lunde |
| 2009/0065596 A1 | 3/2009 | Seem |
| 2009/0068089 A1 | 3/2009 | Hussain |
| 2009/0104086 A1 | 4/2009 | Zax |
| 2009/0115597 A1 | 5/2009 | Giacalone |
| 2009/0126382 A1 | 5/2009 | Rubino |
| 2009/0128044 A1 | 5/2009 | Nevins |
| 2009/0169425 A1 | 7/2009 | Park |
| 2009/0177613 A1 | 7/2009 | Martinez |
| 2009/0223126 A1 | 9/2009 | Garner |
| 2009/0241496 A1 | 10/2009 | Pintault |
| 2009/0242485 A1 | 10/2009 | Cabados |
| 2009/0243517 A1 | 10/2009 | Verfuerth |
| 2009/0273470 A1 | 11/2009 | Sinkevicius |
| 2009/0278464 A1 | 11/2009 | Chung |
| 2009/0287064 A1 | 11/2009 | Dougherty, Jr. |
| 2009/0292180 A1 | 11/2009 | Mirow |
| 2009/0300673 A1 | 12/2009 | Bachet |
| 2010/0021710 A1 | 1/2010 | Hunt |
| 2010/0084996 A1 | 4/2010 | Van De Sluis |
| 2010/0119461 A1 | 5/2010 | Bicard-Benhamou |
| 2010/0146855 A1 | 6/2010 | Ma |
| 2010/0169108 A1 | 7/2010 | Karkanias |
| 2010/0185064 A1 | 7/2010 | Bandic |
| 2010/0197495 A1 | 8/2010 | Filippini |
| 2010/0217099 A1 | 8/2010 | Leboeuf |
| 2010/0265803 A1 | 10/2010 | Lee |
| 2010/0277106 A1 | 11/2010 | Baaijens |
| 2010/0289643 A1 | 11/2010 | Trundle |
| 2010/0295244 A1 | 11/2010 | Stut |
| 2010/0298981 A1 | 11/2010 | Chamorro |
| 2010/0301776 A1 | 12/2010 | Feri |
| 2011/0010014 A1 | 1/2011 | Oexman |
| 2011/0066465 A1 | 3/2011 | Orfield |
| 2011/0084614 A1 | 4/2011 | Eisele |
| 2011/0178977 A1 | 7/2011 | Drees |
| 2011/0186644 A1 | 8/2011 | Yoshii |
| 2011/0190913 A1 | 8/2011 | Van De Sluis |
| 2011/0190945 A1 | 8/2011 | Yoshii |
| 2011/0237905 A1 | 9/2011 | Kutzik |
| 2011/0270446 A1 | 11/2011 | Scharf |
| 2011/0307112 A1 | 12/2011 | Barrilleaux |
| 2012/0003198 A1 | 1/2012 | Barker |
| 2012/0011033 A1 | 1/2012 | Salgia |
| 2012/0019386 A1 | 1/2012 | Doraiswami |
| 2012/0031984 A1 | 2/2012 | Feldmeier |
| 2012/0064818 A1 | 3/2012 | Kurelowech |
| 2012/0072032 A1 | 3/2012 | Powell |
| 2012/0139720 A1 | 6/2012 | Mazar |
| 2012/0158203 A1 | 6/2012 | Feldstein |
| 2012/0176041 A1 | 7/2012 | Birru |
| 2012/0190001 A1 | 7/2012 | Knight |
| 2012/0206726 A1 | 8/2012 | Pervez |
| 2012/0214143 A1 | 8/2012 | Severson |
| 2012/0241633 A1 | 9/2012 | Smith |
| 2012/0279120 A1 | 11/2012 | Prescott |
| 2012/0298599 A1 | 11/2012 | Sichello |
| 2013/0027637 A1 | 1/2013 | Hosoki |
| 2013/0035208 A1 | 2/2013 | Dalebout |
| 2013/0065098 A1 | 3/2013 | Ohkawa |
| 2013/0073093 A1 | 3/2013 | Songkakul |
| 2013/0081541 A1* | 4/2013 | Hasenoehrl ............... G05F 1/66 96/397 |
| 2013/0090562 A1 | 4/2013 | Ryan |
| 2013/0102852 A1 | 4/2013 | Kozloski |
| 2013/0119891 A1 | 5/2013 | Herremans |
| 2013/0134962 A1 | 5/2013 | Kamel |
| 2013/0141235 A1 | 6/2013 | Utter, II |
| 2013/0144537 A1 | 6/2013 | Schalk |
| 2013/0208576 A1 | 8/2013 | Loree, IV |
| 2013/0229114 A1 | 9/2013 | Eisele |
| 2013/0276371 A1 | 10/2013 | Birru |
| 2013/0331727 A1 | 12/2013 | Zhang |
| 2013/0342111 A1 | 12/2013 | Mohan |
| 2014/0039685 A1 | 2/2014 | Blount |
| 2014/0046173 A1 | 2/2014 | Stack |
| 2014/0052220 A1 | 2/2014 | Pedersen |
| 2014/0058566 A1* | 2/2014 | Rains, Jr. ............... G05B 15/02 700/276 |
| 2014/0067130 A1 | 3/2014 | Pillai |
| 2014/0089836 A1 | 3/2014 | Damani |
| 2014/0093551 A1 | 4/2014 | Averett |
| 2014/0099348 A1 | 4/2014 | Averett |
| 2014/0107846 A1 | 4/2014 | Li |
| 2014/0114889 A1 | 4/2014 | Dagum |
| 2014/0125225 A1 | 5/2014 | Calame |
| 2014/0142760 A1 | 5/2014 | Drees |
| 2014/0155705 A1 | 6/2014 | Papadopoulos |
| 2014/0168636 A1 | 6/2014 | Funamoto |
| 2014/0222210 A1 | 8/2014 | Agarwal |
| 2014/0222241 A1 | 8/2014 | Ols |
| 2014/0243935 A1 | 8/2014 | Brainard |
| 2014/0249447 A1 | 9/2014 | Sereno |
| 2014/0266669 A1 | 9/2014 | Fadell |
| 2014/0277757 A1 | 9/2014 | Wang |
| 2014/0283450 A1 | 9/2014 | Darlington |
| 2014/0298719 A1 | 10/2014 | Mackin |

(56) References Cited

U.S. PATENT DOCUMENTS

| | | |
|---|---|---|
| 2014/0318011 A1 | 10/2014 | Järvinen |
| 2014/0343380 A1 | 11/2014 | Carter |
| 2014/0375230 A1 | 12/2014 | Liu |
| 2015/0015152 A1* | 1/2015 | Aboulnaga ............ H05B 47/20 315/312 |
| 2015/0027879 A1 | 1/2015 | Myre |
| 2015/0048742 A1 | 2/2015 | Wingren |
| 2015/0052975 A1 | 2/2015 | Martin |
| 2015/0066578 A1 | 3/2015 | Manocchia |
| 2015/0088786 A1 | 3/2015 | Anandhakrishnan |
| 2015/0102730 A1 | 4/2015 | Eisele |
| 2015/0119731 A1 | 4/2015 | Yasumura |
| 2015/0126806 A1* | 5/2015 | Barroso ............... A61N 5/0618 315/153 |
| 2015/0134123 A1 | 5/2015 | Obinelo |
| 2015/0154523 A1 | 6/2015 | Oobayashi |
| 2015/0174361 A1 | 6/2015 | Baaijens |
| 2015/0196232 A1 | 7/2015 | Mitsi |
| 2015/0204551 A1 | 7/2015 | Nair |
| 2015/0204561 A1 | 7/2015 | Sadwick |
| 2015/0212057 A1 | 7/2015 | Darveau |
| 2015/0221233 A1 | 8/2015 | Couriol |
| 2015/0227870 A1 | 8/2015 | Noboa |
| 2015/0234369 A1 | 8/2015 | Wen |
| 2015/0289347 A1 | 10/2015 | Baaijens |
| 2015/0309484 A1 | 10/2015 | Lyman |
| 2015/0312696 A1 | 10/2015 | Ribbich |
| 2015/0317592 A1 | 11/2015 | Oobayashi |
| 2015/0338117 A1 | 11/2015 | Henneberger |
| 2015/0382427 A1 | 12/2015 | Eisele |
| 2016/0007905 A1 | 1/2016 | Milner |
| 2016/0019813 A1 | 1/2016 | Mullen |
| 2016/0125758 A1 | 5/2016 | Hong |
| 2016/0139576 A1 | 5/2016 | Aiken |
| 2016/0151603 A1 | 6/2016 | Shouldice |
| 2016/0203700 A1 | 7/2016 | Bruhn |
| 2016/0206898 A1 | 7/2016 | Brainard |
| 2016/0213946 A1 | 7/2016 | Brainard |
| 2016/0231014 A1 | 8/2016 | Ro |
| 2016/0253802 A1 | 9/2016 | Venetianer |
| 2016/0284172 A1 | 9/2016 | Weast |
| 2016/0313245 A1 | 10/2016 | Sato |
| 2016/0316543 A1 | 10/2016 | Liu |
| 2016/0339203 A1 | 11/2016 | Krames |
| 2016/0341436 A1 | 11/2016 | Parker |
| 2016/0377305 A1 | 12/2016 | Kwa |
| 2017/0023225 A1 | 1/2017 | Chen |
| 2017/0023269 A1 | 1/2017 | Gevelber |
| 2017/0038787 A1 | 2/2017 | Baker |
| 2017/0050561 A1 | 2/2017 | Lickfelt |
| 2017/0053068 A1 | 2/2017 | Pillai |
| 2017/0065792 A1 | 3/2017 | Bonvallet |
| 2017/0068782 A1 | 3/2017 | Pillai |
| 2017/0080373 A1 | 3/2017 | Engelhard |
| 2017/0105666 A1 | 4/2017 | Lee |
| 2017/0123440 A1 | 5/2017 | Mangsuli |
| 2017/0136206 A1 | 5/2017 | Pillai |
| 2017/0139386 A1 | 5/2017 | Pillai |
| 2017/0162548 A1 | 6/2017 | Roth |
| 2017/0181685 A1 | 6/2017 | Lee |
| 2017/0188926 A1 | 7/2017 | Oobayashi |
| 2017/0189640 A1 | 7/2017 | Sadwick |
| 2017/0191695 A1 | 7/2017 | Bruhn |
| 2017/0196510 A1 | 7/2017 | Ouwerkerk |
| 2017/0200389 A1 | 7/2017 | Yigal |
| 2017/0208021 A1 | 7/2017 | Ingram |
| 2017/0232225 A1 | 8/2017 | Pedersen |
| 2017/0238401 A1 | 8/2017 | Sadwick |
| 2017/0259079 A1 | 9/2017 | Grajcar |
| 2017/0299210 A1 | 10/2017 | Nyamjav |
| 2017/0300647 A1 | 10/2017 | Goldberg |
| 2017/0300651 A1 | 10/2017 | Strobridge |
| 2017/0300655 A1 | 10/2017 | Lane |
| 2017/0301255 A1 | 10/2017 | Lee |
| 2017/0307243 A1 | 10/2017 | Burt |
| 2017/0319816 A1 | 11/2017 | Sokol |
| 2017/0321923 A1 | 11/2017 | Wiens-Kind |
| 2017/0325310 A1 | 11/2017 | Chen |
| 2017/0326380 A1 | 11/2017 | Moore-Ede |
| 2017/0347907 A1 | 12/2017 | Le |
| 2017/0348506 A1 | 12/2017 | Berman |
| 2017/0350610 A1 | 12/2017 | Michielsen |
| 2017/0356602 A1 | 12/2017 | Lin |
| 2017/0356670 A1 | 12/2017 | Zhang |
| 2017/0359879 A1 | 12/2017 | Eisele |
| 2017/0363314 A1 | 12/2017 | Barber |
| 2018/0011978 A1 | 1/2018 | Reeckmann |
| 2018/0012242 A1 | 1/2018 | Phan |
| 2018/0025125 A1 | 1/2018 | Crane |
| 2018/0025126 A1 | 1/2018 | Barnard |
| 2018/0042077 A1 | 2/2018 | Riley |
| 2018/0043130 A1 | 2/2018 | Martin |
| 2018/0077767 A1 | 3/2018 | Soler |
| 2018/0082261 A1 | 3/2018 | Hendriks |
| 2018/0082393 A1 | 3/2018 | Ahrens |
| 2018/0107962 A1 | 4/2018 | Lundin |
| 2018/0108442 A1 | 4/2018 | Börve |
| 2018/0119973 A1 | 5/2018 | Rothman |
| 2018/0120161 A1 | 5/2018 | Qiu |
| 2018/0120162 A1 | 5/2018 | Qiu |
| 2018/0149802 A1 | 5/2018 | Krames |
| 2018/0154297 A1 | 6/2018 | Maletich |
| 2018/0157864 A1 | 6/2018 | Tribble |
| 2018/0160944 A1 | 6/2018 | Aubert |
| 2018/0165588 A1 | 6/2018 | Saxena |
| 2018/0166171 A1 | 6/2018 | Pulitzer |
| 2018/0178063 A1 | 6/2018 | Silver |
| 2018/0182472 A1 | 6/2018 | Preston |
| 2018/0188701 A1 | 7/2018 | Billings |
| 2018/0193589 A1 | 7/2018 | McLaughlin |
| 2018/0196925 A1 | 7/2018 | Mukherjee |
| 2018/0197625 A1 | 7/2018 | Lobach |
| 2018/0197637 A1 | 7/2018 | Chowdhury |
| 2018/0197638 A1 | 7/2018 | Blanshard |
| 2018/0206783 A1 | 7/2018 | Yoon |
| 2018/0207445 A1 | 7/2018 | Maxik |
| 2018/0209683 A1 | 7/2018 | Cho |
| 2018/0216843 A1 | 8/2018 | Zhou |
| 2018/0218289 A1 | 8/2018 | Albrecht |
| 2018/0226158 A1 | 8/2018 | Fish |
| 2018/0240274 A1 | 8/2018 | Cronin |
| 2018/0247029 A1 | 8/2018 | Fish |
| 2018/0250430 A1 | 9/2018 | Machovina |
| 2018/0264224 A1 | 9/2018 | Gronfier |
| 2018/0266718 A1 | 9/2018 | Gillette |
| 2018/0285934 A1 | 10/2018 | Baughman |
| 2018/0295696 A1 | 10/2018 | Li |
| 2018/0295704 A1 | 10/2018 | Haverlag |
| 2018/0308390 A1 | 10/2018 | Moser |
| 2018/0311464 A1 | 11/2018 | Krames |
| 2018/0318602 A1 | 11/2018 | Ciccarelli |
| 2018/0320919 A1 | 11/2018 | Tang |
| 2018/0322240 A1 | 11/2018 | Goyal |
| 2018/0322253 A1 | 11/2018 | Goyal |
| 2018/0322255 A1 | 11/2018 | Connell, II |
| 2018/0330626 A1 | 11/2018 | Donadio |
| 2018/0331845 A1 | 11/2018 | Warren |
| 2018/0336500 A1 | 11/2018 | Pinho |
| 2018/0336530 A1 | 11/2018 | Johnson |
| 2018/0339127 A1 | 11/2018 | Van Reen |
| 2018/0342327 A1 | 11/2018 | Madan |
| 2018/0349689 A1 | 12/2018 | Lee |
| 2018/0349945 A1 | 12/2018 | Jayaraman |
| 2018/0350455 A1 | 12/2018 | Rosen |
| 2018/0350456 A1 | 12/2018 | Kendrick |
| 2018/0351758 A1 | 12/2018 | Becker |
| 2018/0351761 A1 | 12/2018 | Li |
| 2018/0353073 A1 | 12/2018 | Boucher |
| 2018/0353108 A1 | 12/2018 | Prate |
| 2018/0358117 A1 | 12/2018 | Neagle |
| 2018/0358129 A1 | 12/2018 | Gorzelniak |
| 2018/0358130 A1 | 12/2018 | Schmidt |
| 2018/0369637 A1 | 12/2018 | Hoang |
| 2018/0373843 A1 | 12/2018 | Baughman |

(56) References Cited

U.S. PATENT DOCUMENTS

| | | |
|---|---|---|
| 2018/0374053 A1 | 12/2018 | Willamowski |
| 2018/0374572 A1 | 12/2018 | Ackerman |
| 2018/0374586 A1 | 12/2018 | Baughman |
| 2019/0001059 A1 | 1/2019 | Handler |
| 2019/0005844 A1 | 1/2019 | Dragicevic |
| 2019/0007424 A1 | 1/2019 | Ford |
| 2019/0007927 A1 | 1/2019 | Blahnik |
| 2019/0011146 A1 | 1/2019 | Seo |
| 2019/0013960 A1 | 1/2019 | Sadwick |
| 2019/0014643 A1 | 1/2019 | Gharabegian |
| 2019/0024926 A1 | 1/2019 | Kim |
| 2019/0028549 A1 | 1/2019 | Ledvina |
| 2019/0041080 A1 | 2/2019 | Higuchi |
| 2019/0046109 A1 | 2/2019 | Lewis |
| 2019/0056126 A1 | 2/2019 | Law |
| 2019/0057615 A1 | 2/2019 | Mullen |
| 2019/0075687 A1 | 3/2019 | Brunstetter |
| 2019/0091700 A1 | 3/2019 | Hilbig |
| 2019/0107267 A1 | 4/2019 | Luo |
| 2019/0193508 A1 | 6/2019 | Ganem |
| 2019/0209806 A1 | 7/2019 | Allen |
| 2019/0215184 A1 | 7/2019 | Emigh |
| 2019/0224445 A1 | 7/2019 | Fernandes |
| 2019/0268999 A1 | 8/2019 | Oobayashi |
| 2019/0281681 A1 | 9/2019 | De Bries |
| 2019/0297700 A1 | 9/2019 | Gal |
| 2019/0309975 A1 | 10/2019 | Salem |
| 2019/0320516 A1 | 10/2019 | Parker |
| 2019/0350066 A1 | 11/2019 | Herf |
| 2019/0366032 A1 | 12/2019 | Lockley |
| 2020/0011563 A1 | 1/2020 | Jeong |
| 2020/0101893 A1 | 4/2020 | Studeny |
| 2020/0103841 A1 | 4/2020 | Pillai |
| 2020/0182495 A1 | 6/2020 | Park |
| 2020/0224915 A1 | 7/2020 | Nourbakhsh |
| 2020/0229289 A1 | 7/2020 | Cahill |
| 2020/0298168 A1 | 9/2020 | Lee |
| 2020/0340700 A1 | 10/2020 | Park |
| 2021/0116144 A1 | 4/2021 | Morgan |
| 2021/0207833 A1 | 7/2021 | Dameno |
| 2021/0239339 A1 | 8/2021 | Morgan |
| 2021/0379524 A1 | 12/2021 | Prigge |

FOREIGN PATENT DOCUMENTS

| | | |
|---|---|---|
| CN | 1150882 | 5/1997 |
| CN | 1544222 | 11/2004 |
| CN | 1971268 | 5/2007 |
| CN | 101421558 | 4/2009 |
| CN | 201414191 Y | 2/2010 |
| CN | 101963607 | 2/2011 |
| CN | 101976063 | 2/2011 |
| CN | 102073935 | 5/2011 |
| CN | 102262710 | 11/2011 |
| CN | 202075431 | 12/2011 |
| CN | 102305451 | 1/2012 |
| CN | 202551821 | 11/2012 |
| CN | 103040443 A | 4/2013 |
| CN | 103197659 A | 7/2013 |
| CN | 103277870 | 9/2013 |
| CN | 203175090 U | 9/2013 |
| CN | 103531174 A | 1/2014 |
| CN | 103604198 A | 2/2014 |
| CN | 203454309 U | 2/2014 |
| CN | 204759076 | 11/2015 |
| EP | 0710804 | 5/1996 |
| EP | 1067825 | 1/2001 |
| EP | 1271442 | 1/2003 |
| EP | 1511218 | 3/2005 |
| EP | 1821582 | 8/2007 |
| EP | 2016879 | 1/2009 |
| EP | 2132960 | 12/2009 |
| EP | 2296448 | 3/2011 |
| EP | 2431541 | 3/2012 |
| EP | 2488912 | 8/2012 |
| EP | 3297218 | 10/2020 |
| JP | S60110520 A | 6/1985 |
| JP | H04341243 | 11/1992 |
| JP | H0552361 A | 3/1993 |
| JP | H0658593 | 3/1994 |
| JP | H0658593 A | 3/1994 |
| JP | H06159763 A | 6/1994 |
| JP | H06225858 A | 8/1994 |
| JP | H09303842 A | 11/1997 |
| JP | H10238089 A | 9/1998 |
| JP | 2000130828 | 5/2000 |
| JP | 2000294388 | 10/2000 |
| JP | 2001224078 | 8/2001 |
| JP | 2001286226 | 10/2001 |
| JP | 2001314882 | 11/2001 |
| JP | 2002042546 A | 2/2002 |
| JP | 2002059152 A | 2/2002 |
| JP | 2003042507 | 2/2003 |
| JP | 2003042509 | 2/2003 |
| JP | 2003083590 | 3/2003 |
| JP | 2003232559 | 8/2003 |
| JP | 2004005313 A | 1/2004 |
| JP | 2004053130 A | 2/2004 |
| JP | 2005040769 A | 2/2005 |
| JP | 2005177726 | 7/2005 |
| JP | 2005211319 | 8/2005 |
| JP | 2005235634 | 9/2005 |
| JP | 2006210045 | 8/2006 |
| JP | 2006522699 | 10/2006 |
| JP | 2006321721 | 11/2006 |
| JP | 2006348600 | 12/2006 |
| JP | 2007170761 | 7/2007 |
| JP | 2007184436 | 7/2007 |
| JP | 2008125541 | 6/2008 |
| JP | 2008157548 | 7/2008 |
| JP | 2008204640 | 9/2008 |
| JP | 2010119563 | 6/2010 |
| JP | 2010182661 | 8/2010 |
| JP | 2010239878 | 10/2010 |
| JP | 2011146137 | 7/2011 |
| JP | 2012001931 | 1/2012 |
| JP | 2012149839 A | 8/2012 |
| JP | 2013140523 A | 7/2013 |
| KR | 20000009824 A | 2/2000 |
| KR | 20010048235 | 6/2001 |
| KR | 20030074107 A | 9/2003 |
| KR | 20050003899 | 1/2005 |
| KR | 100771486 | 10/2007 |
| KR | 100804892 | 2/2008 |
| KR | 101102733 | 1/2012 |
| KR | 20120004243 | 1/2012 |
| KR | 101135926 | 4/2012 |
| KR | 20120039359 A | 4/2012 |
| KR | 20130108709 | 10/2013 |
| KR | 20130124184 | 11/2013 |
| WO | 0039964 | 7/2000 |
| WO | 2000058873 | 10/2000 |
| WO | 2004037301 | 5/2004 |
| WO | 2007026387 | 3/2007 |
| WO | 2008043396 | 4/2008 |
| WO | 2008051222 | 5/2008 |
| WO | 2008102308 | 8/2008 |
| WO | 2008120127 | 10/2008 |
| WO | 2008135093 | 11/2008 |
| WO | 2009030641 | 3/2009 |
| WO | 2009044330 | 4/2009 |
| WO | 2009044330 A1 | 4/2009 |
| WO | 2010046875 | 4/2010 |
| WO | 2010087386 | 8/2010 |
| WO | 2010115720 | 10/2010 |
| WO | 2011033377 | 3/2011 |
| WO | 2011046875 | 4/2011 |
| WO | 2012104773 | 8/2012 |
| WO | 2012151407 | 11/2012 |
| WO | 2013014337 | 1/2013 |
| WO | 2013049297 | 4/2013 |
| WO | 2013175348 | 11/2013 |
| WO | 2014013376 | 1/2014 |
| WO | 2014036133 | 3/2014 |

(56) References Cited

FOREIGN PATENT DOCUMENTS

| | | |
|---|---|---|
| WO | 2014071046 | 5/2014 |
| WO | 2015130786 | 9/2015 |
| WO | 2015200730 A1 | 12/2015 |
| WO | 2016019005 A1 | 2/2016 |
| WO | 2016115230 | 7/2016 |
| WO | 2016154320 | 9/2016 |
| WO | 2017008321 | 1/2017 |
| WO | 2018039433 | 3/2018 |
| WO | 2018157063 | 8/2018 |
| WO | 2019151684 | 8/2019 |
| WO | 2019204779 | 10/2019 |
| WO | 2020014688 | 1/2020 |
| WO | 2020073723 | 4/2020 |
| WO | 2020075189 | 4/2020 |
| WO | 2020104878 | 5/2020 |
| WO | 2020146315 | 7/2020 |
| WO | 2020189819 | 9/2020 |
| WO | 2021011822 | 1/2021 |
| WO | 2021249653 | 12/2021 |
| WO | 2021252439 | 12/2021 |

OTHER PUBLICATIONS

Babyak, Richard J., "Ready to roll," Appliance Manufacturer, 2000, vol. 48, No. 9, pp. 40-42.
Bohn, Hendrik et al., "SIRENA—Service Infrastructure for Real-time Embedded Networked Devices: A service oriented framework for different domains," 2006 (7 pages).
Bourcier, Johann et al., "A Dynamic-SOA Home Control Gateway," 2006 (9 pages).
Chen, Chun-Yuan, "A MOM-based Home Automation Platform in Heterogeneous Environments," A Thesis Submitted to Institute of Computer Science and Engineering College of Computer Science National Chiao Tung University, 2006 (93 pages).
Dueñas, Juan C. et al., "An End-to-End Service Provisioning Scenario for the Residential Environment," IEEE Communications Magazine, 2005, pp. 94-100.
Jammes, François et al., "Service-Oriented Device Communications Using the Devices Profile for Web Services," 2005 (8 pages).
Kastner, Wolfgang et al., "Communication Systems for Building Automation and Control," Proceedings of the IEEE, 2005, vol. 93, No. 6, pp. 1178-1203.
Messer, Alan et al., "InterPlay: A Middleware for Seamless Device Integration and Task Orchestration in a Networked Home," Proceedings of the Fourth Annual IEEE International Conference on Pervasive Computing and Communications, 2006 (10 pages).
Mingkhwan, A. et al., "Dynamic service composition in home appliance networks," Multimedia Tools and Applications, 2006, vol. 29, pp. 257-284.
Obiltschnig, Günter, "Automatic Configuration and Service Discovery for Networked Smart Devices," Electronica Embedded Conference Munich, 2006 (8 pages).
Rabbie, Harold M., "Distributed Processing Using Local Operating Networks," Assembly Automation, 1992, vol. 12, No. 1 (7 pages).
Saif, Umar, "Architectures for ubiquitous systems," University of Cambridge Computer Laboratory Technical Report No. 527, 2002 (271 pages).
Akacem et al., "Bedtime and evening light exposure influence circadian timing in preschoolage children: A field study," Neurobiology of Sleep and Circadian Rhythms, 2016, vol. 1, pp. 27-31.
Akacem et al., "Sensitivity of the circadian system to evening bright light in preschool-age children," Physiological Reports, 2018, vol. 6, No. 5, pp. 1-10.
Cho et al., "Effects of artificial light at night on human health: A literature review of observational and experimental studies applied to exposure assessment," Chronobiology International: The Journal of Biological and Medical Rhythm Research, 2015, pp. 1-17.
Dijk et al., "Light, Sleep, and Circadian Rhythms: Together Again," PLoS Biology, 2009, vol. 7, No. 6, pp. 1-4.
Exelmans et al., "Bedtime mobile phone use and sleep in adults," Social Science & Medicine, 2016, vol. 148, pp. 93-101.
Fonken et al., "Dim Light at Night Disrupts Molecular Circadian Rhythms and Affects Metabolism," Journal of Biological Rhythms, Author Manuscript, 2013, vol. 28, No. 4 (15 pages).
Fossum et al., "The Association Between Use of Electronic Media in Bed Before Going to Sleep and Insomnia Symptoms, Daytime Sleepiness, Morningness, and Chronotype," Behavioral Sleep Medicine, 2014, vol. 12, pp. 343-357.
Grønli et al., "Reading from an iPad or from a book in bed: the impact on human sleep. A randomized controlled crossover trial," Sleep Medicine, 2016, vol. 21, pp. 86-92.
Hafner et al., Why sleep matters—the economic costs of insufficient sleep: A cross-country comparative analysis, 2016 (101 pages).
Hysing et al., "Sleep and use of electronic devices in adolescence: results from a large populationbased study," BMJ Open, 2015, vol. 5, pp. 1-7.
Joshi et al., "The importance of temperature and thermoregulation for optimal human sleep," Energy and Buildings, 2016, vol. 131, pp. 153-157.
Lan et al., "Ten questions concerning thermal environment and sleep quality," Building and Environment, 2016, vol. 99, pp. 252-259.
Marinelli et al., "Hours of Television Viewing and Sleep Duration in Children: A Multicenter Birth Cohort Study," JAMA Pediatrics, 2014, vol. 168, No. 5, pp. 458-464.
Peuhkuri et al., "Diet promotes sleep duration and quality," Nutrition Research, 2012, vol. 32, pp. 309-319.
Potter et al., "Circadian Rhythm and Sleep Disruption: Causes, Metabolic Consequences, and Countermeasures," Endocrine Reviews, 2016, vol. 37, No. 6, pp. 584-608.
Strøm-Tejsen et al., "The effects of bedroom air quality on sleep and next-day performance," Indoor Air, 2016, vol. 26, pp. 679-686.
Watson et al., "Recommended Amount of Sleep for a Healthy Adult: A Joint Consensus Statement of the American Academy of Sleep Medicine and Sleep Research Society," Sleep, 2015, vol. 38, No. 6, pp. 843-844.
Yadlapalli et al., "Circadian clock neurons constantly monitor environmental temperature to set sleep timing," Nature, 2018, vol. 555 (21 pages).
Yetish et al., "Natural sleep and its seasonal variations in three pre-industrial societies," Current Biology, Author Manuscript, 2015, vol. 25, No. 21 (19 pages).
"Leed Reference Guide for Building Design and Construction," U.S. Green Building Council, 2013, (67 pages).
"Policy recommendations on protection from exposure to second-hand tobacco smoke," World Health Organization, 2007, pp. 1-50 (56 pages).
"Preventing Diarrhoea Through Better Water, Sanitation and Hygiene: Exposures and impacts in low- and middle-income countries," World Health Organization, 2014, pp. 1-33 (48 pages).
"Proceedings: vol. 1—Indoor Air Quality (IAQ), building related diseases and human response," Healthy Buildings, 2006 (361 pages).
"Social determinants of mental health," World Health Organization and Calouste Gulbenkian Foundation, 2014, pp. 1-52 (54 pages).
Abrahamsson et al., "Impairment of Contrast Sensitivity Function (CSF) as a Measure of Disability Glare," Investigative Ophthalmology & Visual Science, 1986, vol. 27, pp. 1131-1136.
Abt et al., "Characterization of Indoor Particle Sources: A Study Conducted in the Metropolitan Boston Area," Environmental Health Perspectives, 2000, vol. 108, No. 1, pp. 35-44.
Advances in Building Energy Research, 2007, vol. 1 (263 pages).
Ahn, "Synthesis and Characterization of Nanostructured ZnO and SnOx for VOC Sensor Devices," 2011 (204 pages).
Al Horr et al., "Occupant productivity and office indoor environment quality: A review of the literature," Building and Environment, 2016, vol. 105, pp. 369-389.
Allen, Michele L. et al., "Effective Parenting Interventions to Reduce Youth Substance Use: A Systematic Review," Pediatrics, 2016, vol. 138, No. 2 (19 pages).
Amaral et al., "An Overview of Particulate Matter Measurement Instruments," Atmosphere, 2015, vol. 6, pp. 1327-1345.

(56) References Cited

OTHER PUBLICATIONS

American Diabetes Association, "Standards of Medical Care in Diabetes—2017 Abridged for Primary Care Providers," Clinical Diabetes, 2017, vol. 35, No. 1, pp. 5-26 (22 pages).
American Society of Heating, Refrigerating and Air-Conditioning Engineers et al., "Indoor Air Quality Guide: Best Practices for Design, Construction and Commissioning," 2009 (198 pages).
American Society of Heating, Refrigerating and Air-Conditioning Engineers, "Indoor Air Quality Guide: Best Practices for Design, Construction and Commissioning," 2009 (19 pages).
American Society of Heating, Refrigerating and Air-Conditioning Engineers, Inc., ASHRAE Standard 55-2010: Thermal Environmental Conditions for Human Occupancy (44 pages).
Anderson et al., "Clearing the Air: A Review of the Effects of Particulate Matter Air Pollution on Human Health," Journal of Medical Toxicology, 2012, vol. 8, pp. 166-175.
Apaydin, Erica A. et al., "Asystematic review of St. John's wort for major depressive disorder," Systematic Reviews, 2016, vol. 5, No. 148 (25 pages).
Aries et al., "Daylight and health: A review of the evidence and consequences forthe built environment," Lighting Research & Technology, 2015, vol. 47, pp. 6-27.
Aries et al., "Windows, view, and office characteristics predict physical and psychological discomfort," Journal of Environmental Psychology, 2010, vol. 30, pp. 533-541.
Aries, "Human lighting demands: healthy lighting in an office environment," thesis, 2005 (159 pages).
Arrington et al., "Voluntary Task Switching: Chasing the Elusive Homunculus," Journal of Experimental Psychology: Learning, Memory, and Cognition, 2005, vol. 31, No. 4, pp. 683-702.
Arundel et al., "Indirect Health Effects of Relative Humidity in Indoor Environments," Environmental Health Perspectives, 1986, vol. 65, pp. 351-361.
Astolfi et al., "Subjective and objective assessment of acoustical and overall environmental quality in secondary school classrooms," The Journal of the Acoustical Society of America, 2008, vol. 123, No. 1, pp. 163-173.
Atmaca et al., "Effects of radiant temperature on thermal comfort," Building and Environment, 2007, vol. 42, pp. 3210-3220.
Atmaca et al., "Predicting the effect of relative humidity on skin temperature and skin wettedness," Journal of Thermal Biology, 2006, vol. 31, pp. 442-452.
Bakker et al., "User satisfaction and interaction with automated dynamic facades: a pilot study," Building and Environment, 2014, vol. 78, pp. 44-52.
Beauchemin et al., "Sunny hospital rooms expedite recovery from severe and refractory depressions," Journal of Affective Disorders, 1996, vol. 40, pp. 49-51.
Beaven et al., "A Comparison of Blue Light and Caffeine Effects on Cognitive Function and Alertness in Humans," PLoS One, 2013, vol. 8, No. 10 (7 pages).
Bekö et al., Ventilation rates in the bedrooms of 500 Danish children, Building and Environment, 2010, vol. 45, pp. 2289-2295.
Bell et al., "The Exposure—Response Curve for Ozone and Risk of Mortality and the Adequacy of Current Ozone Regulations," Environmental Health Perspectives, 2006, vol. 114, No. 4, pp. 532-536.
Bellicha, Alice et al., "A multistage controlled intervention to increase stair climbing at work: effectiveness and process evaluation," International Journal of Behavioral Nutrition and Physical Activity, 2016, vol. 13, No. 47, pp. 1-9 (9 pages).
Benedetti, "Morning sunlight reduces length of hospitalization in bipolar depression," Journal of Affective Disorders, 2001, vol. 62, pp. 221-223.
Berman et al., "The Cognitive Benefits of Interacting With Nature," Psychological Science, 2008, vol. 19, No. 12, pp. 1207-1212.
Berto, "Exposure to restorative environments helps restore attentional capacity," Journal of Environmental Psychology, 2005, vol. 25, pp. 249-259.

Berto, "The Role of Nature in Coping with Psycho-Physiological Stress: A Literature Review on Restorativeness," Behavioral Sciences, 2014, vol. 4, pp. 394-409.
Besner et al., "The Stroop effect and the myth of automaticity," Psychonomic Bulletin & Review, 1997, vol. 4, No. 2, pp. 221-225.
Bhutta, Zulfiqar A. et al., "Evidence-based interventions for improvement of maternal and child nutrition: what can be done and at what cost?," The Lancet, 2013, vol. 382, pp. 452-447.
Bidonde, J. et al., "Aerobic exercise training for adults with fibromyalgia (Review)," Cochrane Database of Systematic Reviews, 2017, Issue 6 (130 pages).
Bierman et al., "Characterizing Daylight Photosensor System Performance to Help Overcome Market Barriers," Journal of the Illuminating Engineering Society, 2000, vol. 29, No. 1, pp. 101-115.
Borisuit et al., "Effects of realistic office daylighting and electric lighting conditions on visual comfort, alertness and mood," Lighting Research and Technology, 2015, vol. 47, pp. 192-209.
Boubekri et al., "Impact of Windows and Daylight Exposure on Overall Health and Sleep Quality of Office Workers: A Case-Control Pilot Study," Journal of Clinical Sleep Medicine, 2014, vol. 10, No. 6, pp. 603-611.
Boubekri et al., "The Impact of Optimized Daylight and Views on the Sleep Duration and Cognitive Performance of Office Workers," International Journal of Environmental Research and Public Health, 2020, vol. 17, No. 3219, pp. 1-16.
Boubekri et al., "Windows and Environmental Satisfaction: A Survey Study of an Office Building," Indoor Environment, 1993, vol. 2, pp. 164-172.
Brager, Gail S., et al., "Thermal adaptation in the built environment: a literature review," Energy and Buildings, 1998, vol. 27, pp. 83-96 (15 pages).
Braniš et al., "The effect of outdoor air and indoor human activity on mass concentrations of PM10, PM2.5, and PM1 in a classroom," Environmental Research, 2005, vol. 99, pp. 143-149.
Brook et al., "Particulate Matter Air Pollution and Cardiovascular Disease: An Update to the Scientific Statement From the American Heart Association," Circulation: Journal of the American Heart Association, 2010, vol. 121, pp. 2331-2378.
Brown et al., "Interventions to Reduce Harm from Smoking with Families in Infancy and Early Childhood: A Systematic Review," International Journal of Environmental Research and Public Health, 2015, vol. 12, pp. 3091-3119 (29 pages).
Brown et al., "Recommendations for healthy daytime, evening, and night-time indoor light exposure," Preprints, 2020 (21 pages).
Brown, Nicola et al., "Interventions to Reduce Harm from Smoking with Families in Infancy and Early Childhood: A Systematic Review ," International Journal of Environmental Research and Public Health, 2015, vol. 12, pp. 3091-3119, (29 pages).
Buchanan et al., "Air filter materials, outdoor ozone and building-related symptoms in the BASE study," Indoor Air, 2008, vol. 18, pp. 144-155.
Burge et al., "Sick Building Syndrome: A Study of 4373 Office Workers," Annals of Occupational Hygiene, 1987, vol. 31, No. 4A, pp. 493-504.
Bussières, André E., et al., "The Treatment of Neck Pain—Associated Disorders and Whiplash-Associated Disorders: A Clinical Practice Guideline,"Journal of Manipulative and Physiological Therapeutics, 2016, vol. 39, No. 8, pp. 523-564.e27 (69 pages).
Butler et al., "Effects of Setting on Window Preferences And Factors Associated With Those Preferences," Environment and Behavior, 1989, vol. 21, No. 1, pp. 17-31.
Byrne, Daniel W. et al., "Seven-Year Trends in Employee Health Habits From a Comprehensive Workplace Health Promotion Program at Vanderbilt University," Journal of Occupational and Environmental Medicine, Dec. 2011, vol. 53, No. 12, pp. 1372-1381 (10 pages).
Cairncross, Sandy, et al., "Water, sanitation and hygiene forthe prevention of diarrhoea," International Journal of Epidemiology, 2010, vol. 39, pp. :i193-i205 (14 pages).
California Energy Commission, 2013 Building Energy Efficiency Standards for Residential and Nonresidential Buildings, CEC☐400☐2012☐004-CMF-REV2 (268 pages).

(56) References Cited

OTHER PUBLICATIONS

Campanella et al., "Well Living Lab: A New Tool for Measuring the Human Experience in the Built Environment," Conscious Cities Journal No. 2, Conscious Cities Anthology 2017: Bridging Neuroscience, Architecture and Technology, 2017 (5 pages).

Cao, Chunmei et al., "Effect of Active Workstation on Energy Expenditure and Job Performance: A Systematic Review and Meta-analysis," Journal of Physical Activity and Health, 2016, vol. 13, No. 5, pp. 562-571.

Carlucci, Salvatore et al., "A review of indices for assessing visual comfort with a view to their use in optimization processes to support building integrated design," Renewable and Sustainable Energy Reviews, 2015, vol. 47, pp. 1016-1033.

Carr et al., "Interventions for tobacco cessation in the dental setting (Review)," Cochrane Database of Systematic Reviews, 2012, Issue 6, pp. 1-38 (40 pages).

Carrer et al., "Assessment through Environmental and Biological Measurements of Total Daily Exposure to Volatile Organic Compounds of Office Workers in Milan, Italy," Indoor Air, 2000, vol. 10, pp. 258-268.

Center for Disease Control and Prevention, "Steps to Wellness: A Guide to Implementing the 2008 Physical Activity Guidelines for Americans in the Workplace" U.S. Department of Health Services, 2012, (120 pages).

Centers for Disease Control and Prevention, "Strategies to Prevent Obesity and Other Chronic Diseases: The CDC Guide to Strategies to Increase the Consumption of Fruits and Vegetables.," U.S. Department of Health and Human Services, 2011, pp. 1-60 (68 pages).

Chellappa et al., "Can light make US bright? Effects of light on cognition and sleep," Progress in Brain Research, 2011, vol. 190, 119-133.

Chellappa et al., "Non-Visual Effects of Light on Melatonin, Alertness and Cognitive Performance: Can Blue-Enriched Light Keep US Alert?," PLoS One, 2011, vol. 6, No. 1 (11 pages).

Chellappa et al., "Sex differences in light sensitivity impact on brightness perception, vigilant attention and sleep in humans," Scientific Reports, 2017, vol. 7, No. 14215, pp. 1-9.

Chellappa, "Individual differences in light sensitivity affect sleep and circadian rhythms," Sleep, 2021, vol. 44, No. 2, pp. 1-10.

Chen et al., "The Effect of Blue-Enriched Lighting on Medical Error Rate in a University Hospital ICU," The Joint Commission Journal on Quality and Patient Safety, 2021, vol. 47, No. 3, pp. 165-175.

Choi et al., "Impacts of indoor daylight environments on patient average length of stay (ALOS) in a healthcare facility," Building and Environment, 2012, vol. 50, pp. 65-75.

Chou, "A Practical Guide to Hazardous Gas Monitors" Occupational Hazards, 2000, vol. 62, No. 9, pp. 61-66.

Christoffersen et al., "Windows and Daylight'A post-occupancy evaluation of Danish offices," 2000 (9 pages).

Chun et al., "Thermal diary: Connecting temperature history to indoor comfort," Building and Environment, 2008, vol. 43, pp. 877-885.

Clasen et al., "Interventions to improve water quality for preventing diarrhoea (Review)," Cochrane Database of Systematic Reviews, 2015, Issue 10, pp. 1-175 (178 pages).

Clements-Croome, "Work performance, productivity and indoor air," Scandinavian Journal of Work Environment & Health, 2008, pp. 69-78.

Corbijn Van Willenswaard, Kyrsten et al., "Music interventions to reduce stress and anxiety in pregnancy: a systematic review and meta-analysis," BMC Psychiatry, 2017, vol. 17, No. 271, pp. 1-9 (9 pages).

Coury, Helenice J.C.G. et al., "Evaluation of the effectiveness of workplace exercise in controlling neck, shoulder and low back pain: a systematic review," Brazilian Journal of Physical Therapy, 2009, vo. 13, No. 6, pp. 461-479.

D'Ambrosio Alfano et al., "On the measurement of the mean radiant temperature and its influence on the indoor thermal environment assessment," Building and Environment, 2013, vol. 63, pp. 79-88.

Dalager et al., "Implementing intelligent physical exercise training at the workplace: health effects among office workers—a randomized controlled trial," European Journal of Applied Physiology, 2016, vol. 116, pp. 1433-1442 (10 pages).

Dalal, Reeshad S., "Job Attitudes: Cognition and Affect," Handbook of Psychology, Second Edition, 2013, pp. 341-366 (26 pages).

Darvesh, Nazia, et al., "Water, sanitation and hygiene interventions for acute childhood diarrhea: a systematic review to provide estimates forthe Lives Saved Tool," BMC Public Health, 2017, vol. 17(Suppl 4), Article 776, pp. 101-111 (11 pages).

De Dear et al., "Developing an Adaptive Model of Thermal Comfort and Preference," ASHRAE Transactions, 1998, vol. 104, part 1 (19 pages).

Destaillats et al., "Indoor pollutants emitted by office eguipment: A review of reported data and information needs," Atmospheric Environment, 2008, vol. 42, pp. 1371-1388.

Diamond, "Executive Functions," Annual Review of Psychology, 2013, vol. 64, pp. 135-168.

Dingle et al., "Formaldehyde Levels and the Factors Affecting These Levels in Homes in Perth, Western Australia," Indoor Built Environment, 2002, vol. 11, pp. 111-116.

Domanico et al., "Documenting the NICU design dilemma: comparative patient progress in openward and single family room units," Journal of Perinatology, 2011, vol. 31, pp. 281-288.

Dong et al., "A review of smart building sensing system for better indoor environment control," Energy and Buildings, 2019, vol. 199, pp. 29-46.

Dounis et al., "Design of a fuzzy system for living space thermal-comfort regulation," Applied Energy, 2001, vol. 69, pp. 119-144.

Duckitt, Kirsten et al., "Menorrhagia," BMJ Clinical Evidence, 2012, pp. 1-69 (69 pages).

Dussault et al., "Office buildings with electrochromic windows: A sensitivity analysis of design parameters on energy performance, and thermal and visual comfort," Energy and Building, 2017, vol. 153, pp. 50-62.

Ebbert et al., "Interventions for smokeless tobacco use cessation (Review)," Cochrane Database of Systematic Reviews, 2015, No. 10 (56 pages).

Eisele et al., "Led Lighting System," Office Action dated Oct. 22, 2015, for U.S. Appl. No. 14/805,243, 14 pages.

Eisele et al., "Led Lighting System," Second Preliminary Amendment filed Dec. 30, 2014, for U.S. Appl. No. 14/486,753, 9 pages.

Engvall et al., "Sick building syndrome in relation to building dampness in multi-family residential buildings in Stockholm," International Archives of Occupational and Environmental Health, 2001, vol. 74, pp. 270-278.

Epstein et al., "Thermal Comfort and the Heat Stress Indices," Industrial Health, 2006, vol. 44, pp. 388-398.

European Agency for Safety and Health at Work, et al., "Work-related musculoskeletal disorders: back to work report," Luxembourg: Office for Official Publications of the European Communities, 2007. pp. 3-100 (100 pages).

Examination Report issued in AU Application No. 2016202287 dated May 8, 2020.

Farzaneh et al., "Controlling automobile thermal comfort using optimized fuzzy controller," Applied Thermal Engineering, 2008, vol. 28, pp. 1906-1917.

Felleman et al., "Distributed Hierarchical Processing in the Primate Cerebral Cortex," Cerebral Corte, 1991, vol. 1, No. 1, pp. 1-47.

Ferguson MA et al., "Hearing aids for mild to moderate hearing loss in adults (Review)," Cochrane Database of Systematic Reviews, 2017, Issue 9, pp. 1-46 (48 pages).

Fewtrell, Lorna, et al., "Water, sanitation, and hygiene interventions to reduce diarrhoea in less developed countries: a systematic review and meta-analysis," The Lancet Infect Diseases, 2005, vol. 5, pp. 42-52 (11 pages).

Figueiro et al., "Daylight and Productivity—A Field Study," Panel 8. Human and Social Dimensions of Energy Use: Understanding Markets and Demand, 2002 (10 pages).

Finnegan et al., "Work Attitudes in Windowed vs. Windowless Environments," The Journal of Social Psychology, 1981, vol. 115, pp. 291-292.

(56) References Cited

OTHER PUBLICATIONS

Fisk et al., "Age-Related Impairment in Executive Functioning: Updating, Inhibition, Shifting, and Access," Journal of Clinical and Experimental Neuropsychology, 2004, vol. 26, No. 7, pp. 874-890.
Fisk, "Estimates of Potential Nationwide Productivity and Health Benefits From Better Indoor Environments: An Update," Indoor Air Quality Handbook, 1999 (38 pages).
Fisk, William J. et al., "Estimates of Potential Nationwide Productivity and Health Benefits From Better Indoor Environments: An Update," 1999 (38 pages).
Fisk, William, "How IEQ Affects Health, Productivity," ASHRAE Journal, 2002, vol. 44, No. 5, pp. 56-60 (4 pages).
Föbldváry et al., "Effect of energy renovation on indoor air quality in multifamily residential buildings in Slovakia," Building and Environment, 2017, vol. 122, pp. 363-372.
Food Service Guidelines Federal Workgroup, "Food Service Guidelines for Federal Facilities," 2017, U.S. Department of Health and Human Services, Washington, DC (30 pages).
Foster et al., "Shortened complex span tasks can reliably measure working memory capacity," Memory & Cognition, 2015, vol. 43, pp. 226-236.
Foster, "Fundamentals of circadian entrainment by light," Lighting Research & Technology, 2021, vol. 53, pp. 377-393.
Frazer K et al., "Impact of institutional smoking bans on reducing harms and secondhand smoke exposure (Review)," Cochrane Database of Systematic Reviews, 2016, Issue 5, pp. 1-85 (87 pages).
Frazer, K et al., "Legislative smoking bans for reducing harms from secondhand smoke exposure, smoking prevalence and tobacco consumption (Review)," Cochrane Database of Systematic Reviews, 2016, Issue 2, pp. 1-192 (194 pages).
Frontczak et al., "Literature survey on how different factors influence human comfort in indoor environments," Building and Environment, 2011, vol. 46, pp. 922-937.
Frontczak, Monika et al., "Literature survey on how different factors influence human comfort in indoor environments," Building and Environment, vol. 46, 2011, pp. 922-937 (16 pages).
Galasiu et al., "Occupant preferences and satisfaction with the luminous environment and control systems in daylit offices: a literature review," Energy and Buildings, 2006, vol. 38, pp. 728-742.
Garn, Joshua V., et al., "The impact of sanitation interventions on latrine coverage and latrine use: A systematic review and meta-analysis," International Journal of Hygiene and Environmental Health, 2017, vol. 220, pp. 329-340 (12 pages).
GBD 2013 Risk Factors Collaborators, "Global, regional, and national comparative risk assessment of 79 behavioural, environmental and occupational, and metabolic risks or clusters of risks in 188 countries, 1990-2013: a systematic analysis for the Global Burden of Disease Study 2013," The Lancet, 2015, vol. 386, pp. 2287-2323.
GBD 2016 Risk Factors Collaborators, "Global, regional, and national comparative risk assessment of 84 behavioural, environmental and occupational, and metabolic risks or clusters of risks, 1990-2016: a systematic analysis forthe Global Burden of Disease Study 2016," The Lancet, 2017, vol. 390, pp. 1345-1422 (78 pages).
Geaney, F., et al., "The effectiveness of workplace dietary modification interventions: Asystematic review," Preventive Medicine, 2013, vol. 57, pp. 438-447, 10 pages.
General Services Administration, "Sound Matters: How to achieve accoustic comfort in the contemporary office," 2011, pp. 1-42 (42 pages).
Goodman, "Measurement and specification of lighting: A look at the future," Lighting Research and Technology, 2009, vol. 41, pp. 229-243.
Goodnough, L.T. et al., "Detection, evaluation, and management of preoperative anaemia in the elective orthopaedic surgical patient: NATA guidelines," British Journal of Anaesthesia, 2011, vol. 106, No. 1, pp. 13-22.
Grant et al., "Daytime Exposure to Short Wavelength-Enriched Light Improves Cognitive Performance in Sleep-Restricted College-Aged Adults," Frontier in Neurology, 2021, vol. 12, pp. 1-10.
Graves, Lee E.F. et al., "Evaluation of sit-stand workstations in an office setting: a randomised controlled trial," BMC Public Health, 2015, vol. 15, No. 1145 (14 pages).
Gueymard, "Turbidity Determination from Broadband Irradiance Measurements: A Detailed Multicoefficient Approach," Journal of Applied Meteorology, 1998, vol. 37, pp. 414-435.
Guirao, "Average Optical Performance of the Human Eye as a Function of Age in a Normal Population," Investigative Ophthalmology & Visual Science, 1999, vol. 40, No. 1, pp. 203-213.
Guyatt et al., "GRADE: an emerging consensus on rating quality of evidence and strength of recommendations," BMJ, Apr. 26, 2008, vol. 336, pp. 924-926 (3 pages).
Haider, B.A. et al., "Anaemia, prenatal iron use, and risk of adverse pregnancy outcomes: systematic review and meta-analysis," BMJ, 2013, pp. 1-19.
Haider, BA et al., "Multiple-micronutrient supplementation for women during pregnancy (Review)," Cochrane Database of Systematic Reviews, 2015, Issue 11, pp. 1-100 (103 pages).
Hajdukiewicz, Magdalena et al., "Calibrated CFD simulation to evaluate thermal comfort in a highly-glazed naturally ventilated room," Building and Environment, 2013, vol. 70, pp. 73-89.
Hajdukiewicz, Magdalena et al., "Formal calibration methodology for CFD models of naturally ventilated indoor environments," Building and Environment, 2012, vol. 59 (28 pages).
Hannibal et al., "Melanopsin Is Expressed in PACAP-Containing Retinal Ganglion Cells of the Human Retinohypothalamic Tract," Investigative Ophthalmology & Visual Science, 2004, vol. 45, No. 11, pp. 4202-4209.
Haq et al., "A review on lighting control technologies in commercial buildings, their performance and affecting factors," Renewable and Sustainable Energy Reviews, 2014, vol. 33, pp. 268-279.
Hasan et al., "Sensitivity study forthe PMV thermal comfort model and the use of wearable devices biometric data for metabolic rate estimation," Building and Environment, 2016, vol. 110, pp. 173-183.
Hasan, Mohammad H., et al. "Sensitivity study forthe PMV thermal comfort model and the use of wearable devices biometric data for metabolic rate estimation," Building and Environment, 2016, vol. 110, pp. 173-183 (11 pages).
Heijnen, Marieke et al., "Shared Sanitation versus Individual Household Latrines: A Systematic Review of Health Outcomes," PLoS ONE, 2014, vol. 9, Issue 4, pp. 1-9 (9 pages).
Hensen, "Literature Review on Thermal Comfort in Transient Conditions," Building and Environment, 1990, vol. 25, No. 4, pp. 309-316.
Higuchi et al., "Influence of eye colors of Caucasians and Asians on suppression of melatonin secretion by light," American Journal of Physiology: Regulatory, Integrative and Comparative Physiology, 2007, vol. 292, pp. R2352-R2356.
Hiscocks, "Measuring Light," 2008 (9 pages).
Hiscocks, "Measuring Luminance with a Digital Camera: Case History," 2013 (10 pages).
Hoisington et al., "Ten questions concerning the built environment and mental health," Building and Environment, 2019, vol. 155, pp. 58-69.
Horne et al., "A Self-Assessment Questionnaire to Determine Morningness-Eveningness in Human Circadian Rhythms," International Journal of Chronobiology, 1976, vol. 4, pp. 97-110.
Hossain, Muttaquina et al., "Evidence-based approaches to childhood stunting in low and middle income countries: a systematic review," Archives of Disease in Childhood, 2017, vol. 102, pp. 903-909.
Hou, Can et al., "Do Mobile Phone Applications Improve Glycemic Control (HbA1c) in the Self-management of Diabetes? A Systematic Review, Meta-analysis, and GRADE of 14 Randomized Trials," Diabetes Care, 2016, vol. 39, pp. 2089-2095.
Howieson et al., "Building tight—ventilating right? How are new air tightness standards affecting indoor air quality in dwellings?" Journal of Building Services Engineering Research & Technology, 2014, vol. 35, No. 5, pp. 475-487.

(56) References Cited

OTHER PUBLICATIONS

Huang et al., "A study about the demand for air movement in warm environment," Building and Environment, 2013, vol. 61, pp. 27-33.
Huizenga et al., "Air Quality and Thermal Comfort in Office Buildings: Results of a Large Indoor Environmental Quality Survey," Proceedings of Healthy Buildings, 2006, vol. 3, pp. 393-397.
Huizenga, C. et al., "Air Quality and Thermal Comfort in Office Buildings: Results of a Large Indoor Environmental Quality Survey," Proceeding of Healthy Buildings, 2006, vol. 3 (6 pages).
Humphreys, "Quantifying occupant comfort: are combined indices of the indoor environment practicable?" Building Research & Information, 2005, vol. 33, No. 4, pp. 317-325.
Huo, Jun Sheng et al., "Effect of NaFeEDTA-Fortified Soy Sauce on Anemia Prevalence in China: A Systematic Review and Meta-analysis of Randomized Controlled Trials," Biomedical and Environmental Science, 2015, vol. 28, No. 11, pp. 788-798.
Hutchinson, et al. "Improving nutrition and physical activity in the workplace: a meta-analysis of intervention studies," Health Promotion International, 2012, vol. 27, No. 2, pp. 238-249 (12 pages).
International Commission on Illumination, Technical Report: Guide on the Limitation of the Effects of Obtrusive Light From outdoor Lighting Installations, 2003 (46 pages).
International Organization for Standardization, "Ergonomics of the thermal environment—Instruments for measuring physical quantities," BS EN ISO 7726, 2nd Edition, 2001 (62 pages).
International Organization for Standardization, "Ergonomics of the thermal environment—Analytical determination and interpretation of thermal comfort using calculation of the PMV and PPD indices and local thermal comfort criteria," ISO 7730, 3rd Edition, 2005 (11 pages).
International Search Report and Written Opinion for PCT/US2022/020903, dated Jul. 12, 2022 (17 pages).
International Search Report for International Application No. PCT/US2019/050339, dated Nov. 27, 2019 (2 pages).
International Search Report for PCT/JUS2020/019697, dated Jul. 14, 2020 (4 pages).
International Search Report for PCT/US2018/048853 dated Nov. 21, 2018.
International Search Report issued in International Application No. PCT/US2019/50416, dated Nov. 27, 2019, 1 p.
International Well Building Institute, "The WELL Building Standard: Version 1.0," 2015 (220 pages).
Ishihara et al., "Metabolic responses to polychromatic LED and OLED light at night," Scientific Reports, 2021, vol. 11, pp. 1-11.
Jamrozik et al., "A novel methodology to realistically monitor office occupant reactions and environmental conditions using a living lab," Building and Environment, 2018, vol. 130, pp. 190-199.
Jenkins et al., "A practical approach to glare assessment for train cabs," Applied Ergonomics, 2015, vol. 47, pp. 170-180.
Job Accommodation Network, "Accommodation and Compliance Series: Employees with Hearing Loss," available at https://askjan.org/media/Hearing.html, accessed Oct. 31, 2017 (25 pages).
Jonsson, Ulf et al., "Psychological Treatment of Depression in People Aged 65 Years and Over: A Systematic Review of Efficacy, Safety, and Cost Effectiveness," PLoS ONE, 2016, vol. 11, No. 8, pp. 1-20 (20 pages).
Kahn-Marshall, Jennifer L. et al., "Making Healthy Behaviors the Easy Choice for Employees: A Review of the Literature on Environmental and Policy Changes in Worksite Health Promotion," Health Education & Behavior, 2012, vol. 39, No. 6, pp. 752-776, (25 pages).
Kakde, S. et al., "Asystematic review on the social context of smokeless tobacco use in the South Asian population: Implications for public health," Public Health, 2012, vol. 126, No. 8, pp. 635-645.
Kaplan et al., "Directed Attention as a Common Resource for Executive Functioning and Self-Regulation," Perspectives on Psychological Science, 2010, vol. 5, No. 1, pp. 43-57.
Kaplan, "The Restorative Benefits of Nature: Toward an Integrative Framework," Journal of Environmental Psychology, 1995, vol. 15, pp. 169-182.
Karjalainen et al., "User problems with individual temperature control in offices," Building and Environment, 2007, vol. 42, pp. 2880-2887.
Karjalainen, "Thermal comfort and gender: a literature review," Indoor Air, 2012, vol. 22, pp. 96-109.
Kennedy et al., "Smoke-Free Policies in U.S. Prisons and Jails: AReview of the Literature," (Author Manuscript) Nicotine & Tobacco Research, 2015, vol. 17, No. 6 (14 pages).
Khunti, Kamlesh et al., "Association Between Adherence to Pharmacotherapy and Outcomes in Type 2 Diabetes: A Meta-analysis," Diabetes Care, 2017, vol. 40, pp. 1588-1596.
Kinney, "Climate Change, Air Quality, and Human Health," American Journal of Preventive Medicine, 2008, vol. 35, No. 5, pp. 459-467.
Klepeis et al., "The National Human Activity Pattern Survey (NHAPS): a resource for assessing exposure to environmental pollutants," Journal of Exposure Analysis and Environmental Epidemiology, 2001, vol. 11, No. 3, pp. 231-252.
Knai, Cécile C. et al., "Are the Public Health Responsibility Deal alcohol pledges likely to improve public health? An evidence synthesis," Addiction, 2015, vol. 110, No. 8 (29 pages).
Knudsen et al., "Sensory and chemical characterization of VOC emissions from building products: impact of concentration and air velocity," Atmospheric Environment, 1999, vol. 33, pp. 1217-1230.
Kong et al., "The impact of interior design on visual discomfort reduction: A field study integrating lighting environments with POE survey," Building and Environment, 2018, vol. 138, pp. 135-148.
Konstantzos et al., "The effect of lighting environment on task performance in buildings—A review," Energy & Buildings, 2020, vol. 226, pp. 1-14.
Kool et al., "Decision Making and the Avoidance of Cognitive Demand," Journal of Experimental Psychology: General, 2010, vol. 139, No. 4, pp. 665-682.
Korotcenkov et al., "$In_2O_3$- and $SnO_2$-Based Thin Film Ozone Sensors: Fundamentals," Journal of Sensors, 2016, vol. 2016 (32 pages).
Kota, Sandeep et al., "Historical Survey of Daylighting Calculations Methods and Their Use in Energy Performance Simulations," Proceedings of the Ninth International Conference for Enhanced Building Operations, Nov. 17-19, 2009, Austin, Texas (9 pages).
Lacaille et al., "Go!: results from a quasi-experimental obesity prevention trial with hospital employees," BMC Public Health, 2016, vol. 17, No. 171, pp. 1-16 (16 pages).
Lai et al., "An evaluation model for indoor environmental quality (IEQ) acceptance in residential buildings," Energy and Buildings, 2009, vol. 41, pp. 930-936.
Lai et al., "Perceived Importance of the Quality of the Indoor Environment in Commercial Buildings," Indoor and Built Environment, 2007, vol. 16, No. 4, pp. 311-321.
Lai et al., "Perception of importance and performance of the indoor environmental quality of high-rise residential buildings," Building and Environment, 2009, vol. 44, pp. 352-360.
Lal, Avtar, et al., "The Effect of Physical Exercise After a Concussion: A Systematic Review and Meta-analysis," The American Journal of Sports Medicine, 2018, vol. 43, Issue 3, pp. 743-752 (10 pages).
Landrigan, Phillip J., "Air pollution and health," The Lancet Public Health, 2017, vol. 2, No. 1, pp. e4-e5.
Larson, Nicole et al., "A Review of Environmental Influences on Food Choices," Annals of Behavioral Medicine : A Publication of the Society of Behavioral Medicine, 2009, vol. 38 Suppl 1, pp. S56-S73.
Lassi et al., "Impact of education and provision of complementary feeding on growth and morbidity in children less than 2 years of age in developing countries: a systematic review," BMC Public Health, 2013, vol. 13, pp. 1-10 (10 pages).
Leather et al., "Windows in the Workplace: Sunlight, View, and Occupational Stress," Environment and Behavior, 1998, vol. 30, No. 6, pp. 739-762.

(56) References Cited

OTHER PUBLICATIONS

Leder et al., "Effects of office environment on employee satisfaction: a new analysis," Building Research and Information, 2015 (22 pages).
Lee, Courtney, et al., "The effectiveness of acupuncture research across components of the trauma spectrum response (tsr): a systematic review of reviews," Systematic Reviews, 2012, vol. 1, Article 46, pp. 1-18 (18 pages).
Leech et al., "It's about time: A comparison of Canadian and American time-activity patterns," Journal of Exposure Analysis and Environmental Epidemiology, 2002, vol. 12, No. 6, pp. 427-432.
Leidinger et al., "Selective detection of hazardous VOCs for indoor air guality applications using a virtual gas sensor array," Journal of Sensors and Sensor Systems, 2014, vol. 3, pp. 253-263.
Levy et al., "Ozone Exposure and Mortality: An Empiric Bayes Metaregression Analysis," Epidemiology, 2005, vol. 16, No. 4, pp. 458-468.
Lewtas, "Air pollution combustion emissions: Characterization of causative agents and mechanisms associated with cancer, reproductive, and cardiovascular effects," Reviews in Mutation Research, 2007, vol. 636, pp. 95-133.
Li et al., "Health promotion interventions and policies addressing excessive alcohol use: Asystematic review of national and global evidence as a guide to health-care reform in China," HHS Public Access, Author Manuscript, 2015, vol. 110, No. 1, pp. 1-18 (18 pages).
Licht.wissen 19: Impact of Light on Human Beings, licht.de, Mar. 2014 (56 pages).
Licina et al., "Concentrations and Sources of Airborne Particles in a Neonatal Intensive Care Unit," PLOS One, 2016 (17 pages).
Licina et al., "Emission rates and the personal cloud effect associated with particle release from the perihuman environment," Indoor Air, 2017, vol. 27, pp. 791-802.
Liu et al.," Human thermal adaptive behaviour in naturally ventilated offices for different outdoor air temperatures: A case study in Changsha China," Building and Environment, 2012, vol. 50, pp. 76-89.
Liu et al., "A Survey on Gas Sensing Technology," Sensors, 2012, vol. 12, pp. 9635-9665.
Löndahl et al., "A set-up for field studies of respiratory tract deposition of fine and ultrafine particles in humans," Journal of Aerosol Science, 2006, vol. 37, pp. 1152-1163.
Luedtke, Kerstin et al., "Efficacy of interventions used by physiotherapists for patients with headache and migraine—Systematic review and meta-analysis," Cephalalgia, 2015 (20 pages).
Luke, "Evaluating significance in linear mixed-effects models in R," Behavior Research Methods, 2017, vol. 49, pp. 1494-1502.
Luttmann, Alwin et al., "Preventing Musculoskeletal Disorders in the Workplace," World Health Organization, Protecting Workers' Health Series No. 5, 2003 (40 pages).
Macarthur, Georgie J. et al., "Peer-led interventions to prevent tobacco, alcohol and/or drug use among young people aged 11-21 years: a systematic review and meta-analysis," 2016, Addiction, vol. 111, pp. 391-407 (17 pages).
Maes, Lea et al., "Effectiveness of workplace interventions in Europe promoting healthy eating: a systematic review," European Journal of Public Health, 2012, vol. 22, No. 5, pp. 677-683.
Mahyuddin et al., "The spatial distribution of carbon dioxide in rooms with particular application to classrooms," Indoorand Built Environment, 2014, vol. 23, No. 3, pp. 433-448.
Markus, "The Function of Windows—A Reappraisal," Building Science, 1967, vol. 2, pp. 97-121.
Massey et al., "Emission and Formation of Fine Particles from Hardcopy Devices: the Cause of Indoor Air Pollution," Monitoring, Control and Effects of Air Pollution, 2001, pp. 121-134.
McCullough et al., "Determining temperature ratings for children's cold weather clothing," Applied Ergonomics, 2009, vol. 40, pp. 870-877.
McIntyre, "Response to Atmospheric Humidity at Comfortable Air Temperature: A Comparison of Three Experiments," Annals of Occupational Hygiene, 1978, vol. 21, pp. 177-190.
McKay, Alisa J. et al,, "Strategies for Tobacco Control in India: A Systematic Review," PLOS One, 2015, vol. 4. pp 1-34 (34 pages).
Meerbeek et al., "Impact of blinds usage on energy consumption: automatic versus manual control," conference paper, 2014 (17 pages).
Meister et al., "Low-Level Visual Processing: The Retina," Chapter 26, Principles of Neural Science, 2014, pp. 577-601.
Mendell et al., "Improving the Health of Workers in Indoor Environments: Priority Research Needs for a National Occupational Research Agenda," American Journal of Public Health, 2002, vol. 92, No. 9, pp. 1430-1440.
Mendell, et al. "Improving the Health of Workers in Indoor Environments: Priority Research Needs for a National Occupational Research Agenda," American Journal of Public Health, 2002, vol. 92, No. 9, pp. 1430-1440 (11 pages).
Merz, Victoire et al., "Brief interventions to prevent recurrence and alcohol-related problems in young adults admitted to the emergency ward following an alcohol-related event: a systematic review," Journal of Epidemiology and Community Health, 2015, vol. 69, No. 9, pp. 912-917.
Minichiello, Alexa et al., "Effective strategies to reduce commercial tobacco use in Indigenous communities globally: Asystematic review," BMC Public Health, 2016, vol. 16, No. 21 (25 pages).
Mitchell, Lana J. et al., "Effectiveness of dietetic consultations in primary health care: A systematic review of randomized controlled trials," Journal of the Academy of Nutrition and Dietetics, 2017 (41 pages).
Miyake et al., "The Unity and Diversity of Executive Functions and Their Contributions to Complex "Frontal Lobe" Tasks: A Latent Variable Analysis," Cognitive Psychology, 2000, vol. 41, pp. 49-100.
Monson, Eva et al., "Effects of Enactment of Legislative (Public) Smoking Bans on Voluntary Home Smoking Restrictions: A Review," Nicotine &Tobacco Research, 2017, vol. 19, No. 2, pp. 141-148.
Moore-Ede et al., "Circadian Potency Spectrum with Extended Exposure to Polychromatic White LED Light under Workplace Conditions," Journal of Biological Rhythms, 2020, vol. 35, No. 4, pp. 405-415.
Moore-Ede et al., "LEDs must spectrally balance illumination, circadian health, productivity, and energy efficiency," LEDs Magazine, available at least as early as Aug. 2021 at https://www.ledsmagazine.com/lighting-health-wellbeing/article/14199941/ideal-led-lighting-must-balance-multiple-objectives-magazine (14 pages).
Myhren, Jonn Are et al., "Flow patterns and thermal comfort in a room with panel, floor and wall heating," Energy and Buildings, 2008, vol. 40, 524-536.
Nabil et al., "Useful daylight illuminances: A replacement for daylight factors," Energy and Buildings, 2006, vol. 38, pp. 905-913.
Nair, Natasha K. et al., "A Systematic Review of Digital and Computer-Based Alcohol Intervention Programs in Primary Care," Current Drug Abuse Reviews, 2015, vol. 8, No. 2, pp. 1-8.
National Center for Chronic Disease Prevention and Health Promotion, Division for Heart Disease and Stroke Prevention, "Under Pressure: Strategies for Sodium Reduction in Worksites ," Centers for Disease Control and Prevention, 2012, pp. 1-9 (12 pages).
National Lighting Product Information Program, "Photosensors: Dimming and Switching Systems for Daylight Harvesting," Specifier Reports, 2007, vol. 11, No. 1 (54 pages).
Ne'eman et al., "Office Worker Response to Lighting and Daylighting Issues in Workspace Environments: A Pilot Survey," Energy and Buildings, 1984, vol. 6, pp. 159-171.
Newsham, "Clothing as a thermal comfort moderator and the effect on energy consumption," Energy and Buildings, 1997, vol. 26, pp. 283-291.
Ni Mhurchu, Cliona et al., "Effects of worksite health promotion interventions on employee diets: a systematic review," BMC Public Health, 2010, vol. 10, No. 62, (7 pages).
Nicol et al., "A critique of European Standard EN 15251: strengths, weaknesses and lessons for future standards," Building Research & Information, 2011, vol. 39, No. 2, pp. 183-193.

(56) References Cited

OTHER PUBLICATIONS

Nie et al., "The effects of dynamic daylight☐ liklig ht on the rhythm, cognition, and mood of irregular shift workers in closed environment," Scientific Reports, 2021, vol. 11, No. 13059, pp. 1-11.
Nieuwenhuijsen, K. et al., "Interventions to improve return to work in depressed people (Review)," The Cochrane Library, 2014, Issue 12, pp. 1-140 (143 pages).
Ning, Mao et al., "Experimental and numerical studies on the performance evaluation of a bed-based task/ambient air conditioning (TAC) system," Applied Sciences, 2014, vol. 136, pp. 956-967.
Novoselac et al., "A critical review on the performance and design of combined cooled ceiling and displacement ventilation systems," Energy and Buildings, 2002, vol. 34, pp. 497-509.
O'Brien et al., "Manually-operated window shade patterns in office buildings: A critical review," Building and Environment, 2013, vol. 60, pp. 319-338.
Office Action issued in CN Application No. 201680009629.X dated Jul. 23, 2020.
Ormandy et al., "Health and thermal comfort: From WHO guidance to housing strategies," Energy Policy, 2012, vol. 49, pp. 116-121 (6 pages).
Osilla, Karen Chan, et al., "Systematic review of the Impact of Worksite Wellness Programs," The American Journal of Managed Care, 2012, vol. 18, No. 2, pp. e68-e81, (14 pages).
Pachón, Helena et al., "Evidence of the effectiveness of flour fortification programs on iron status and anemia: a systematic review," Nutrition Reviews, 2015, vol. 73, No. 11, pp. 780-795.
Painter et al., "Practical application of a sensor overlay system for building monitoring and commissioning," Energy and Buildings, 2012, vol. 48, pp. 29-39.
Panda et al., "Coordinated Transcription of Key Pathways in the Mouse by the Circadian Clock," Cell, 2002, vol. 109, pp. 307-320.
Park et al., "Variations of formaldehyde and VOC levels during 3 years in new and older homes," Indoor Air, 2006, vol. 16, pp. 129-135.
Park, "Are Humans Good Sensors? Using Occupants as Sensors for Indoor Environmental Quality Assessment and for Developing Thresholds that Matter," thesis, 2015 (274 pages).
Pasricha, Sant-Ryan et al., "Effect of daily iron supplementation on health in children aged 4-23 months: a systematic review and meta-analysis of randomised controlled trials," The Lancet Global Health, 2013, vol. 1, pp. e77-e86.
Passey, Megan E et al., "Smoke-free homes: what are the barriers, motivators and enablers? A qualitative systematic review and thematic synthesis," BMJ Open, 2016, vol. 6, pp. 1-16 (16 pages).
Pasut, Wilmer et al., "Energy-efficient comfort with a heated/cooled chair: Results from human subject tests," Building and Environment, 2015, vol. 84, pp. 10-21.
Peña-Rosas et al. "Intermittent oral iron supplementation during pregnancy (Review)," Cochrane Database of Systematic Reviews, 2015, Issue 10, pp. 1-186 (193 pages).
Perez et al., "All-Weather Model For Sky Luminance Distribution-Preliminary Configuration and Validation," Solar Energy, 1993, vol. 50, No. 3, pp. 235-245.
Persily, "Evaluating Building IAQ and Ventilation with Indoor Carbon Dioxide," ASHRAE Transactions, 1997, vol. 103 (12 pages).
Phillips et al., "High sensitivity and interindividual variability in the response of the human circadian system to evening light," Proceedings of the National Academy of Sciences of the United States of America, 2019, vol. 116, No. 24, pp. 12019-12024.
Phipps-Nelson et al., "Daytime Exposure to Bright Light, as Compared to Dim Light, Decreases Sleepiness and Improves Psychomotor Vigilance Performance," Sleep, 2003, vol. 26, No. 6, pp. 695-700.
Piccolo et al., "Effect of switchable glazing on discomfort glare from windows," Building and Environment, 2009, vol. 44, pp. 1171-1180.
Plotnikoff, Ronald et al., "Effectiveness of Interventions Targeting Health Behaviors in University and College Staff: A Systematic Review," American Journal of Health Promotion, 2015, vol. 29, No. 5 (20 pages).
Preto et al., "Lighting in the Workplace: Recommended Illuminance (lux) at Workplace Environs," Advances in Design for Inclusion, 2019, pp. 180-191.
Provencio et al., "A Novel Human Opsin in the Inner Retina," The Journal of Neuroscience, 2000, vol. 20, No. 2, pp. 600-605.
Prudhon, Claudine et al., "WHO, UNICEF, and SCN Informal Consultation on Community-Based Management of Severe Malnutrition in Children," SCN Nutrition Policy Paper No. 21, Food and Nutrition Bulletin, 2006, vol. 27, No. 3 (supplement), The United Nations University, pp. s3-s108 (108 pages).
Rea, "Window Blind Occlusion: a Pilot Study," Building and Environment, 1984, vol. 19, No. 2, pp. 133-137.
Reinhart et al., "Monitoring manual control of electric lighting and blinds," Lighting Research & Technology, 2003, vol. 35, No. 3, pp. 243-260.
Revel et al., "Integration of real-time metabolic rate measurement in a low-cost tool for the thermal comfort monitoring in AAL environments," Ambient Assisted Living, 2015 (11 pages).
Roberge et al., Operational Amplifiers: Theory and Practice, Second Edition, 2007 (104 pages).
Romm et al., Greening the Building and the Bottom Line: Increasing Productivity Through Energy-Efficient Design, 1994 (17 pages).
Rosen, Laura J. et al., "Effectiveness of Interventions to Reduce Tobacco Smoke Pollution in Homes: A Systematic Review and Meta-Analysis," International Journal of Environmental Research and Public Health, 2015, vol. 12, pp. 16043-16059.
Rubin et al., "Window Blinds as a Potential Energy Saver—A Case Study," National Bureau of Standards Building Science Series 112, 1978 (89 pages).
Saini et al., "The Mammalian Circadian Timing System: Synchronization of Peripheral Clocks," Cold Spring Harbor Symposia on Quantitative Biology, 2011, vol. 76 (10 pages).
Salthammer et al. "Formaldehyde in the Indoor Environment," Chemical Reviews, 2010, vol. 110, No. 4, pp. 2536-2572.
Sandberg et al., "Experimental Methods in Ventilation," Advances in Building Energy Research, 2008, vol. 2, No. 1, pp. 159-210.
Sarigiannis et al., "Multi-objective optimization of air quality monitoring," Environmental Monitoring Assessment, 2008, vol. 136, pp. 87-99.
Satish et al., "Is $CO_2$ an Indoor Pollutant? Direct Effects of Low-to-Mode rate $CO_2$ Concentrations on Human Decision-Making Performance," Environmental Health Perspectives, 2012, vol. 120, No. 12, pp. 1671-1677.
Sbar et al., "Electrochromic dynamic windows for office buildings," International Journal of Sustainable Built Environment, 2012, vol. 1, pp. 125-139.
Schellen et al., "Differences between young adults and elderly in thermal comfort, productivity, and thermal physiology in response to a moderate temperature drift and a steady-state condition," Indoor Air, 2010, vol. 20, pp. 273-283.
Schlegel, "The Relative Effects of Convection and Radiation Heat Transfer on the Thermal Sensations of Sedentary Subjects," 1968 (73 pages).
Schröer, S. et al., "Evidence-based lifestyle interventions in the workplace—an overview," Occupational Medicine, 2014, vol. 64, pp. 8-12.
Schweizer et al., "Indoor time—microenvironment—activity patterns in seven regions of Europe," Journal of Exposure Analysis and Environmental Epidemiology, 2007, vol. 17, No. 2, pp. 170-181.
Semenova et al., "Association of the melatonin circadian rhythms with clock 3111T/C gene polymorphism in Caucasian and Asian menopausal women with insomnia," Chronobiology International, 2018 (12 pages).
Seppänen et al., "Association of Ventilation Rates and $CO_2$ Concentrations with Health and Other Responses in Commercial and Institutional Buildings," Indoor Air, 1999, vol. 9, pp. 226-252.
Seppänen et al., "Summary of human responses to ventilation," Indoor Air, 2004, vol. 14, pp. 102-118.

(56) References Cited

OTHER PUBLICATIONS

Seppänen, O.A., et al., "Summary of human responses to ventilation," Indoor Air, 2004, vol. 14, Suppl. 7, pp. 102-118 (17 pages).
Shearer, Jane et al., "Nutra-ergonomics: influence of nutrition on physical employment standards and the health of workers," Applied Physiology, Nutrition, and Metabolism, 2016, vol. 41, pp. S165-S174 (10 pages).
Siemens, "Demand-controlled ventilation: Control strategy and applications for energy-efficient operation," publicly available at least as early as May 21, 2018 (72 pages).
Smith-Mclallen, Aaron et al., "Comparative Effectiveness of Two Walking Interventions on Participation, Step Counts, and Health," American Journal of Health Promotion, 2016 (9 pages).
Smith, GA et al., "Oral or parenteral iron supplementation to reduce deferral, iron deficiency and/or anaemia in blood donors (Review)," Cochrane Database of Systematic Reviews, 2014, Issue 7, pp. 1-120 (124 pages).
Song, "Could sperm quality be affected by a building environment? A literature review," Building and Environment, 2010, vol. 45, pp. 936-943.
Sorensen, Glorian, et al., "Worksite-based research and initiatives to increase fruit and vegetable consumption," Preventive Medicine, 2004, vol. 39, pp. S94-S100 (7 pages).
Spinellis, "The information furnace: consolidated home control," Personal and Ubiquitous Computing, 2003, vol. 7, pp. 53-69.
Storch et al., "Extensive and divergent circadian gene expression in liver and heart," Nature, 2002, vol. 417 (8 pages).
Strauss et al., "Influence of Heat and Humidity on the Airway Obstruction Induced by Exercise in Asthma," The Journal of Clinical Investigation, 1978, vol. 61, pp. 433-440.
Sunde et al., "Blue-Enriched White Light Improves Performance but Not Subjective Alertness and Circadian Adaptation During Three Consecutive Simulated Night Shifts," Frontiers in Psychology, 2020, vol. 11, No. 2172, pp. 1-16.
Sutter et al., "The use of shading systems in VDU task offices: A pilot study," Energy and Buildings, 2006, vol. 38, pp. 780-789.
Swaminathan et al., "Are Individual Differences in Sleep and Circadian Timing Amplified by Use of Artificial Light Sources?," Journal of Biological Rhythms, 2017, vol. 32, No. 2, pp. 165-176.
Szigeti et al., "Spatial and temporal variation of particulate matter characteristics within office buildings—The OFFICAIR study," Science of the Total Environment, 2017, vol. 587-588, pp. 59-67.
Tähkämö et al., "Systematic review of light exposure impact on human circadian rhythm," Chronobiology International: The Journal of Biological and Medical Rhythm Research, 2019, vol. 36, No. 2, pp. 151-170.
Tan, Ai May et al., "Efficacy of a workplace osteoporosis prevention intervention: a cluster randomized trial," BMC Public Health, 2016, vol. 16, No. 859 (14 pages).
Tansil, Kristin A. et al., "Alcohol Electronic Screening and Brief Intervention: A Community Guide Systematic Review," American Journal of Preventative Medicine Author Manuscript, 2016 (19 pages).
Taylor et al., "Impact of Booster Breaks and Computer Prompts on Physical Activity and Sedentary Behavior Among Desk-Based Workers: A Cluster-Randomized Controlled Trial," Preventing Chonic Disease Public Health Research, Practice, and Policy, Centers for Disease Control and Prevention, Nov. 2016, vol. 13, E155, pp. 1-15 (16 pages).
Te Kulve et al., "Early evening light mitigates sleep compromising physiological and alerting responses to subsequent late evening light," Scientific Reports, 2019, vol. 9, No. 16064, pp. 1-12.
Tebb et al., "Use of theory in computer-based interventions to reduce alcohol use among adolescents and young adults: a systematic review," BMC Public Health, 2016, vol. 16, No. 517, pp. 1-33.
Techau, David et al. "Buildings, Brains and Behaviour: Towards an affective neuroscience of architecture: The Hedonic Impact of Sustainable Work Environments on Occupant Well-being," World Health Design, 2016, pp. 24-37.

Tennessen et al., "Views to Nature: Effects on Attention," Journal of Environmental Psychology, 1995, vol. 15, pp. 77-85.
Third Examination Report issued in AU Application No. 2016202287 dated Feb. 15, 2021.
Tong, Van T. et al., "Clinical interventions to reduce secondhand smoke exposure among pregnant women: a systematic review," Tobacco Control, Author Manuscript, 2015 (17 pages).
U.S. Green Building Council, "Daylight and views—daylight," 2009, available at https://www.usgbc.org/credits/schools/v2009/ieqc81.
Uğursal et al., "The effect of temperature, metabolic rate and dynamic localized airflow on thermal comfort," Applied Energy, 2013, vol. 111, pp. 64-73.
Uğursal, Ahmet, et al., "The effect of temperature, metabolic rate and dynamic localized airflow on thermal comfort," Applied Energy, 2013, vol. 111, pp. 64-73 (10 pages).
Ulrich, "View Through a Window May Influence Recovery from Surgery," Science, 1984, vol. 224, pp. 420-421.
Unsworth et al., "An automated version of the operation span task," Behavior Research Methods, 2005, vol. 37, No. 3, pp. 498-505.
US Department of Health and Human Services, 2008 Physical Activity Guidelines for Americans, Oct. 2008, available at https://health.gov/paguidelines/pdf/paguide.pdf (76 pages).
US Department of Justice Civil Rights Division, 2010 ADA Standards for Accessible Design, available at https://www.ada.gov/regs2010/2010ADAStandards/2010ADAStandards.pdf, accessed Oct. 31, 2017 (279 pages).
Van Den Wymelenberg, "Patterns of occupant interaction with window blinds: A literature review," Energy and Buildings, 2012, vol. 51, pp. 165-176.
Van Eerd, D. et al., "Effectiveness of workplace interventions in the prevention of upper extremity musculoskeletal disorders and symptoms: an update of the evidence," Occupational and Environmental Medicine, 2016, vol. 73, pp. 62-70.
Vandewalle et al., "Daytime Light Exposure Dynamically Enhances Brain Responses," Current Biology, 2006, vol. 16, pp. 1616-1621.
Vastamäki et al., "A behavioural model of temperature controller usage and energy saving," Personal and Ubiquitous Computing, 2005, vol. 9, pp. 250-259.
Veitch et al., "A model of satisfaction with open-plan office conditions: COPE field findings," Journal of Environmental Psychology, 2007, vol. 27, pp. 177-189.
Veitch et al., "Assessing Beliefs about Lighting Effects on Health, Performance, Mood, and Social Behavior," Environment and Behavior, 1996, vol. 28, No. 4, pp. 446-470.
Veitch et al., "Determinants of Lighting Quality II: Research and Recommendations," presented at the 104th Annual Convention of the American Psychological Association, 1996 (57 pages).
Verlarde et al., "Health effects of viewing landscapes—Landscape types in environmental psychology," Urban Forestry & Urban Greening, 2007, vol. 6, pp. 199-212.
Viola et al., "Blue-enriched white light in the workplace improves self-reported alertness, performance and sleep quality," Scandinavian Journal of Work, Environment & Health, 2008, vol. 34, No. 4, pp. 294-306.
Wargocki et al., "Ten questions concerning thermal and indoor air quality effects on the performance of office work and schoolwork," Building and Environment, 2017, vol. 112, pp. 359-366.
Wargocki et al., "The Effects of Outdoor Air Supply Rate in an Office on Perceived Air Quality, Sick Building Syndrome (SBS) Symptoms and Productivity," Indoor Air, 2000, vol. 10, pp. 222-236.
Wells et al., "Subjective Responses to the Lighting Installation in a Modern Office Building and their Design Implications," Building Science, 1965, vol. 1, pp. 57-68.
Weschler, "Ozone in Indoor Environments: Concentration and Chemistry," Indoor Air, 2000, vol. 10, pp. 269-288.
Weschler, "Ozone's Impact on Public Health: Contributions from Indoor Exposures to Ozone and Products of Ozone-Initiated Chemistry," Environmental Health Perspectives, 2006, vol. 114, No. 10, pp. 1489-1496.

(56) References Cited

OTHER PUBLICATIONS

West et al., "Blue light from light-emitting diodes elicits a dose-dependent suppression of melatonin in humans," Journal of Applied Physiology, 2011, vol. 110, pp. 619-626.
Williams et al., Next Generation Air Monitor (NGAM) VOC Sensor Evaluation Report, EPA/600/R-15/122,2015 (71 pages).
Wisthaler et al., "Reactions of ozone with human skin lipids: Sources of carbonyls, dicarbonyls, and hydroxycarbonyls in indoor air," Proceedings of the National Academy of Sciences, 2010, vol. 107, No. 15, pp. 6568-6575.
Wolkoff, "Impact of Air Velocity, Temperature, Humidity, and Air on Long-Term VOC Emissions From Building Products," Atmospheric Environment, 1998, vol. 32, No. 14/15, pp. 2659-2668.
Won et al., "The State-of-the-Art in Sensor Technology for Demand-Controlled Ventilation, PERD S5-42: Final Report," IRC-RR-243, NRC Publications Archive, 2005 (89 pages).
Wong et al., "A multivariate-logistic model for acceptance of indoor environmental quality (IEQ) in offices," Building and Environment, 2008, vol. 48, pp. 1-6.
World Health Organization, "Global Nutrition Targets 2025: Low Birth Weight policy Brief," 2014, Geneva (8 pages).
World Health Organization, "Guideline: Daily iron supplementation in adult women and adolescent girls," 2016, Geneva (34 pages).
World Health Organization, "Guideline: Daily iron supplementation in infants and children," 2016, Geneva (54 pages).
World Health Organization, "WHO Recommendations for the Prevention and Management of tobacco use and second-hand smoke exposure in pregnancy," 2013 (104 pages).
Xiong et al., "Potential indicators for the effect of temperature steps on human health and thermal comfort," Energy and Buildings, 2016, vol. 113, pp. 87-98.
Yu et al., "People who live in a cold climate: thermal adaptation differences based on availability of heating," Indoor Air, 2013, vol. 23, pp. 303-310.
Zhai et al., "Human comfort and perceived air quality in warm and humid environments with ceiling fans," Building and Environment, 2015, vol. 90, pp. 178-185 (8 pages).
Zhai, Yongchao et al., "Comfort under personally controlled air movement in warm and humid environments," Building and Environment, 2013 (16 pages).
Zhai, Yongchao, et al., "Using air movement for comfort during moderate exercise," Building and Environment, 2015, vol. 24, pp. 344-352 (9 pages).
Zhang et al., "Study on TVOCs concentration distribution and evaluation of inhaled air quality under a re-circulated ventilation system," Building and Environment, 2007, vol. 42, pp. 1110-1118.
Zhang et al., "Thermal comfort in naturally ventilated buildings in hot-humid area of China," Building and Environment, 2010, vol. 45, pp. 2562-2570.
Zhang, Hui, "Human Thermal Sensation and Comfort in Transient and Non-Uniform Thermal Environments," Dissertation, 2003, University of California, Berkeley (436 pages).
Zhang, Yu F., et al., "The influence of heated or cooled seats on the acceptable ambient temperature range," Ergonomics, 2007, vol. 50, No. 4, pp. 586-600 (16 pages).
Zhao et al., "Effect of particle spatial distribution on particle deposition in ventilation rooms," Journal of Hazardous Materials, 2009, vol. 170, pp. 449-456.
Zhou et al., "Experimental study of the influence of anticipated control on human thermal sensation and thermal comfort," Indoor Air, 2014, vol. 24, pp. 171-177.
Zhu, Hongmei et al., "Is self-monitoring of blood glucose effective in improving glycaemic control in type 2 diabetes without insulin treatment: a meta-analysis of randomised controlled trials," BMJ Open, 2016, vol. 6, pp. 1-9 (9 pages).
Zhuang et al., "Haze insights and mitigation in China: an overview," Journal of Environmental Sciences, 2014, vol. 26, pp. 2-12 (11 pages).
Zinzi, "Office worker preferences of electrochromic windows: a pilot study," Building and Environment, 2006, vol. 41, pp. 1262-1273.
"Active Design Guidelines: Promoting Physical Activity and Health in Design," New York City Departments of Design and Construction, 2010.
"Assembly: Civic Design Guidelines," Center for Active Design, 2018.
Allergy Buyers Club, "Philips Wake Up Light Dawn Simulators Alarm Clocks," retrieved from http://www.allergybuyersclub.com/philips-wake-up-light-dawn-simulator-alarm-clocks.html, retrieved on Aug. 13, 2012, 2 pages.
Amendment, filed Jan. 25, 2018, for U.S. Appl. No. 15/421,046, Eisele et al., "LED Lighting System," 6 pages.
American Ultraviolet, "Handheld Germicidal Fixtures," retrieved from http://americanultraviolet.com/germicidal_solutions/commercial_products/handheld . . . , retrieved on Aug. 13, 2012, 1 page.
American Ultraviolet, "In Room Germicidal Solutions," HVAC MRS (0810/2.5M), retrieved from http://www.americanultraviolet.com, 2 pages.
Australian Examination report No. 1, dated Dec. 13, 2017, for Australian Application No. 2017200995, 6 pages.
Australian Patent Examination Report, dated Sep. 14, 2016, for Australian Application No. 2013308871, 5 pages.
Averett et al., "Titanium Dioxide Photocatalytic Compositions and Uses Thereof," U.S. Appl. No. 61/482,393, filed May 4, 2011, 25 pages.
Brookstone, "Tranquil Moments® Advanced Sleep Sounds," 2012, retrieved from http://www.brookstone.com/tranquil-moments-advanced-sleep-sound . . . , retrieved on Apr. 28, 2014, 3 pages.
Canadian Office Action, dated Jul. 18, 2017, for Canadian Application No. 2,946,367, 3 pages.
Canadian Office Action, dated Jul. 25, 2017, for Canadian Application No. 2,940,766, 6 pages.
Chinese Office Action, dated May 5, 2016, for Chinese Application No. 201380051774.0, 10 pages.
Communication pursuant to Article 94(3) EPC, dated Mar. 15, 2018, for European Application No. 15 754 628.4-1222, 9 pages.
Communication pursuant to Article 94(3) EPC, dated Nov. 23, 2016, for European Application No. 13833105.3, 8 pages.
Communication pursuant to Rule 164(1) EPC, dated Mar. 30, 2016, for European Application No. 13833105.3-1853 / 2891019, 9 pages.
Corrected Notice of Allowance, dated Jun. 26, 2017, for U.S. Appl. No. 14/012,444, Pillai et al, "Systems, Methods and Articles for Enhancing Wellness Associated With Habitable Environments," 2 pages.
Corrected Notice of Allowance, dated Jun. 6, 2017, for U.S. Appl. No. 14/012,444, Pillai et al, "Systems, Methods and Articles for Enhancing Wellness Associated With Habitable Environments," 2 pages.
Delos, "Delos and MGM Grand Las Vegas Introduce First-Ever Stay Well Rooms," Sep. 20, 2012, retrieved from http://delosliving.com/staywell/delos-mgm-grand-las-vegas-introduce-first-ever-stay-well- . . . , retrieved on May 14, 2014, 4 pages.
Delos, "Delos Announces First-Ever WELL™ Certified Office At CBRE Headquarters in Los Angeles," Nov. 19, 2013, retrieved from http://delosliving.com/press-release/delos-the-pioneer-of-wellness-real-estate-a nnounces-fi . . . , retrieved on May 14, 2014, 4 pages.
Delos, "MGM Grand and Delos Complete Expansion of Stay Well Experience and Introduce New Stay Well Lounge," Feb. 26, 2014, retrieved from http://delosliving.com/press-release/mgm-grand-and-delos-complete-expansion-of-s tay-we . . . , retrieved on May 14, 2014, 4 pages.
Delos, "World's First WELL® Certified Restaurants Introduced by Delos and LYFE Kitchen," Dec. 4, 2013, retrieved from http://delosliving.com/press-release/worlds-first-well-certified-restaurants-int roduced-by-d . . . retrieved on May 14, 2014, 4 pages.
Delos, "World's First Wellness-Infused Student Housing Model in Philadelphia for St. Joseph's University Introduced by Delos and Cross Properties," Nov. 25, 2013, retrieved from http://delosliving.com/press-release/delos-the-pioneer-of-wellness-real-estate-a nd-cross-pr . . . , retrieved on May 14, 2014, 4 pages.

(56) References Cited

OTHER PUBLICATIONS

Delos, "Introducing Wellness Real Estate—Can Your Home Actually Improve Your Health?," May 1, 2012, retrieved from http://delosliving.com/press-release/can-your-home-actually-improve-your-health/ , retrieved on May 14, 2014, 3 pages.
Eisele et al, "LED Lighting System," Notice of Allowance, dated Apr. 21, 2015, for U.S. Appl. No. 14/486,753, 9 pages.
Eisele et al, "LED Lighting System," Notice of Allowance, dated Mar. 14, 2016, for U.S. Appl. No. 14/805,243, 6 pages.
Eisele et al, "LED Lighting System," Notice of Allowance, dated May 13, 2014, for U.S. Appl. No. 13/863,589, 6 pages.
Eisele et al, "LED Lighting System," Office Action, dated Feb. 4, 2015, for U.S. Appl. No. 14/486,753, 7 pages.
Eisele et al, "LED Lighting System," Office Action, dated Jul. 26, 2012, for U.S. Appl. No. 12/900,158, 13 pages.
Eisele et al, "LED Lighting System," Office Action, dated Jun. 5, 2013, for U.S. Appl. No. 13/863,589, 5 pages.
Eisele et al, "LED Lighting System," Office Action, dated Nov. 1, 2013, for U.S. Appl. No. 13/863,589, 6 pages.
Eisele et al, "LED Lighting System," Office Action, dated Oct. 22, 2015, for U.S. Appl. No. 14/805,243, 18 pages.
Eisele et al, "LED Lighting System," Preliminary Amendment, filed Dec. 30, 2014, for U.S. Appl. No. 14/486,753.
Eisele et al, "LED Lighting System," Preliminary Amendment, filed Sep. 15, 2015, for U.S. Appl. No. 14/805,243, 9 pages.
Eisele et al, "LED Lighting System," Preliminary Amendment, filed Sep. 8, 2016, for U.S. Appl. No. 15/187,317, 9 pages.
Eisele et al, "LED Lighting System," Response, filed Jan. 27, 2014, for U.S. Appl. No. 13/863,589, 3 pages.
Eisele et al, "LED Lighting System," Response, filed Jan. 5, 2016, for U.S. Appl. No. 14/805,243, 3 pages.
Eisele et al, "LED Lighting System," Response, filed Mar. 6, 2015, for U.S. Appl. No. 14/486,753, 3 pages.
Eisele et al, "LED Lighting System," Response, filed Sep. 4, 2013, for U.S. Appl. No. 13/863,589, 3 pages.
Eisele et al., "LED Lighting System," Amendment, filed Oct. 24, 2012, for U.S. Appl. No. 12/900,158, 12 pages.
Eisele et al., "LED Lighting System," U.S. Appl. No. 61/249,858, filed Oct. 8, 2009, 58 pages.
Eisele et al., "LED Lighting System," Notice of Allowance dated Jan. 9, 2013, for U.S. Appl. No. 12/900,158, 9 pages.
European Search Report for EP Application No. 15160578.9, dated Aug. 11, 2015, 8 pages.
Examiner's Report issued in CA Application No. 2,940,766 dated Jan. 11, 2019.
Extended European Search Report and Lack of Unity of Invention Sheet B, dated Jul. 28, 2016, for European Application No. 13833105.3, 17 pages.
Extended European Search Report issued in EP Application No. 17844397.4 dated Jun. 17, 2020 (8 pages).
Extended European Search report issued in EP Application No. 20152815.5 dated Aug. 4, 2020.
Extended European Search Report issued in EP Application No. 20191237.5 dated Sep. 21, 2020.
Extended European Search Report, dated Feb. 1, 2018, for European Application No. 17167920.2-1213, 10 pages.
Extended European Search Report, dated Jul. 12, 2017, for European Application No. 15754628.4-1958, 11 pages.
Extended European Search Report, dated May 28, 2018, for European Application No. 16737803.3-1222/3245631, 7 pages.
Extended European Search Report, dated Nov. 5, 2014, for European Application No. 12779504.5-1352, 6 pages.
Fabrictech International, "PureCare™ Antibacterial Silver," retrieved from http://www.fabrictech.com/shop/purecaresilver.html, retrieved on Aug. 13, 2012, 1 page.
Fabrictech International, "Total Health & Wellness Protection Package—Save 25%," retrieved from http://www.fabrictech.com/shop/custom-package/total-healthawellness-protection.h tml, retrieved on Aug. 13, 2012, 3 pages.

First Examination Report issued in IN Application No. 201617032677 dated Jul. 30, 2020.
Goodman, "Green Wall Frame," Amendment After Allowance, filed May 11, 2016, for U.S. Appl. No. 29/528,147, 8 pages.
Goodman, "Green Wall Frame," Notice of Allowance, dated Feb. 11, 2016, for U.S. Appl. No. 29/528,147, 11 pges.
GSky Plant Systems, Inc., "Smart Wall Cabinet," 2012, retrieved from http://gsky.com/green-walls/smartwall/, retrieved on Apr. 29, 2015, 3 pages.
International Search Report and the Written Opinion of the International Searching Authority, dated Jun. 8, 2015, for International Application No. PCT/US2015/017528, 20 pages.
International Search Report and Written Opinion of the International Searching Authority, dated Aug. 29, 2016, for International Application No. PCT/US2016/034416, 22 pages.
International Search Report for PCT/US2017/048382 dated Jan. 4, 2018 (4 pages).
International Search Report, dated Apr. 28, 2016, for International Application No. PCT/US2016/013215, 5 pages.
International Search Report, dated Dec. 26, 2013, for International Application No. PCT/US2013/057070, 4 pages.
International Search Report, dated Feb. 4, 2011, for International Application No. PCT/US2010/051791, 2 pages.
Japanese Office Action dated Apr. 25, 2017 for JP Application No. 2015-529995, with English summary, 14 pages.
Jernigan, "Light studies focus on circadian rhythms," BioPhotonics, Jul. 2009, retrieved from http://www.photonics.com/Article.aspx?PID=I&VID=43&IID=396&AID=38995, retrieved on Nov. 3, 2014, 2 pages.
Jernigan, R., "Light Studies Focus on Circadian Rhythms," Photonics Showcase, Nov. 2009, p. 12.
Jones, "Chapter 4'Acoustical Treatment for Indoor Areas," in Handbook for Sound Engineers, Ballou (ed.), Burlington, MA, Focal Press, 2008, 65-94.
Klein, Laura et al., "Coordinating occupant behavior for building energy and comfort management using multi-agent systems," Automatoin In Construction, vol. 22, Mar. 2012, pp. 525-536.
Land, "Using Vitamin C to Neutralize Chlorine in Water Systems," Recreation Management Tech Tips, Apr. 2005, retrieved from http://www.fs.fed.us/t-d/pubs/html/05231301/05231301.html, retrieved on Mar. 1, 2016, 6 pages.
Macary et al., "Systems, Methods and Articles for Monitoring and Enhancing Human Wellness," U.S. Appl. No. 15/543,114, filed Jul. 12, 2017, 113 pages.
Mold Inspection California, "Killing Mold With Ozone & Thermal Heat," retrieved from http://moldinspectioncalifornia.com/kill_mold_with_ozone.html, 3 pages.
NaturVention, "Science," URL=https://www.naturvention.com/technology-and-science/science/, download date Apr. 5, 2016, 4 pages.
NaturVention, "Technology," URL=https://www.naturvention.com/technology-and-science/, download date Apr. 5, 2016, 6 pages.
Office Action issued in CN Application No. 201580021358.5 dated Feb. 2, 2019.
Office Action issued in MX Application No. MX/a/2016/011107.
Office Action, dated May 21, 2018, for U.S. Appl. No. 15/121,953, Pillai et al., "Systems and Articles for Enhancing Wellness Associated With Habitable Environments," 38 pages.
Office Action, dated May 31, 2018, for U.S. Appl. No. 15/421,046, Eisele et al., "LED Lighting System," 9 pages.
Office Action, dated Oct. 27, 2017, for U.S. Appl. No. 15/421,046, Eisele et al., "LED Lighting System," 8 pages.
OxiTitan, "Light Powered Protection," retrieved from http://www.oxititan.com, retrieved on Aug. 13, 2012, 2 pages.
Pervez et al., "Photonic Crystal Spectrometer," U.S. Appl. No. 61/278,773, filed Oct. 12, 2009, 78 pages.
Pervez et al., "Photonic Crystal Spectrometer," U.S. Appl. No. 61/349,570, filed May 28, 2010, 52 pages.
Pillai et al., "Systems, Methods and Articles for Enhancing Wellness Associated With Habitable Environments," Amendment, filed Jul. 21, 2016, for U.S. Appl. No. 14/012,444, 25 pages.

(56) References Cited

OTHER PUBLICATIONS

Pillai et al., "Systems, Methods and Articles for Enhancing Wellness Associated With Habitable Environments," Office Action, dated Mar. 22, 2016, for U.S. Appl. No. 14/012,444, 29 pages.
Pillai et al., "Systems, Methods and Articles for Enhancing Wellness Associated With Habitable Environments," Preliminary Amendment, filed Mar. 25, 2015, for U.S. Appl. No. 14/012,444, 149 pages.
Pillai et al., "Systems, Methods and Articles for Enhancing Wellness Associated With Habitable Environments," U.S. Appl. No. 15/409,233, filed Jan. 18, 2017, 84 pages.
Pillai et al., "Systems, Methods and Articles for Enhancing Wellness Associated With Habitable Environments," U.S. Appl. No. 15/421,022, filed Jan. 31, 2017, 84 pages.
Preliminary Amendment, filed Jul. 12, 2017, for U.S. Appl. No. 15/543,114, Macary et al., "Systems, Methods and Articles for Monitoring and Enhancing Human Wellness," 10 pages.
Summons to attend oral proceedings issued in EP Application No. 15754628.4 on Sep. 10, 2018.
Suryadevara, N.K. et al., "Sensor data fusion to determine wellness of an elderly in intelligent home monitoring environment", Instrumentation and Measurement Technology Conference, Graz: IEEE, (20120513), ISSN 1091-5281, pp. 947-952, XP032451677.
Vitashower Corp., "Products," retrieved from http://www.vitashowercorp.com/products.html, retrieved on May 13, 2014, 8 pages.
Vitashower Corporation, "Ascorbic Acid Reduction of Residual Active Chlorine in Potable Water Prior to Halocarboxylate Determination," from Urbansky et al., Journal of Environmental Monitoring 2(3):253-256, 2000, retrieved from http://www.vitashowercorp.com/research.html, retrieved on May 13, 2014, 2 pages.
Vitashower Corporation, "Frequently Asked Questions," 2003, retrieved from http://www.vitashowercorp.com/FAQs.html, retrieved on May 13, 2014, 3 pages.
Vitashower Corporation, "Vitamin C Shower Filter SF-2000," 2003, retrieved from http://www.vitashowercorp.com/products.html, retrieved on May 13, 2014, 8 pages.
Vitashower Corporation, "Welcome to Vitashower Corporation," 2003, retrieved from http://www.vitashowercorp.com/index.html, retrieved on May 13, 2014, 4 pages.
Wikipedia, "Home automation," Jan. 17, 2014, URL: https://en.wikipedia.org/w/index.php? title=Home_automation&oldid=591169195, retreived on Sep. 2, 2020 (11 pages).
Wikipedia, "Thermostat," as archived on Jan. 24, 2014, URL=https://en.wikipedia.org/w/index.php?title=Thermostat&oldid=592239648, download date Jun. 30, 2017, 10 pages.
Written Opinion of the International Searching Authority, dated Apr. 28, 2016, for International Application No. PCT/US2016/013215, 16 pages.
Written Opinion of the International Searching Authority, dated Dec. 26, 2013, for International Application No. PCT/US2013/057070, 5 pages.

\* cited by examiner

500 ⟶

| Provide signals to vary illumination passed by pane(s) of electrochromatic material | ⟵ 502 |

| Provide signals to control electrical motor drivingly coupled to move shade(s)/curtain(s) | ⟵ 602 |

FIG. 6

SYSTEMS, METHODS AND ARTICLES FOR ENHANCING WELLNESS ASSOCIATED WITH HABITABLE ENVIRONMENTS

This application is a continuation of U.S. application Ser. No. 16/444,877, filed on Jun. 18, 2019, which issued as U.S. Pat. No. 10,928,842 on Feb. 23, 2021, and is a continuation of U.S. application Ser. No. 15/421,022, filed Jan. 31, 2017, which issued as U.S. Pat. No. 10,845,829 on Nov. 24, 2020; said U.S. application Ser. No. 16/444,877, filed on Jun. 18, 2019, now U.S. Pat. No. 10,928,842 is a continuation of U.S. application Ser. No. 15/421,022, filed on Jan. 31, 2017, now U.S. Pat. No. 10,845,829, and is a continuation of Ser. No. 15/409,233, filed on Jan. 18, 2017, which issued as U.S. Pat. No. 10,691,148 on Jun. 23, 2020; said U.S. application Ser. No. 15/421,022, filed Jan. 31, 2017, now U.S. Pat. No. 10,845,829 and said U.S. application Ser. No. 15/409,233, filed Jan. 18, 2017, now U.S. Pat. No. 10,691,148, both are continuations of U.S. application Ser. No. 14/012,444, filed Aug. 28, 2013, which issued as U.S. Pat. No. 9,715,242 on Jul. 25, 2017, which claims the benefit of U.S. Provisional Application No. 61/694,125, filed Aug. 28, 2012, all of which are incorporated herein by reference in their entirety.

BACKGROUND

Field

This disclosure generally relates to habitable environments, for instance homes, hotel or motels, offices and hospitals, and particularly to techniques for enhancing human habitation in such environments.

Description of the Related Art

Most people spend significant amounts of time in habitable environments such as enclosed spaces associated with homes, apartments, condominium units, hotel suites or rooms, motel suites or rooms, spas, hospital, and other public and private facilities. Sometimes these enclosed spaces are controlled, or even owned by, the principal occupants, such as homes, apartments or condominium units. Other times these enclosed spaces are controlled by others, for example a facility owner or operator who may own and/or operate a hotel, motel, spa, hospital.

Significant time in these spaces exposes the occupant to a wide range of environmental factors, any of which may have either adverse or beneficial effects on the occupant's health, well-being or sense of well-being. Minimizing exposure to environmental factors that tend to have an adverse effect is desirable, as is increasing exposure to environmental factors that tend to have a beneficial effect.

New approaches that enhance habitable environments are desirable.

BRIEF SUMMARY

Various approaches described herein employ combinations of passive and active techniques for enhancing environmental characteristics of inhabitable environments, to reduce or ameliorate adverse effects and to increase beneficial effects. These approaches may have specific application in hospitality settings, for instance hotel or motel rooms, spas, resorts, cruise boat cabins, and extended stay suites. These approaches may have application in occupational environments, for instance offices, retail locations, factories or warehouses. These approaches may have application in residential settings, for instance homes, apartments, porches, condominiums or other residences. These approaches may have application in other settings, for instance hospitals or clinics, waiting areas associated with transportation such as airports and train stations, and/or public areas such as theaters, arenas, stadiums, museums and other venues. The various combinations may advantageously produce synergistic results, which may not be otherwise achievable on an individual basis.

A system to control environmental characteristics in an enclosed space may be summarized as including a control subsystem that includes at least one processor and at least one nontransitory processor-readable medium that stores at least one of processor-executable instructions or data; an illumination subsystem operable to control illumination characteristics of illumination provided in at least a portion of the enclosed spaced, the illumination subsystem including: a plurality of illumination sources selectively operable to emit illumination at a number of levels and a number of wavelengths; at least one actuator operable to control an amount of illumination received into the enclosed space via one or more windows from an external source of illumination; and at least one user actuatable input device located in the enclosed space and communicatively coupled to the control subsystem and selectively actuatable by a user to switch between a circadian setting and at least one override setting, wherein: the control subsystem is communicatively coupled to control the plurality of illumination sources and the at least one actuator, and when in the circadian setting the control subsystem provides signals to the illumination sources and the at least one actuator to cause the illumination sources and the at least one actuator to provide illumination according to a defined circadian pattern over a period of time, the circadian pattern at least approximately matching changes in illumination level and color temperature of naturally occurring illumination of at least one defined latitude over the period of time.

At least one actuator may include electrochromatic glass in the at least one window. At least one actuator may include an electric motor physically coupled to a transmission that selectively positions at least one blackout shade across the at least one window. In a night portion of the circadian pattern, the control subsystem may provide signals to at least a subset of the illumination sources which are, for example solid-state illumination sources or small incandescent lights to produce a low level of illumination proximate at least one path to a door of the enclosed space. When in a first override setting of the at least one override setting the control subsystem may provide signals to the illumination sources and the at least one actuator to cause the illumination sources and the at least one actuator to provide illumination that does not follow the defined circadian pattern. When in a second override setting of the at least one override setting the control subsystem may provide signals to the illumination sources and the at least one actuator to cause the illumination sources and the at least one actuator to provide illumination to the enclosed space based at least in part on a geographic location from where an occupant of the enclosed spaced originated to accommodate a change in circadian rhythm due to travel by the occupant. When in a third override setting of the at least one override setting the control subsystem may provide signals to the illumination sources and the at least one actuator to cause the illumination sources and the at least one actuator to provide illumination to the enclosed space based at least in part on a time of year to accommodate a change in circadian rhythm due to seasonal variation at a geographic location of the enclosed space.

When in yet another override setting of the at least one override setting the control subsystem may provide signals to the illumination sources and the at least one actuator to cause the illumination sources and the at least one actuator to provide illumination to the enclosed space to produce a therapeutic effect in an occupant of the enclosed space. The system may further include at least one sensor positioned to detect presence of an occupant in the enclosed spaced and communicatively coupled to the control subsystem to provide signals indicative of a current occupancy condition of the enclosed space. The system may further include at least one user actuatable input device located remotely from the enclosed space and communicatively coupled to the control subsystem and selectively actuatable to switch between a plurality of settings for the system. The system may further include an air handling subsystem to control air characteristics of air in the enclosed space, the air handling system including at least one of: an air filter, a heater, an air conditioner, a humidifier, a dehumidifier, a vent, a fan, or a compressor, and the air handling system including at least one of: a temperature sensor or a humidity sensor positioned to detect a temperature or a humidity proximate at least one portion of the enclosed space. The control subsystem may provide signals to at least one portion of the air handling subsystem to control at least one of the temperature or the humidity of air in the enclosed space. The control subsystem may provide signals to adjust at least the temperature of the air in the enclosed space based at least in part on the circadian pattern over the period of time. The at least one air filter may include at least one of: a HEPA mechanical air filter, an electrostatic particle air filter, or an ultraviolet air filter. The air handling subsystem may further include a number of inlets for selectively introducing scents into the air in the enclosed space from a number of reservoirs and the control subsystem may provide signals to at least one portion of the air handling subsystem to control the introduction of the scents into the air in the enclosed space. The control subsystem may provide signals to at least one portion of the air handling subsystem to control the introduction of the scents into the air in the enclosed space based on a defined schedule. The control subsystem may provide signals to at least one portion of the air handling subsystem to control the introduction of the scents into the air in the enclosed space on demand in response to a user input. The system may further include a water supply subsystem including a sediment filter and an activated charcoal filter that filters water that is to be supplied to the enclosed space via a faucet or a showerhead. The water supply subsystem may further include an ultraviolet water sanitizer that illuminates water that is to be supplied to the enclosed space via a faucet or a showerhead with ultraviolet illumination. The water supply subsystem may further include an inlet to supply vitamin C to water that is to be supplied to the enclosed space via a showerhead. The system may further include an ambient sound subsystem, that may include at least one piece of acoustic insulation positioned to acoustically insulate at least some of a number of plumbing components; at least one acoustic damping door that acoustically insulates the enclosed space from an exterior thereof when the at least one acoustic damping door is in a closed position; at least one acoustic damping window that acoustically insulates the enclosed space from the exterior thereof when the at least one acoustic damping window is in a closed position; at least one acoustic damping walling component that acoustically insulates the enclosed space from the exterior thereof; and at least one acoustic damping flooring component that acoustically insulates the enclosed space from the exterior thereof. An ambient sound level in the enclosed space may be less than 45 dB when active source of sound is operating in the enclosed space. The system may further include at least one speaker communicatively coupled to be controlled by the control subsystem to play sound in the enclosed space at a sound level that changes in synchronization with a change in a level of illumination emitted by the illumination sources. The control subsystem may provide signals to gradually increase both the sound and illumination levels in response to an occurrence of a pre-set time. The system may further include a cushioned low volatile organic compound emitting flooring in the enclosed space. The system may further include a textured reflexology flooring path in the enclosed space. The system may further include at least one electromagnetic field shield positioned relative to wiring to reduce a level of electromagnetic field introduced into the enclosed space by the wiring.

A method of controlling environmental characteristics in an enclosed space may be summarized as including receiving at a first time a first input indicative of a selection of a circadian setting; in response to the first input indicative of the selection of the circadian setting, providing signals by a control subsystem to cause a plurality of illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination varies over a first period of time according to a circadian pattern; receiving at a second time a second input indicative of a selection of a first non-circadian setting; and in response to the second input indicative of the selection of the first non-circadian setting, providing signals by the control subsystem to cause a plurality of illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination does not vary over a second period of time according to the circadian pattern.

In response to the second input indicative of the selection of the first non-circadian setting, the control subsystem may provide signals to the plurality of illumination sources and the at least one actuator such that the combination of the artificial and the natural illumination remains constant over the second period of time. The method may further include receiving at a third time a third input indicative of a selection of a second non-circadian setting that is a sleep time setting; and in response to the third input indicative of the second non-circadian setting that is the sleep time setting, providing signals by the control subsystem to cause a subset of the illumination sources proximate to a floor in the enclosed space to emit artificial illumination at a low illumination level along at least one path and to cause the at least one actuator to prevent natural illumination from being received into the enclosed space via the one or more windows. The method may further include receiving at a fourth time a fourth input indicative of a selection of a travel adjustment setting; in response to the fourth input indicative of the travel adjustment setting: determining a travel adjustment illumination pattern based at least in part on a geographic location from where an occupant of the enclosed spaced originated to accommodate a change in circadian rhythm due to travel by the occupant; and providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the determined travel adjustment illumination pattern in the enclosed space. The method may further include receiving at a fourth time a fourth input indicative of a selection of a light therapy setting; and in response to the fourth input indicative of the light setting, providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the defined light therapy illumination pattern in the enclosed space over a therapeutic period of time. Providing signals by the control subsystem to cause the at least one actuator to control at least the level of natural illumination received into the enclosed space via the one or more windows may include providing signals to vary an amount of illumination passed by at least one pane of electrochromatic material. Providing signals by the control subsystem to cause the at least one actuator to control at least the level of natural illumination received into the enclosed space via the one or more windows may include providing signals to control an electrical motor drivingly coupled to move at least one of a shade or a curtain relative to the at least one window. The method may further include detecting by at least one sensor whether the enclosed spaced is occupied; and providing signals to the control subsystem indicative of whether the enclosed space is occupied. The method may further include receiving input by at least one user actuatable input device located remotely from the enclosed space; and providing signals to the control subsystem indicative of the received input. The method may further include providing signals by the control subsystem to at least one component of an air handling subsystem to control air characteristics of air in the enclosed space. Providing signals to at least one component of the air handling subsystem may include providing signals to at least one of an air filter, a heater, an air conditioner, a humidifier, a dehumidifier, a vent, a fan, or a compressor to control at least one of the temperature or the humidity of air in the enclosed space. The method may further include receiving signals by the control subsystem from at least one of: a temperature sensor or a humidity sensor positioned to detect a temperature or a humidity proximate at least one portion of the enclosed space. Providing signals to at least one component of the air handling subsystem may include providing signals to adjust at least a temperature of the air in the enclosed space based at least in part on the circadian pattern over the period of time. The method may further include filtering air for the enclosed space with at least one of: a HEPA mechanical air filter, an electrostatic particle air filter, or an ultraviolet air filter. The method may further include providing signals by the control subsystem to selectively introduce scents into the air in the enclosed space from a number of reservoirs. Providing signals by the control subsystem to selectively introduce scents into the air in the enclosed space may include providing signals based on a defined schedule. Providing signals by the control subsystem to selectively introduce scents into the air in the enclosed space may include providing signals based on demand in response to a user input. The method may further include filtering a supply of water to a faucet or a showerhead of the enclosed space via a water supply subsystem including at least one of a sediment filter or an activated charcoal filter, and exposing the water to ultraviolet illumination to sanitize the water. The method may further include introducing vitamin C into water that is to be supplied to the showerhead of the enclosed space. The method may further include supplying signals by the controller subsystem to at least one speaker to play sound in the enclosed space at a sound level that changes in synchronization with a change in a level of illumination emitted by the illumination sources.

A system to enhance environmental characteristics in a habitable environment may be summarized as including at least one acoustic damping window that acoustically insulates the habitable environment from the exterior thereof when the at least one acoustic damping window is in a closed position; at least one acoustic damping walling component that acoustically insulates the habitable environment from the exterior thereof; at least one acoustic damping flooring component that acoustically insulates the habitable environment from the exterior thereof; and at least one speaker selectively operable to play sound in the habitable environment.

The system may further include a plurality of illumination sources selectively operable to emit artificial illumination at a number of levels and a number of wavelengths in the habitable environment; at least one actuator operable to control an amount of illumination received into the habitable environment via one or more windows from an external source of natural illumination. The system may further include a control subsystem communicatively coupled to control the plurality of illumination sources, the at least one actuator, and the at least one speaker. The system may further include at least one acoustic damping door that acoustically insulates the habitable environment from an exterior thereof when the at least one acoustic damping door is in a closed position. The system may further include a photocatalyst antimicrobial agent on at least one surface in the habitable environment.

A method of controlling environmental characteristics in a habitable environment may be summarized as including distributing an antimicrobial agent in the habitable environment prior to occupancy of the habitable environment by a first occupant; subjecting surfaces in the habitable environment to ultraviolet illumination prior to occupancy of the habitable environment by the first occupant; applying antimicrobial bedding to a bed in the habitable environment prior to occupancy of the habitable environment by the first occupant; and setting an illumination pattern that controls both artificial and natural illumination provided in the habitable environment based on at least one characteristic of the first occupant.

The method may further include setting a sound pattern that controls artificial sound provided in the habitable environment based on at least one characteristic of the first occupant. Setting a sound pattern may include setting a sound pattern that is synchronized at least in part to the illumination pattern that controls both artificial and natural illumination provided in the habitable environment based on at least one characteristic of the first occupant. The method may further include removing the antimicrobial agent from the habitable environment prior to occupancy of the habitable environment by the first occupant. Distributing an antimicrobial agent in the habitable environment may include distributing a photocatalytic antimicrobial agent; and may further include exposing the antimicrobial agent to a defined wavelength of illumination for a defined time prior to occupancy of the habitable environment by the first occupant. The method may further include providing treated water to the habitable environment.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 5 is a flow diagram that shows a low level method of operating one or more components of a habitable environment enhancement system to adjust an amount of natural light received in the habitable environment using electrochromatic panes, according to one illustrated embodiment, which may be useful in performing at least a portion of the method illustrated in FIG. 4.

FIG. 6 is a flow diagram that shows a low level method of operating one or more components of a habitable environment enhancement system to adjust an amount of natural light received in the habitable environment using drapes, shades or curtains, according to one illustrated embodiment, which may be useful in performing at least a portion of the method illustrated in FIG. 4.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with environmental control such as fans, blowers, heaters, coolers such as air conditioners or swamp coolers, compressors, and control systems such as computing systems, as well as networks and other communications channels have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Environment Overview

Figure 1:
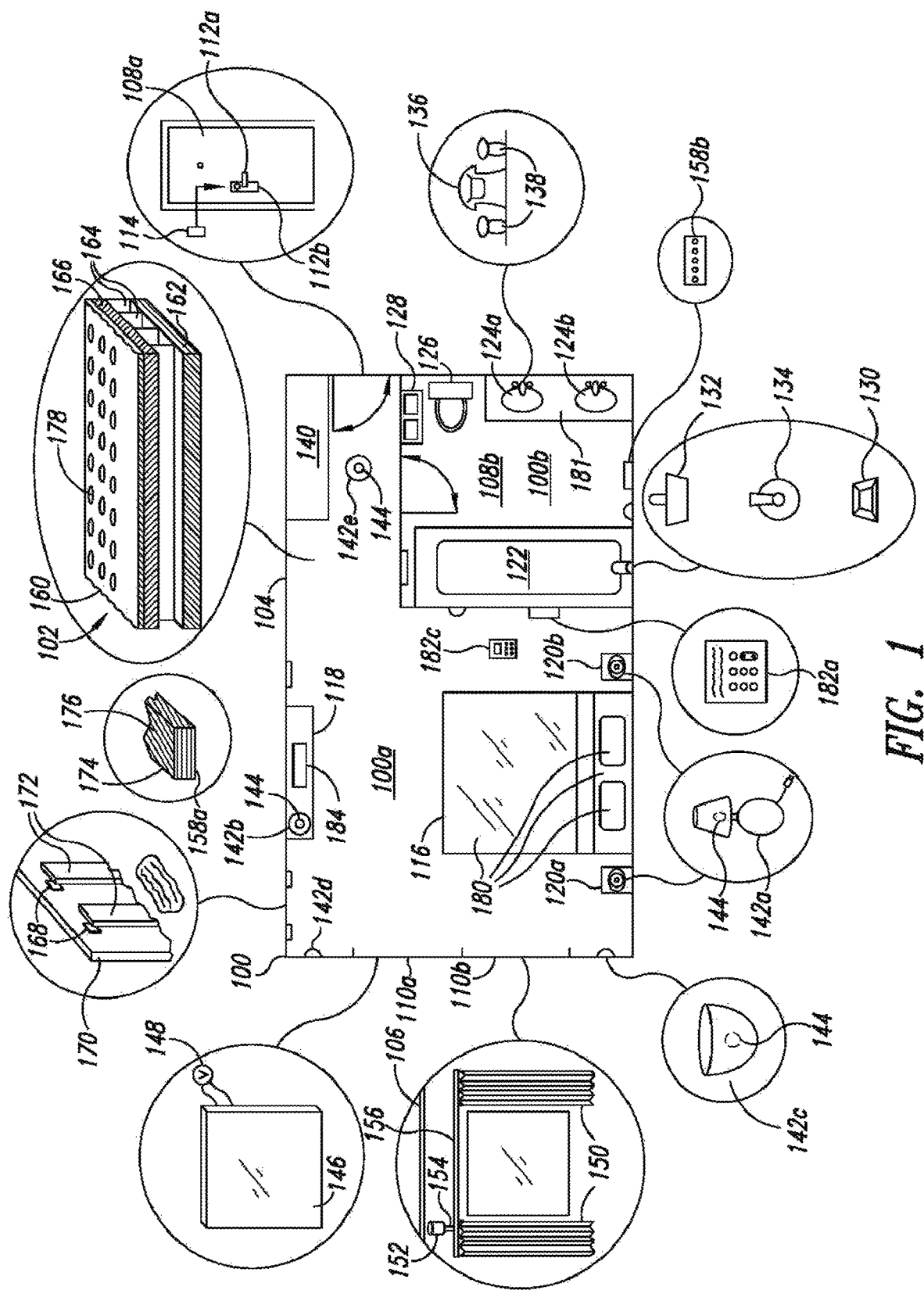
FIG. 1 is a schematic diagram of a habitable environment according to one illustrated embodiment, including enlarged views of various elements or components of the habitable environment.

FIG. 1 shows a habitable environment 100, according to one illustrated embodiment in which various apparatus, methods and articles described herein may operate.

The habitable environment 100 may take the form of one or more enclosed spaces, such as one or more rooms, for instance in a house, hotel, spa, condominium unit, apartment, office, hospital, or other accommodation which people typically inhabit.

The habitable environment 100 includes a floor system 102, wall system 104, and ceiling system 106, and may include one or more doors 108a, 108b (collectively 108) and/or windows 110a, 110b (collectively 110). The doors 108 may provide ingress and egress to an exterior environment, or may provide ingress and egress to other enclosed spaces within the habitable environment 100. For instance, one door 108a may provide passage between the habitable environment 100 and a hallway (not called out) outside of the habitable environment 100. Another door 108b may provide passage between one portion and another portion of the habitable environment 100, such as between a bedroom or living area 100a and a bathroom 100b.

The door 108a to the exterior may have a handle 112a with associated lock, for instance a cardkey entry lock 112b. Cardkey entry lock 112b reads an identifier either encoded in a magnetic stripe or in a wireless transponder (e.g., radio frequency identification or RFID transponder or smartcard) of a cardkey 114. The identifier may be logically associated with an inhabitant or occupant of the habitable environment 100. For example, a hotel guest may be assigned to a given suite, and issued a cardkey 114 that provides access to the suite. The identity of the guest may be stored in a database or other data structure with a logical relationship (e.g., key, pointer) to the suite. Likewise, various attributes of the guest may be stored in the database or other data structure, logically associated with the identity of the guest. As explained below, this may allow various aspects of the habitable environment 100 to be customized for the particular occupant.

As illustrated, the habitable environment 100 may be a suite, with a combined sleeping and living area 100a, and a separate bathroom 100b. The habitable environment 100 may include various pieces of furniture or fixtures. For example, the habitable environment 100 may include a bed 116, dresser 118, end tables 120a, 120b (collectively 120). Also for example, the habitable environment 100 include a bathtub or shower 122, sinks 124a, 124b (collectively 124), commode 126 and optionally towel racks 128 in the bathroom portion 100b. The bath or shower 122 may have a faucet 130, showerhead 132 and control handle 134. The control handle 134 is operable to control a flow of water via the faucet 130 and/or showerhead 132, from a supply of water (not shown in FIG. 1). The sink(s) may have a faucet 136 and control handle(s) 138. The control handle(s) 138 is operable to control a flow of water via the faucet 136 from a supply of water (not shown in FIG. 1). The habitable environment 100 may additionally include one or more closets 140.

The habitable environment 100 may include a number of components (e.g., devices, articles, structures) which contribute to a wellness or sense of wellness of the occupant of the habitable environment 100. Some of these components are active components, driven in response to commands or signals, while other components are passive components. These components are brought together as a system, in order to provide synergistic results, thereby enhancing a health, wellness or sense of wellbeing of an inhabitant or occupant of a habitable environment or enclosed space. The various components are discussed below with reference to FIGS. 1 and 2, and exemplary operation of such are discussed below with reference to FIGS. 3-10.

The habitable environment 100 may include a number of active components operable to achieve desired environmental characteristics, for example related to illumination, heating, ventilation and air conditioning (HVAC), water treatment, and acoustics.

Controlled lighting or illumination is one aspect of achieving the desired environmental characteristics of the habitable environment 100. Thus, the habitable environment 100 may include a number of artificial luminaires 142a-142e (collectively 142), which are controlled to produce desired output, for example by varying intensity and/or composition of wavelengths or color. Luminaires 142 may take a variety of forms, for example lamps (e.g., tabletop, floor standing) 142a, 142b, sconces 142c, 142d, and/or overhead lighting 142e. The luminaires 142 may employ a variety of illumination sources 144, for example incandescent lights, florescent lights, compact florescent lights, and light emitting diode (LED) lighting. The luminaires 142 may optionally include ballasts (e.g., electronic ballasts) and/or other electrical or electronic components required for operation. The luminaires 142 may also include various passive and/or active thermal management components to remove heat, thereby prolonging the operational life of the luminaires 142. Each luminaire 142 may include a plurality of individual illumination or light sources 144, respective ones or sets of the illumination sources 144 operable to emit light in a respective range of wavelengths. Some of the ranges may overlap, while other ranges may or may not overlap. The ones or sets of the illumination sources 144 may be individually operable to achieve any desired distribution of wavelengths at any given time. Each luminaire 142 may include one or more intensity adjustment circuits (e.g., dimmer circuits), which may take a large variety of forms depending on the type of illumination sources 144 employed. For example, an adjustable resistance type dimmer switch may be employed with incandescent sources, while a more sophisticated pulse width modulation technique may be used to control intensity of LED sources.

The habitable environment 100 may additionally or alternatively include a number of components which are controlled to adjust natural light being received in the habitable environment 100 via one or more windows 110 from an exterior thereof for example from a natural source of light (e.g., the Sun). These may include electrochromatic panes 146 in the window 110a and associated actuator, for instance a voltage source 148 coupled to control a transmissivity of the electrochromatic panes 146. Electrochromatic panes 146 may commonly be referred to as electrochromatic glass, but the embodiments herein are not intended to be limited to glass. These may include one or more drapes, shades or curtains or other window coverings (collectively window covering 150) and an actuator such as an electric motor 152 coupled by a transmission 154 to drive the window covering along a track 156 relative to the window(s) 110b.

Various approaches to illumination and components to provide illumination are discussed below, with reference to FIGS. 2 and 4-6.

HVAC is another aspect by which the desired environmental characteristics of the habitable environment 100 may be achieved. Thus, the habitable environment 100 may include a number of vents 158a-158b (only three shown, collectively 158) that provide air to the habitable environment 100 or portions thereof having desired air temperature, humidity, and/or air quality. At least one of the vents 158 may selectively supply scent(s) to the habitable environment 100 or a portion thereof. Various air treatments and components for treating air are discussed below, with reference to FIGS. 2 and 7.

Likewise, water is yet another aspect by which the desired environmental characteristics of the habitable environment 100 may be achieved. Thus, the habitable environment 100 may include a number of faucets 130, 136 and/or showerheads 132 which supply water which has been treated in a variety of ways to enhance wellness. Various water treatments and components for treating water are discussed below, with reference to FIGS. 2 and 9.

The habitable environment 100 may include a number of passive components to achieve desired environmental characteristics, for example related to flooring system 102, wall system 104, ceiling system 106, acoustics, air quality (e.g., zero or low VOC emitting), and hygiene or sanitation (e.g., anti-pathogen). Many of these are discussed below.

The habitable environment 100 may include flooring system 102, wall system 104 and/or ceiling system 106 designed to achieve a variety of benefits. For example, the flooring system 102, wall system 104 and/or ceiling system 106 designed to reduce exposure to noise.

Loud environments have become a part of modern life. Fans, overhead planes, passing traffic, and loud neighbors all contribute to ambient noise conditions in the home. About half of Americans live in areas where background noise is above 55 decibels (dB)—a level that most consider bothersome. On the logarithmic decibel scale, 0 dB is the point where sounds become discernible to the human ear, and every increase of 10 dB increases the sound pressure level by a factor of 10. Regular exposure to 85 dB for over eight hours at a time can lead to permanent hearing loss. In outdoor urban spaces not immediately adjacent to any sound generators the background noise is often close to 40 db. The World Health Organization recommends an ambient sound level of under 45 dB inside homes and 30 dB for bedrooms.

Thus, the habitable environment 100 may include various passive approaches to achieve the benefit of reduced noise.

Much of the bothersome noise in homes originates from the outside, so acoustic barriers are an important part of overall sound balance. Many of the same technologies that provide effective thermal insulation in walls and windows concurrently block noise. This allows for acoustic protection solutions, while incurring little additional cost. In addition, floor lining reduces sound transmission between apartments and improves perceptions of privacy.

For example, the habitable environment 100 may include a flooring system 102 designed to achieve a variety of benefits. The flooring system 102 may include floor covering 160, subflooring 162, and optionally acoustically damping floor mounts 164 coupling the flooring 160 to the subflooring 162. The flooring system 102 may include one or more additional layers of flooring 166, which provides a resilient member or layer(s) (e.g., cork), as discussed below. The flooring system 102 may include baffle material or insulation (not illustrated), for instance between the additional layer of flooring 166 and the subflooring 162. The flooring system 102 may additionally or alternatively include pads or sheets of material (not shown) that acoustically isolate sources of vibration (e.g., vibrating appliances such as washing machines).

The flooring system 102 uses non-toxic, natural materials that are intended to absorb the sound of footfalls and other vibrations, and provide isolation from exterior or interior sound.

Also for example, the habitable environment 100 may include a wall system 104 designed to achieve acoustic damping. The wall system 104 may include specially constructed walls which incorporate resilient channels 168, double-wallboard or sheetrock 170, double-studs 172, and acoustic insulation designed to decrease sound transmission. The resilient channels 168 resilient couple the double-wallboard or sheetrock 170 to the double-studs 172 to reduce transmission of vibration.

As another example, the habitable environment 100 may employ acoustically damping doors 108. For instance, solid oak doors that tightly seal to a door frame, may achieve sound reduction on par with well-constructed walls.

As a further example, the habitable environment 100 may employ acoustic damping windows 110. For instance triple glazed windows 110 with vacuum or rare earth gases trapped therebetween may minimize sound transmission from the exterior.

As yet a further example, the habitable environment 100 may employ acoustically damping plumbing insulation 174. For instance, non-toxic blankets of acoustically damping material 174 may be wrapped around water pipes (not shown) and air ducts 176 to reduce the sound transmitted by metal conduits.

The health effects of flooring have become the focus of a growing number of studies. Research shows that standing on surfaces without any give or cushioning for extended periods of time forces muscles into a constant state of flexion. This decreases circulation, promotes bad posture, causes lower back pain and can lead to orthopedic ailments. Cushioned mats decrease the impact on joints and promote muscle relaxation.

The habitable environment 100 may employ a cushion-lined flooring system 102 in order to realize a number of benefits, including increased circulation and promotion of healthy posture. The result may be fewer reports of joint pain, discomfort, and low energy. In addition, standing on softer surfaces decreases the risk of developing plantar fasciitis, and can alleviate symptoms for those already suffering from the condition. The flooring system 102 should be soft or resilient enough to allow for underfoot comfort, yet strong enough to improve lumbar support. The flooring system 102 consists of floating construction, for example with cork under layer(s) 166 to reduce forces generated from impacts by increased deflection.

Reflexology is a traditional practice of massage, which aims to reduce the symptoms of various ailments. Practitioners use stimulation of specific areas of the hands and feet to reduce tension and stress. Evidence has shown that the practice of reflexology has powerful anxiety reduction with reduced blood pressure and pulse rates. The habitable environment 100 may employ a custom-designed pathway (e.g., bathroom pathway), with textured floor covering 178, designed to improve blood circulation and general wellbeing by encouraging reflexology therapy.

Due to large surface area, floor finishing can often be a major source of VOCs. The habitable environment 100 uses natural flooring materials chosen to reduce the emissions of harmful indoor air pollutants and volatile organic compounds.

Electromagnetic fields (EMF) are created when charged particles are in motion. The movement of electrical charge through wires and appliances creates electromagnetic fields. The strength of the electric field depends on the voltage (e.g. typically 120 V for households) and is present near live wires, whether or not an electrical appliance is in use. Research suggests that long-term and significant occupational exposure to EMF may increase the risk of both Alzheimer's disease and breast cancer.

Thus, EMF shielding is incorporated into the habitable environment 100. The EMF shields are designed to block the spread of the field by creating a barrier composed of conductive or magnetic materials. EMF shields have traditionally been made out of solid metal, though this poses challenges regarding weight, corrosion, and malleability. Treated metal mesh or screens with openings smaller than the electromagnetic wavelength may provide a more practical solution.

Thus, for example the habitable environment 100 may include EMF shielding for wiring. In particular, wiring may be insulated with foil wraps designed to shield EMF from occupied parts of the habitable environment 100. Also for example, low EMF electrical wiring may be employed.

Another passive approach takes advantage of anti-bacterial or anti-pathogen (i.e., "treated") materials to reduce or eliminate the presence of bacteria or pathogens. The antibacterial or anti-pathogen materials may be incorporated into or deposited on bedding (e.g., sheets, bedspreads, throws, pillows, pillow covers) 180, window coverings (e.g., drapes, shades, curtains) 150 and/or surfaces (e.g., counters 181, tubs or shower stalls 122, table tops 120, walls 104). For example, various materials may be impregnated or coated with anti-bacterial or anti-pathogen materials. These materials may have opening or pore sizes on the order of 1 micron, providing an effective barrier against penetration by various undesirable particles. Any seams in the bedding should be sealed. At least in the case of bedding, these materials preferably completely encase or envelope mattress, box springs, pillows, and/or comforters. Such may provide protection against bedbugs, allergens, and/or dust mites.

Examples of suitable materials may contain or include, silver (Ag) in ionic form, which has proven effective against a variety of pathogens.

In order to reduce exposure to pathogens and toxins without excessive use of chemicals or cleaning, the amenities below lower the effort required in maintaining a healthy environment.

As a further example, titanium dioxide nanoparticles have emerged as an effective means of reducing air pollutants through a photocatalyst which creates a self-cleaning surface powered by ambient light exposure. For example, the nanoparticles may catalyze a reaction converting VOCs to harmless carbon dioxide. Such may be incorporated into a photo-catalytic coating which may be used on walls to break down bacteria, virus, and VOCs when exposed to light.

The habitable environment 100 may include anti-bacterial or anti-pathogen materials as structural materials. For example, cedar may be employed in closets and/or used as baseboards. Certain species of cedar act as a natural pest control, repelling many insects. Oils present in cedar wood have been shown to repel fungi (such as mold), bacteria, insects, termites, and ticks.

An ability to control a function or operation of at least the active components may be useful in realizing the amenities and benefits offered in the habitable environment 100. Thus, a number of user operable input/output (I/O) devices, controls, panels or kiosks 182 may be supplied.

For example, an in-room user operable I/O panel 182a may include a display (e.g., LCD) to display information. The in-room user operable I/O panel 182a may include user actuatable controls (e.g., user selectable icons displayed on touch screen, keys, buttons) manipulation of which allows a user, for instance an occupant of the habitable environment 100, to select parameters or programs to execute to control one or more of the environmental characteristics of the habitable environment 100.

Also for example, a mobile or handheld device 182b may serve as an I/O device. The mobile or handheld device 182b may include a display (e.g., LCD) to display information and user actuatable controls (e.g., user selectable icons, keys, buttons) manipulation of which allows a user, for instance an occupant of the habitable environment 100 or facility personnel, to select parameters or programs to execute to control one or more of the environmental characteristics of the habitable environment 100. The mobile or handheld device 182b may be owned by the end user, for example the occupant. The mobile or handheld device 182b may execute a downloaded customized application or "APP" that communicatively interfaces via a wireless protocol (e.g., IEEE 802.11, BLUETOOTH®, WI-FI®).

Alternatively or additionally, a remote user operable I/O controls, panel or kiosk 182c (FIG. 2) may include a display (e.g., LCD) to display information. The remote user operable I/O controls, panel or kiosk 182c may include user actuatable controls (e.g., user selectable icons displayed on touch screen, keys, buttons) manipulation of which allows a user, for instance personnel of the facility in which the habitable environment 100 is located, to select parameters or programs to execute to control one or more of the environmental characteristics of the habitable environment 100.

Information about the amenities and benefits afforded by the wellness system in the habitable environment 100 may be useful in realizing the benefits of such. Information may be provided via a server and presented via a variety of devices. For instance, information may be presented via a television 184 for instance on a dedicated channel, via in-room or other display, panel or kiosk 182a, via handheld device 182b, etc.

System and Subsystems

Figure 2:
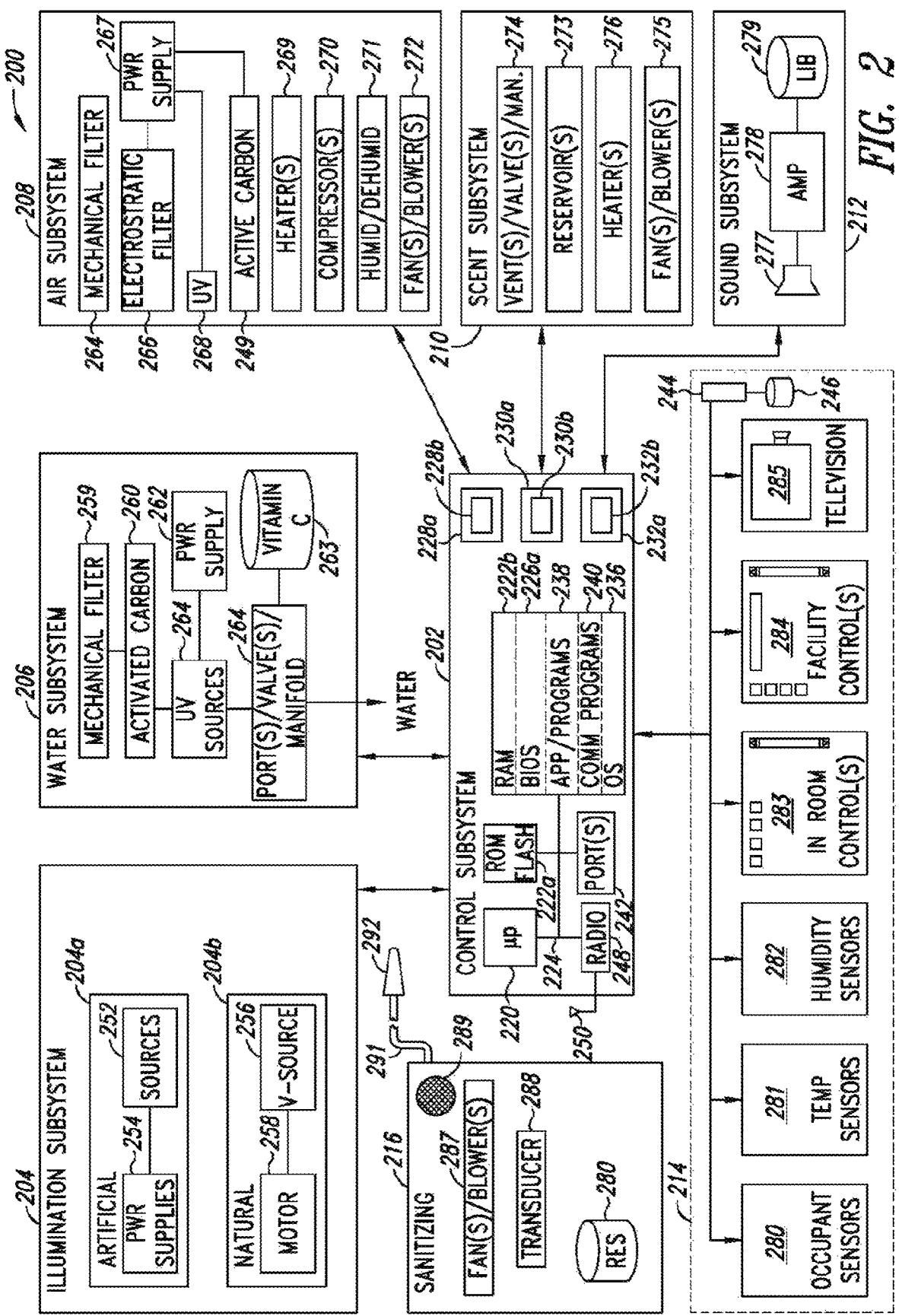
FIG. 2 is a block diagram that shows a portion of a habitable environment enhancement system to enhance a habitable environment, according to one illustrated embodiment.

FIG. 2 shows an active portion of an environmental control system 200 for controlling environmental characteristics of a habitable environment 100 (FIG. 1), according to one illustrated embodiment. FIG. 2 provides a more detailed representation of some of the components of FIG. 1.

The active portion of an environmental control system 200 includes a number of subsystems. For example, the active portion may include a control subsystem 202, illumination subsystem 204, water treatment subsystem 206, air treatment subsystem 208, scent subsystem 210, sound subsystem 212 input/output (I/O) subsystem 214. The active portion may optionally include a sanitizing subsystem 216, which as described below may be either build in or a fixture of the habitable environment 100, or may be portable, being located in the habitable environment 100 only during use. Each of the subsystems 202-216 and/or components are discussed in turn below with reference to FIG. 2. Operation of many of these subsystems 202-216 and/or components are discussed with reference to FIGS. 3-10 below.

The control subsystem 202 may take the form of a programmed computer or other processor-based system or device. For example, the control subsystem 202 may take the form of a conventional mainframe computer, minicomputer, workstation computer, personal computer (desktop or laptop), or handheld computer.

The control subsystem 202 may include one or more processing units 220 (one illustrated), nontransitory system memories 222a-222b (collectively 222) and a system bus 224 that couples various system components including the system memory 222 to the processing unit(s) 220. The processing unit(s) 220 may be any logic processing unit, such as one or more central processing units (CPUs), digital signal processors (DSPs), application-specific integrated circuits (ASICs), field programmable gate arrays (FPGAs), programmable logic controllers (PLCs), etc. Non-limiting examples of commercially available computer systems include, but are not limited to, an 80x86, Pentium, or i7 series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. The system bus 224 can employ any known bus structures or architectures, including a memory bus with memory controller, a peripheral bus, and a local bus. The system memory 222 includes nontransitory Flash or read-only memory ("ROM") 222a and nontransitory random access memory ("RAM") 222b. A basic input/output system ("BIOS") 226a, which can form part of the ROM 222a or RAM 222b, contains basic routines that help transfer information between elements within the control subsystem 202, such as during start-up.

The control subsystem 202 may include a hard disk drive 228a for reading from and writing to a hard disk 228b, an optical disk drive 230a for reading from and writing to removable optical disks 230b, and/or a magnetic disk drive 232a for reading from and writing to magnetic disks 232b. The optical disk 230b can be a CD/DVD-ROM, while the magnetic disk 232b can be a magnetic floppy disk or diskette. The hard disk drive 228a, optical disk drive 230a and magnetic disk drive 232a may communicate with the processing unit 220 via the system bus 224. The hard disk drive 230a, optical disk drive 230a and magnetic disk drive 232a may include interfaces or controllers (not shown) coupled between such drives and the system bus 224, as is known by those skilled in the relevant art. The drives 228a, 230a and 232a, and their associated computer-readable storage media 228b, 230b, 232b, may provide nonvolatile and non-transitory storage of computer readable instructions, data structures, program engines and other data for the environmental control system 200. Although control subsystem 202 is illustrated employing a hard disk 228a, optical disk 230a and magnetic disk 232a, those skilled in the relevant art will appreciate that other types of computer- or processor-readable storage media that can store data accessible by a computer may be employed, such as magnetic cassettes, flash memory, digital video disks ("DVD"), Bernoulli cartridges, RAMs, ROMs, smart cards, etc. The hard disk 228a may, for example, store instructions and data for controlling the other subsystems, for example based on specific aspects or characteristics of an occupant of the habitable environment 100 (FIG. 1), to provide environmental characteristics that promote the wellness or wellbeing of the occupant(s). The hard disk 228a may, for example, store instructions and data for presenting information about the various attributes and benefits provided by the active and passive components or measures, and instructions on how to use the environmental control system 200 and the passive components to maximize enjoyment, comfort, and well-being.

Program engines can be stored in the system memory 222b, such as an operating system 236, one or more application programs 238, other programs or engines and program data. Application programs 238 may include instructions that cause the processor(s) 220 to automatically generate signals to control various of the other subsystems to achieve various environmental characteristics in the habitable environment 100 (FIG. 1), for example based on one or more aspects, characteristics or attributes of an occupant thereof. Application programs 238 may include instructions that cause the processor(s) 220 to automatically receive input and/or display output via various user operable input/output (I/O) devices, controls, panels or kiosks 182 or television 184.

Other program engines (not specifically shown) may include instructions for handling security such as password or other access protection and communications encryption. The system memory 220 may also include communications programs 240, for example, a server for permitting the control subsystem 202 to provide services and exchange data with other subsystems or computer systems or devices via the Internet, corporate intranets, extranets, or other networks (e.g., LANs, WANs), as well as other server applications on server computing systems such as those discussed further herein. The server in the depicted embodiment may be markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers are commercially available such as those from Microsoft, Oracle, IBM and Apple.

While shown in FIG. 2 as being stored in the system memory 222b, the operating system 236, application programs 238, other programs/engines, program data and communications applications (e.g., server, browser) 240 can be stored on the hard disk 228b of the hard disk drive 228a, the optical disk 230b of the optical disk drive 230a and/or the magnetic disk 232b of the magnetic disk drive 232a.

An operator can enter commands and information (e.g., configuration information, data or specifications) into the control subsystem 202 via various user operable input/output (I/O) devices, controls, panels or kiosks 182 or television 184, or through other input devices such as a dedicated touch screen or keyboard (not shown) and/or a pointing device such as a mouse (not shown), and/or via a graphical user interface. Other input devices can include a microphone, joystick, game pad, tablet, scanner, etc. These and other input devices are connected to one or more of the processing units 220 through an interface such as a serial port interface 242 that couples to the system bus 224, although other interfaces such as a parallel port, a game port or a wireless interface or a universal serial bus ("USB") can be used. A monitor or other display device is coupled to the system bus 224 via a video interface, such as a video adapter (not shown). The control subsystem 202 can include other output devices, such as speakers, printers, etc.

The control subsystem 202 can operate in a networked environment using logical connections to one or more remote computers and/or devices as described above with reference to FIG. 1. For example, the control subsystem 202 can operate in a networked environment using logical connections to one or more other subsystems 204-214, one or more server computer systems 244 and associated nontransitory data storage device 246. The server computer systems 244 and associated nontransitory data storage device 246 may, for example, be controlled and operated by a facility (e.g., hotel, spa, apartment building, condominium building, hospital) in which the habitable environment 100 (FIG. 1) is located. Communications may be via wired and/or wireless network architectures, for instance, wired and wireless enterprise-wide computer networks, intranets, extranets, and the Internet. Thus, the control subsystem 202 may include wireless communications components, for example one or more transceivers or radios 248 and associated antenna(s) 250 for wireless (e.g. radio or microwave frequency communications, collected referred to herein as RF communications). Other embodiments may include other types of communication networks including telecommunications networks, cellular networks, paging networks, and other mobile networks.

Illumination (e.g., electromagnetic radiation or energy with wavelengths in the visible, near infrared (NIR) and/or near ultraviolet (NUV or UVA) portions of the electromagnetic spectrum) can have a significant effect on human health. As used herein and in the claims, the terms illumination or light include energy in the portions of the electromagnetic spectrum which are visible to humans (e.g., approximately 400 nm-approximately 700 nm) and not visible to humans (e.g., NIR or UVA). Light influences the human body in a number of unconscious ways. Metabolism has been deeply linked to the daily solar cycle through melatonin and the endocrine system. This cycle in the human body is called the circadian rhythm. Humans and animals have an internal clock that keeps the body on an approximately 24-hour cycle which matches the Earth's daily solar cycle, even in continuous darkness. Multiple bodily processes, from periods of alertness and sleep to digestion efficiency, are partially regulated by the intensity and color of light received by the eyes. However, light adjusts this internal timing to align the person to the Earth's daily solar cycle. Exposure to light comparable to the intensity of direct sunlight light will aid in resetting the circadian rhythm if it has been upset by shift work or long distance travel.

The intensity and color of light impacts different systems of the body. For example, blue light impedes the body's production of melatonin, a chemical messenger used to induce sleep. High intensities in the evening delay sleep, while light in the morning aids in waking. The appropriate brightness and color also contribute to alertness and concentration throughout the day. Melatonin is a natural antioxidant and counteracts the cancer-causing tendencies of free radicals. As a result, melatonin depletion from inappropriate exposure to bright lights leads to an increased risk of cancer. Bright light during midday and dimmer light at dinnertime aid in the digestion of carbohydrates.

Additionally, many individuals suffer from light-related mood irregularities, such as Seasonal Affective Disorder (SAD). Proper exposure to specific types of light at specific times addresses these irregularities. Exposure in the morning to gradual light brightening through dawn simulation has been shown to reduce depression. Daylight aids in the healthy development of eyesight. Myopia in children has been linked with low exposure to daylight and conversely, high reliance on dim artificial light. Age related macular degeneration, or the deterioration of eyesight with age, particularly in seniors with blue eyes can be minimized by reducing the exposure to high color temperature.

The illumination subsystem 204 may also be controlled to deliver light therapy, with or without topical photoactive substances. Such may, for example be used to treat a variety of conditions, for instance Seasonal Affective Disorder (SAD). People who live in high latitudes often experience depression during the winter as a result of long periods of reduced sunlight, a condition identified as SAD. For those affected by SAD, measures of sleep efficiency in the winter are noticeably different than those in the summer. Light therapy may be especially effective at treating SAD, producing results comparable to treatment with medication.

Another condition or syndrome commonly referred to as "jet lag" results from the relative shift between the circadian rhythm and the daily solar cycle. The effects are a disruption of sleep and a significant deterioration in mood, concentration, and cognitive performance. Controlled light exposure to help match the solar and circadian light cycles can help alleviate these symptoms.

In some individuals, the body's production or interpretation of melatonin slightly varies relative to the solar cycle, resulting in a set of symptoms identified as Delayed Sleep-Phase Syndrome (DSPS). Approximately one tenth of all adolescents and some adults find themselves falling asleep two to six hours after conventional bedtime. If left undisturbed, these individuals will often sleep soundly for approximately eight hours before waking in the middle of the day. Controlled lighting may help treat DSPS.

Emerging research indicates that different brain activity occurs when the human body is exposed to different parts of the light spectrum. Color can subconsciously affect people's abilities to do different types of tasks. For example, in one study, participants performed analytical tasks better in red light, and were more creative in blue-colored environments.

Research into workplace environments has found that people in brightly colored offices had higher measured emotional status than those in subdued or neutral surroundings. On the other hand, studies have shown that intense colors may be irritating to certain individuals. Chromotherapy employs illumination of certain wavelengths or combinations of wavelengths as an effective manipulator of mood given individual preferences. Practitioners use this therapy to address issues such as meditation, intuition, speech, nervousness and anxiety.

The illumination subsystem 204 may be operated to provide dynamic custom coloring throughout the habitable environment 100 (FIG. 1) or a portion thereof in order to provide chromotherapy. Additionally, the habitable environment 100 (FIG. 1) may optionally employ a chromotherapy wall wash in the form of a wall colored by light (e.g., via cover lights or sconces) that dynamically changes color to create a desired light spectrum for different settings and times of day. Additionally or alternatively, chromotherapy lighting can be added to specific areas where colored lights may be more desirable, such as meditation spaces and steam showers.

The illumination subsystem 204 discussed below is used to preserve and remediate the disruption of circadian rhythm, enhancing health, including the natural sleep cycle, the healthy development of the eyes among some attributes, and treating or alleviating the symptoms of various disorders, syndromes and/or afflictions. The illumination subsystem 204 may, for example, expose occupants or residents of a habitable environment 100 (FIG. 1) or a portion thereof to short periods of intense artificial light for therapeutic effects while subjects are awake as part of delivering light therapy.

The illumination subsystem 204 includes an artificial illumination subsystem 204a and a natural illumination subsystem 204b, which are operated in tandem to provide desired illumination in the habitable environment 100 (FIG. 1). In particular, the illumination subsystem 204 provides lighting in the habitable environment 100 (FIG. 1) with gradually adjusted color temperature and intensity to, for example improve circadian rhythm. As discussed below, the illumination subsystem 204 may implement a dawn simulator to gradually increase light and sound levels, which are designed to awaken the body when it enters a light stage of sleep. Such may replace standard alarm clocks producing a more natural environment to slowly wake from. Such may be realized by slow opening blackout shades or slowly allowing more light to pass through an electrochromatic pane over a wakeup period. Active sound may also be slowly increased in volume. Sounds may be those found in the natural environment or may be other sounds, such as music. Such may be realized in an integral unit, or via a dedicated bedside unit, which may provide for sounds as well as artificial lighting.

Also as discussed below, the illumination subsystem 204 may implement nightlights, employing dim (e.g., low-wattage) long wavelength LED or incandescent luminaires that engage in response to motion or ambient light levels, and are designed to sufficiently illuminate rooms for safe navigation without disturbing melatonin levels.

The artificial illumination subsystem 204a includes a plurality of illumination sources 252, and optionally one or more power supplies 254. As previously noted, the illumination sources 252 may take a wide variety of forms, for instance incandescent, florescent, compact florescent, or LED lights. LED lighting may be preferable since such is extremely energy efficient and may have a long operating life. The illumination sources 252, either alone or in combination, should be capable of selectively providing a broad range of intensities and a broad range of wavelengths. Such allows the illumination sources 252 to be selectively controlled to produce a wide variety of artificial illumination conditions, for instance conditions that mimic natural light, diurnal light patterns, circadian light patterns, light therapy patterns, and/or light patterns to accommodate for changes in location (e.g., latitude and/or longitude) or changes in season (e.g., spring, summer, autumn, winter). A circadian light pattern may be a pattern of light during a defined period of time (e.g., solar day, approximately 24 hours) which mimics the intensity and/or color of naturally occurring light (e.g., sunlight and darkness) for a given location (e.g., latitude and/or longitude) and/or at a given time of year (e.g., season, month). A produced or generated or provided circadian light pattern may be produced by a combination of artificial and naturally occurring light, which may be controlled to produce a defined or desired circadian light pattern. The defined or desired circadian light pattern may itself be different from a naturally occurring circadian light pattern at a particular location and/or time of year, or may simply be shifted relative to the naturally occurring circadian light pattern at a particular location and/or time of year. The illumination sources 252 may take the form of arrays of LEDs, each LED capable of producing one or more ranges of wavelengths. Wavelength of emitted light may be adjusted by varying a drive current supplied to LEDs. Thus, desired wavelengths may be achieved by selectively operating certain sets of LEDs (e.g., LEDS that emit in a given range of wavelengths), and/or by varying a current level supplied to any given LEDs. Intensity may be adjusted by selectively operating more or less LEDS, or by controlling power supplied to one or more LEDs via the power supply or supplies 254. For example, a duty cycle of a pulse width modulated (PWM) drive signal may be varied to adjust intensity out the output.

The power supply or supplies 254 may take a wide variety of forms, mostly dependent on the source of power (e.g., AC line current, DC), and the illumination sources (e.g., LEDs). The power supply or supplies 254 may include a transformer to electrically isolate the rest of the circuit from the source of power, and/or step down or step up a voltage. The power supply or supplies 254 may include a switch mode converter, operable to step down and/or step up a voltage. The power supply or supplies 254 may include one or more rectifiers (e.g., passive diode bridge, active transistor bridge of MOSFETs or IGBTs) to rectify AC power to DC power. Less likely, the power supply or supplies 254 may include one or more inverters, to invert DC power to AC power. The power supply or supplies 254 may include one or more dedicated power supply controllers, for instance a microcontroller such as a microprocessor, DSP, ASIC, PGA, or PLC and/or associated nontransitory computer- or processor-readable media. The power supply or supplies 254 is or are communicatively coupled to control a supply of electrical power to the illumination sources.

The natural light subsystem 204b may include one or more actuators, which are drivingly coupled to control an amount of natural light received in the habitable environment 100 (FIG. 1) via one or more windows 110. As previously discussed, the actuators may, for example take the form of an electrical power source 256 coupled to control a transmissivity of one or more electrochromatic panes or panels 146 (FIG. 1). As also previously discussed, the actuators may, for example take the form of an electric motor 258, solenoid or other element drivingly coupled that control a position of one or more window coverings 150 (FIG. 1) relative to the window, and thereby adjusting an amount of illumination that passes. The window coverings 150 may take the form of "blackout shades", that are automatically operated to shield an occupant or resident of the habitable environment 100 (FIG. 1) from outdoor light. The actuator 256, 258 may receive electrical power from a voltage source, or may receive control signals from a microcontroller. Electrochromatic panes or panels 146 (FIG. 1) may be capable of adjust (i.e., selectively substantially passing, selectively substantially blocking) ranges of wavelengths passed or block, as well as intensity of natural illumination passed or blocked. Thus, electrochromatic panes or panels 146 (FIG. 1) may be preferred over the window covering approach.

Controlling ingress of ambient light (e.g., sunlight, light from street lamps, buildings or signage, security lighting) from an exterior environment aids in management of exposure to levels of light in order to help maintain healthy circadian rhythms. This is particularly important during early summer mornings and long summer evenings, particularly at high latitudes (e.g., above or greater than approximately 40 degrees North or South) and/or urban environments.

Municipal water systems use many methods to control the purity of water. Although these methods generally succeed in bringing contaminant levels within national and state limits, water quality occasionally becomes an issue. For example, the Las Vegas sodium and sulfate levels in water would fail NYC city standards. In New York, byproducts formed by chlorination are near the federal limit. In response to these concerns, habitable environments 100 may use supplemental treatment technologies to bring contaminant concentrations well within the safety limits set by American regulatory agencies, as well as international safety standards.

New York City water is currently unfiltered, but a filtration plant is under construction for water drawn from the Croton Reservoir. Additionally, a UV sanitization facility is under construction for germicidal irradiation for the remaining water sources (Catskill/Delaware system).

Sediments-Solids of sulfates and chlorides can be suspended in water and produce a cloudy opacity, or turbidity. Water with high turbidity is not inherently unhealthy but elevated levels may be indicative of problems in the filtration process, which may imply that other contaminants have not been adequately removed. The coarse filters 259 reduce suspended solids in water. This is often the first stage of treatment, which optimizes performance of subsequent filters in the system.

Municipal water systems often add chlorine-based disinfectants to the water supply to remove bacteria. This affects water odor and taste, and causes potential irritation of the eyes. The human body contains beneficial symbiotic bacteria, which are necessary for the proper function of the skin and digestive tract. These microbes on the skin are harmed by chlorine. When chlorinated water comes into extended contact with organic matter, byproducts such as tri-halomethanes and halo-acetic acids can form, which are carcinogenic.

Pharmaceuticals and Personal Care Products (PPCP) comprise a myriad of different chemicals used as active ingredients in medications, cleaning products, and health supplies. PPCP enter the water system through multiple pathways, such as incomplete metabolism of drugs in the body, improper disposal of pills or personal care and cleaning products. Potentially unsafe levels of PPCP have accumulated in lakes and rivers, where they can enter municipal water systems. PPCPs are the likely cause of hermaphroditism in fish and lake amphibians, as well as other reproductive harm. Further contamination of water supplies is expected and increases in the quantity of PPCPs in the water are the subject of numerous research programs. The activated carbon water filters 260 that reduce disinfectant byproducts, pesticides, dissolved gases, chlorine, chloramine, and some pharmaceutical and personal care products, resulting in cleaner and better-tasting water. "Activated" charcoal filters contain a maze of passageways and openings, giving activated carbon some 1000 square meters of surface per gram.

Numerous forms of micro-organisms may be damaging to health or an indicator of poor water quality.

For example, coliforms are common, rod-shaped bacteria that are harmless in and of themselves. Like turbidity and suspended solids, coliforms act as indicators: their presence suggests that other, more dangerous microorganisms could survive water treatment and may be present in the supply. The EPA goal for coliforms is zero trace, but the enforceable limit allows 5% of all samples within a single month to test positive. New York City tested positive for 46 of 9958 samples taken in 2010 (or 1.3% of samples in the highest month).

Also for example, *Escherichia coli* (*E. coli*) bacteria are also rod-shaped bacteria, and the majority of strains are harmless. Some strains, such as O157:H7, cause food poisoning by excreting toxic chemicals that can be life threatening for vulnerable individuals. *E. coli* is transmitted as a result of eating unwashed or undercooked food. Infectious *E. coli* can also be found in water contaminated with fecal matter, such as agricultural runoff.

As further examples, *Cryptosporidium* and *Giardia* are single-celled microbes often found in water systems contaminated by sewage. Much larger than bacteria, these protozoa cause digestive problems, especially in vulnerable populations.

The water treatment subsystem 206 ensures that a supply of clean, healthy water is supplied to the habitable environment 100 (Figure) for example via taps such as the faucets 130, 136 (FIG. 1) or showerhead 132 (FIG. 1). The water treatment subsystem 206 may use a multi-step approach.

The water treatment subsystem 206 may include one or more mechanical filters 259. The mechanical filters 259 may include one or more sediment or coarse filters to filter sediment or larger particulate matter from the water. The mechanical filters 259 may include one or more fine filters to filter fine particulate from the water. Various types of coarse filter and/or fine filter media may be employed, including wire mesh screens, diatomaceous earth, ceramic water filter elements.

The water treatment subsystem 206 may include one or more activated charcoal filters 260. The activated charcoal filters may remove particulate in the size range of approximately 0.5 micrometers to 50.0 micrometers.

As an alternative to adding chemical disinfectants, water can be disinfected by irradiation with UV light. The high-energy light damages the DNA of microorganisms, making it less possible for them to reproduce. UV treatment is highly effective in clear, sediment-free water. Thus, the water treatment subsystem 206 may employ Ultra-Violet Germicidal Irradiation (UVGI), in an attempt to eliminate micro-organisms without using chemical-based filtering. In particular, the water treatment subsystem 206 may include one or more ultraviolet (UV) illumination sources 261 operable to expose the water to UV illumination of sufficient intensity and for sufficient time as to render pathogens in the water non-harmful. The UV illumination sources 261 may be supplied electrical power from one or more dedicated electrical power supplies 262.

As an alternative, a reverse osmosis system (not shown) preceded by a carbon filter may replace the sediment filter and ultraviolet irradiation for the removal of chlorine, PPCPS, disinfectant byproducts, heavy metals, microbes, and water hardeners.

The water treatment subsystem 206 may include one or more reservoirs of vitamin C 263 and one or more ports, valves, or manifolds 264 operable to release vitamin C into the water. The ports, valves, or manifolds 264 may be fluidly coupled to release vitamin C only in certain plumbing runs, for example supplying vitamin C only to water going to the showerhead 132 (FIG. 1) or optionally the faucet 130 associated with the tub or shower stall 122 (FIG. 1). An infusion of vitamin C into shower water may remove residual chlorine. In high concentrations, the skin can absorb vitamin C for example when applied as a topical cream. While these levels are significantly higher than those present in the showers, the shower water still provides the skin with small amounts of nutrients.

The air treatment subsystem 208 may include a variety of components to ensure that air supplied to the habitable environment 100 (FIG. 1) is healthy and comfortable for the occupant(s).

Good air quality is one of the most important features of a healthy environment. Stationary adults typically inhale 6 to 10 liters of air each minute. This amount doubles with moderate activity and doubles again with rigorous exercise. Approximately 15 cubic meters of air pass through the lungs of a moderately active adult each day.

Minute quantities of gaseous pollutants and particulates are present in the air from both natural and anthropogenic sources, which can cause serious health problems. Reducing the sources of gases and particulates in the home will decrease their negative effects. Airborne contaminants generated by materials, and the presence of individuals in the home, require expulsion through ventilation to the outdoors, and filtration to ensure that they do not return to the indoor air supply.

The major health effects of poor air quality are lung cancer and cardio-pulmonary disease. A significantly greater number of deaths from these ailments are attributable to periods of higher levels of particulate matter. Other effects of air quality are asthma attacks, emphysema, and interference with the immune system.

At the microscopic scale, natural laws concerning fluid dynamics and gravity work differently, allowing solids and liquids to float in the air almost indefinitely. Put broadly, this microscopic particulate matter is divided into two categories: fine particles, smaller than 2.5 μm ($PM_{2.5}$); and coarse particles larger than 2.5 μm and smaller than 10 μm ($PM_{10-2.5}$). Fine particles are inhalable particles that can lead to a number of health issues. Due to physical processes that govern their formation, fine particles are inherently more acidic and mutagenic than their larger counterparts. Fine particles are drawn deep into the lungs, maximizing damage. Most cases of mortality from inhalation of coarse particulate matter and larger contaminants arise from toxic chemicals they contain rather than the particles themselves.

Coarse particles do not penetrate as deeply into the lungs as fine particles, and therefore are the less dangerous of the two. However, many coarse particles are allergens. For example, dust mites are microscopic arachnids that feed on pet dander, dead human skin cells, and other biological matter. They thrive in carpets, mattresses, and curtains, and tend to dwell in synthetic fibers rather than natural materials. Mites are not inherently dangerous, but their droppings contain chemicals that trigger an immune response in some individuals. The resulting symptoms often include itchy eyes, runny nose, and wheezing, a reaction that can be particularly debilitating for asthmatics. Nearly one quarter of American homes have dust mite levels associated with symptomatic asthma, and almost half contain enough dust mites to cause allergic reactions in susceptible individuals.

The air treatment subsystem 208 may include one or more mechanical air filters (e.g., mesh, screen, woven, or piled material) 265, through which air passes to remove larger particulate. Suitable mechanical air filters may include an activated carbon air filter, high efficiency particulate (HEPA) air filter (i.e., MERV equivalent 17+), MERV 13-16 air filter, a quantity of Zeolite, or a porous material.

The air treatment subsystem 208 may include one or more electrostatic filters or precipitators 266 to remove fine particulate. In particular, electrostatic filter(s) 266 trap particles that could contain allergens, toxins, and pathogens. In addition, the electrostatic filter(s) 266 are installed to reduce dust mites, pollen, carpet fibers, mold spores, bacteria, smoke, and diesel particulate matter from the air. The electrostatic filter(s) 266 attracts particles using an electrostatic charge and extracts them from the air into a wire mesh.

The electrostatic filters 266 may take a variety of forms, for instance ones which place a charge on particles and an opposite charge on a screen or other electrode element to attract the charged particles. An example of such is a corona discharge type of electrostatic filter. The electrostatic filter 266 may be supplied charge via an electrical power supply 267.

Various airborne pathogens may present problems, particularly in enclosed spaces or habitable environments. This may be of particular concern with newer construction techniques which are employed to reduce the exchange of air with the exterior environment, for instance to reduce heat loss and thereby increase thermal efficiency. Although most airborne microbes are pervasive and generally harmless, some can be dangerous pathogens easily spread throughout a home's ventilation system.

Mold spores can induce skin, nose, throat, and eye irritation, and trigger asthma attacks. These fungi release volatile organic compounds that produce the characteristic "moldy" odor and have been linked to dizziness and nausea. Humidity control has been proven effective in reducing mold, and insulated windows reduce condensation so as to prevent mold from growing in nearby joints.

Individual microbes are very small and can evade some filters if not attached to other particles. In order to reduce the probability of airborne pathogens from traveling through the enclosed space or habitable environment 100 (FIG. 1), UVGI can be used to provide additional protection. UVGI is based on a specific frequency of UV light that specifically targets the DNA of microbes and viruses passing through the ventilation system.

The air treatment subsystem 208 may include a UV air sanitizer designed to disinfect air via UV light within one or more components (e.g., ducts) of a ventilation system. The aim is to sterilize airborne bacteria, viruses, dust mites, and mold spores that may have escaped filtration.

Thus, the air treatment subsystem 208 may include one or more UV illumination sources 268. The UV illumination source(s) 268 is positioned to illuminate air with UV illumination of a sufficient intensity for a sufficient time as to render pathogens non-harmful.

Various gaseous pollutants may produce harmful effects in humans, particularly where allowed to accumulate in habitable enclosed spaces. Volatile Organic Compounds (VOCs) are carbon-based chemicals that evaporate into gases at room temperature. Many paints, cleaning products, and pest control chemicals emit VOCs, whose presence in buildings is 2 to 5 times as high as outside levels. Some furniture and building materials also slowly release some kinds of VOC, such as formaldehyde. In the short term, exposure can cause dizziness, nausea, headaches, throat irritation, and fatigue, while chronic effects include damage to the liver, kidneys, and central nervous system.

Nitrogen dioxide is a product of combustion and mainly found near burning sources. Indoor areas that contain gas stoves, fireplaces, and cigarette smoke often have a much higher concentration of nitrogen dioxide. Epidemiological studies suggest that excessive nitrogen dioxide inhalation may decrease lung function, particularly in children. In the short term, it can also trigger allergic responses from the immune system, resulting in irritation of the eyes, nose, and throat.

Ozone is created by reactions between molecular oxygen, nitrogen oxides, and sunlight. It is the major catalyst in the formation of smog. Ozone impedes cellular respiration, resulting in reduced cell activity. High concentrations of inhaled ozone can result in an itchy throat and chest tightness; chronic exposure scars the lung tissue, which can lead to emphysema. In addition, ozone interferes with the body's immune system, which compounds the danger from air or water-borne pathogens. Under current standards, the E.P.A. expects ozone to cause more than 110,000 lost work days and 1,100,000 lost school days between 2008 and 2020.

The design of the habitable environment 100 (FIG. 1) avoids or at least reduces the use of materials which emit VOCs, for example omitting or avoiding products or materials containing certain glues or resins (e.g., particle board). In day-to-day use, materials which emit VOCs are also avoided. For instance, the care or maintenance of the habitable environment 100 (FIG. 1), avoids the use of cleaning compounds which are known to result in VOC emission.

Nevertheless, some VOCs and other gaseous pollutants may appear in the habitable environment. Thus, the air treatment subsystem 208 may include one or more activated carbon air filters 249 in the flow path to reduce VOC, nitrogen dioxide, and ozone that pass through activated carbon media filters designed to intercept gas molecules. Activated carbon air filters 249 are most useful in areas with sources of fumes or odors.

Additionally or alternatively, the electrostatic filter 266 or some other element may optionally include one or more catalysts selected to catalyze certain impurities in the air. For instance, the electrostatic filter 266 may include one or more catalysts (e.g., non-metal catalysts for instance: titanium dioxide, chromium oxide or aluminum oxide, or metal catalysts for instance: Fe, Co, Ni, Cu, Ru, Rh, Pd, Ag, Ir, Pt and Au, as well as combinations or alloys thereof, such as an alloy of Pt and Rh) to catalyze species of VOCs into more acceptable or less harmful forms.

The air treatment subsystem 208 may include one or more heaters 269 to heat air. The heaters 269 may take any of a large variety of forms. Heaters 269 may take the form of various electric heaters, which employ a resistive radiant element to heat air. Heaters 269 may take the form of forced air heaters which typically include burners that burn a fuel such as natural gas or propane. Heaters 269 may alternatively take the form of oil furnaces, or the like.

The air treatment subsystem 208 may include one or more compressors 270 which may form part of an air conditioner cooling unit. The compressors 270 may be fluidly coupled to control pressure of a fluid, coupled with one or more coils or other heat exchangers, and may operate in a similar fashion to standard air conditioner units to remove heat from the air.

Relative humidity is the measure of water vapor in the air compared to the total amount that can be held at a given temperature. In the spring and summer months, humidity levels can be high enough to cause discomfort. When cool air flows through central air systems, humidity in the air is reduced, since cooler air holds less water vapor. However, as dry air is drawn in and heated within a building in the winter, relative humidity falls, so the air feels dry.

To maintain comfort, and prevent the establishment and growth of mold, dust mites, and bacteria, relative humidity in the habitable environment 100 should be kept between 30% and 50%. Using high-temperature water within the ventilation system of the home suppresses bacteria growth. Humidity towards the bottom of this range is better in terms of air quality, but extremely low moisture levels may lead to dry skin and respiratory irritation.

Thus, the air treatment subsystem 208 may include a humidifier and/or dehumidifier 271 which controls humidity throughout the enclosed habitable environment 100 (FIG. 1). This is particularly important when moisture levels in the air fall in winter, thus the air treatment subsystem 208 must increase the moisture (i.e., humidify) during dry periods. Conversely, the air treatment subsystem 208 lowers moisture (i.e., dehumidifies) during humid periods. The humidifier and/or dehumidifier 271 may include a reservoir (not shown) that retains water to either be added to the air in a humidification mode or removed from the air in a dehumidification mode. The humidifier and/or dehumidifier 271 may include a compressor (not shown) used to, for example cool air as part of removing moisture. The humidifier and/or dehumidifier 271 may optionally include a heating element to heat air as part of adding moisture.

To control relative humidity, the air treatment subsystem 208 may additionally employ exhaust vents 158*a* (FIG. 1), particularly in the bathroom 100*b* (FIG. 1) used to increase the ventilation rate in that portion of the habitable environment in order to rapidly lower humidity generated therein, for example from showers 122, 132 (FIG. 1).

The air treatment subsystem 208 may include one or more fans and/or blowers 272 coupled to one or more ducts (FIG. 1) and/or vents (FIG. 1). The fans and/or blowers 272 may circulate air within the air treatment subsystem 208 and/or within the habitable environment 100 (FIG. 1). The fans and/or blowers 272 may expel air to an exterior environment and/or draw fresh air from the exterior environment, prior to treating the fresh air. In particular, a high flow ventilation system expels indoor air to reduce the buildup of internally generated air impurities such as volatile organic compounds, dust mites, and pet dander. A heat exchanger may advantageously be employed to recover energy from the outgoing air.

As an alternative for humidity control, a waterfall (not shown) in the enclosed space can both increase and decrease the relative humidity. When chilled water is circulated in the waterfall, the system absorbs water vapor from the air. When room temperature or warm water is circulated in the waterfall, the system releases water vapor into the air. The waterfall may also provide a soothing background sound in the habitable environment 100.

The practice of aromatherapy employs a wide variety of oils and extracts, with differing effects on mood and emotion. Supporters of contemporary aromatherapy practices suggest that various fruit and plant-based aromas have the ability to positively affect mood, behavior, and perceptions of wellness. Examples of plant-based scents and their corresponding benefits include:

Lavender effects include restful sleep during exposure at night, increased vigor the morning after nighttime exposure enhanced mood, decreased heart rate and increased positive mood. Jasmine effects include relaxation, decreased heart rate and increased positive mood. Orange scent has been used to reduce anxiety and help maintain better mood in stressful circumstances. Rosemary has been shown to enhance memory and increases reaction times.

The scent subsystem 210 is operable to selectively dispense or disperse one or more scents into the air in the habitable environment 100 (FIG. 1) or a portion thereof. The scent subsystem 210 may include a number of reservoirs 273 which hold various scents (e.g., lavender, rosemary), typically in a liquid form. One or more vents, valves or manifolds 274 are selectively operable to fluidly communicably couple selected ones of the reservoirs to emit or disperse scent into the habitable environment 100 (FIG. 1) or a portion thereof, for example via ducts or vents of the air treatment subsystem 208. The scent subsystem 210 may optionally include one or more fans and/or blowers 275 to assist in dispersing the scent(s) into the habitable environment 100 (FIG. 1) or a portion thereof. The scent subsystem 210 may optionally include one or more heaters 276, thermally (e.g., conductively, radiantly, convectively) coupled to the reservoirs 273 or an output of the reservoirs 273 to heat and thereby vaporize liquid forms of the scent(s) into a gaseous form more easily dispersible into the habitable environment 100 (FIG. 1) or a portion thereof.

Additionally or alternatively, one or more passive components may be employed to diffuse scents into the habitable environment 100. For example, various items or objects may be impregnated with specific scents. Such items or objects may include various fabrics, such as curtains, linens or bedding (e.g., pillow cases, pillows, sheets, blankets, comforters, duvets), carpets, towels, etc. Such items may include a pouch, sack or other breathable encasement or enclosure, which may be positioned at various locations about the habitable environment 100, for instance in a flow path of a vent or within a pillow case. The pouch or sack may be distributed in an air-tight packet, container or envelope which is opened immediately prior to use. Such may advantageously maintain the scent emitting materials fresh between manufacture and use, and may prevent undesired scents from being emitted into the habitable environment. Thus, certain packets may be opened to customize the scent to a specific occupant or occupants of the habitable environment 100, and the scent(s) allowed to disburse or disperse through the habitable environment 100.

Thus, active or passive components of a scent subsystem 210 deliver room-specific aromatherapy based on the room's function and aroma benefit. A wide variety of essential oils and crafted aromas are available for use in the dispenser with the option to tailor to individual specifications.

The sound subsystem 212 provides sound into the habitable environment 100 (FIG. 1) or a portion thereof. In particular, the sound system may, for example, provide soothing sounds (e.g., running water, forest sounds, waves, "white" noise, "pink" noise, music). The sound subsystem 212 may include one or more speakers 277, which may be positioned throughout the habitable environment 100 (FIG. 1) or a portion thereof. Sounds may be selected to produce relaxation or to allow an occupant to focus more intently than the occupant would focus without the sounds, for example while reading or working. The sound subsystem 212 may include one or more amplifiers 278 electrically, optically or wirelessly coupled to provide signals to the speakers 277 (e.g., typically analog or digital electrical signals) that cause the speakers 277 to reproduce the sounds represented by the signals. The sound subsystem 212 may optionally include a nontransitory computer- or processor-readable storage media 279 that stores digital versions of the sounds, for example in a library. The amplifier 278 may include one or more CODECs and/or microcontrollers to convert the digital versions of the sounds into signals for controlling the speakers 277. The sound subsystem 212 may include one or more microphones (not shown) to detect noise in the habitable space. The sound subsystem 212 may provide masking sound to offset or cancel the noise.

The input/output (I/O) subsystem 214 is communicatively coupled to the control subsystem 202 to supply input thereto and/or to provide output therefrom. The input/output (I/O) subsystem 214 may include various sensors 280-282, user operable input/output (I/O) devices, controls, panels or kiosks 283, 284, and other devices or components such as televisions 285.

For example, one or more occupant sensors or detectors 280 may be positioned in, or proximate the habitable environment 100 (FIG. 1) or portions thereof. The occupant sensor(s) or detector(s) 280 sense or detect a presence, or conversely an absence, of an occupant in the habitable environment 100 (FIG. 1). The occupant sensors or detectors 280 may take any of a large variety of forms. For example, the occupant sensor(s) or detector(s) 280 may take the form of various motion detectors, for instance passive infrared based motion detectors, proximity (RF) based motion detectors, microwave or radar based motion detectors, ultrasonic based motion detectors, vibration based motion detectors, and/or video based motion detectors. The occupant sensor(s) or detector(s) 280 may include simple contact switches which detect movement or operation of a fixture or some other element (e.g., turning on a radio, television, stereo, appliance) by an occupant. The occupant sensor(s) or detector(s) 280 may take the form of simple cameras (e.g., digital camera) which may capture images, from which changes from frame to frame may indicate a presence or absence of an occupant. The occupant sensor(s) or detector(s) 280 may detect a presence or absence of an object associated with the occupant, for instance a smartcard or keycard, or a handheld or mobile device.

Also for example, one or more temperature sensors or detectors 281 may be positioned in, or proximate the habitable environment 100 (FIG. 1) or portions thereof. The temperature sensor(s) or detector(s) 281 sense or detect a temperature proximate the temperature sensor or detector and provides signals to the control subsystem 202 and/or air treatment subsystem 208 indicative of the sensed or detected temperature. The temperature sensor(s) or detector(s) 281 may employ various components, for example thermocouples or thermally responsive resistors.

Also for example, one or more humidity sensors or detectors 282 may be positioned in, or proximate the habitable environment 100 (FIG. 1) or portions thereof. The humidity sensor(s) or detector(s) 282 sense or detect humidity or relative humidity proximate the humidity sensor or detector 282 and provides signals to the control subsystem 202 and/or air treatment subsystem 208 indicative of the sensed or detected humidity. The humidity sensor(s) or detector(s) 282 may employ various components.

One or more in-room user operable input/output (I/O) controls, panels or kiosks 283 may allow an occupant or facility personnel (e.g., cleaner, maintenance) to interact with the environmental control system 200. The in-room I/O control(s), panel(s) or kiosk(s) 283 may include a touch-sensitive or touch-responsive display, which allows presentation of information and a graphical user interface (GUI). The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment. The GUI may present the user with a set of defined programs to select from, the programs. The programs may be presented in a simple fashion with simple labels or names, yet may have fairly complicated sets of settings for various combinations of the subsystems 202-214.

The in-room user operable I/O control(s), panel(s) or kiosk(s) 283 may also allow collection of information from an occupant which is indicative of the occupant's impressions and overall satisfaction with the habitable environment 100, and particularly the health and wellness amenities. Such may be captured with an automated survey, which includes various questions and possible ratings, presented for instance via a graphical user interface (GUI).

One or more facility user operable I/O controls, panels or kiosks 284 may allow facility personnel (e.g., clerk, concierge, cleaner, maintenance personnel) to interact with the environmental control system 200. The facility I/O control(s), panel(s) or kiosk(s) 284 may include a touch-sensitive or touch-responsive display, which allows presentation of information and a GUI. The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment. The GUI may present the user with a set of defined programs to select from, the programs. The programs may be presented in a simple fashion with simple labels or names, yet may have fairly complicated sets of settings for various combinations of the subsystems 202-214. The GUI may optionally allow facility personnel to define new programs, delete old programs, and/or modify existing programs.

The GUI may, for example, allow facility personnel to enter information about a specific guest or other occupant that will occupy a respective habitable environment. Information may, for example, include a location from which the occupant originated. The location may be specified in a variety of forms including name (e.g., city, state, country), geographic coordinates (e.g., latitude and/or longitude). Such may allow the environmental control system 200 to determine a control program that accommodates for changes experienced by the occupant due to travel to a new location. Thus, the environmental control system 200 may adjust for changes in the diurnal cycle and/or circadian cycle. Information may include an age or approximate age of the occupant, which may affect or be related to circadian cycle and the ability to adjust for travel (e.g., "jet lag"). Such may allow accommodation or treatment for other issues, for instance seasonal affective disorder, or providing light therapy to treat certain aliments or symptoms.

As noted previously, one or more televisions 285 may be used to at least present information to an occupant. In some implementations, a control such as a remote control, may be used by the occupant to interact with the television 285 to make selection of various user selectable options for controlling one or more components of the environmental control system 200. As also previously noted, an occupant may use a handheld or mobile device 182*c* (FIG. 1), such as a smart phone, tablet computer, etc. to interact with environmental control system 200.

The server 244 and nontransitory computer- or processor-readable medium 246 may store and provide information to other components of the environmental control system 200. Such may, for instance, include a schedule that specifies which occupants will occupy which habitable environments 100 (FIG. 1) of the facility, and at what times. This information may also specify, or be mapped to, information which specifies desired environmental characteristics for the respective occupants. Thus, the environmental control system 200 may automatically adjust environmental characteristics in a variety of habitable environments 100, customized for the particular occupant.

A sanitizing subsystem 216 may be an integral part of the habitable environment 100, or may be selectively provided thereto or therein, for example when preparing for another occupant or guest. For instance, the sanitizing subsystem 216 may be provided as a cart with wheels, as illustrated in FIG. 2, for selectively being wheeled into the habitable environment 100. While illustrated as a cart, the sanitizing subsystem 216 may be provided as a portable unit which may be hung from a pole mounted approximately centrally in the habitable environment, or wall or less preferably hung from a wall or other structure in the habitable environment 100. Such may advantageously allow the sanitizing subsystem 216 or a portion thereof to be positioned at a higher point than might otherwise be achieved via a cart.

The sanitizing subsystem 216 may provide a sanitizing agent into the habitable environment 100 to destroy or render non-harmful various pests or pathogens. The sanitizing subsystem 216 may optionally evacuate the sanitizing agent from the habitable environment 100 (FIG. 1), after a sufficient time has passed for the sanitizing agent to destroy or render non-harmful the pests or pathogens.

The sanitizing agent may take a variety of forms. The sanitizing agent may be in a gaseous form, or may be a vapor or "dry vapor" (i.e., non-wetting) form. Suitable sanitizing agents may, for example, include forms of chlorine dioxide, peracetic acid, hydrogen peroxide and electrochemically activated solutions (e.g., electrolyzed water). Suitable sanitizing agents may, for example, include photocatalytic antimicrobial materials (e.g., composite photocatalyst, nanoparticle sized zinc metal in a matrix of nano-crystalline titanium dioxide available under the trademark OXITITAN™ from EcoActive Surfaces, Inc. of Pompano Beach, Fla.). Such may provide an antimicrobial surface, reduce odor and VOCs, provide for hydrophilic or hydrophobic self-cleaning, and/or UV or corrosion protection. The UV protection may be particularly advantageous where UV illumination is also utilized in sanitizing the habitable environment 100.

Alternatively, or additionally, the sanitizing agent may be in the form of electromagnetic energy or radiation, for example specific ranges of wavelengths such as UV of electromagnetic energy.

A sanitizing subsystem 216 may include one or more reservoirs of sanitizing agent(s) or materials 286 which when combined produce a sanitizing agent. The sanitizing subsystem 216 may include one or more fans or blowers 287 to assist in dispersing the sanitizing agent into the habitable environment 100 (FIG. 1). In some implementations, the fan(s) or blower(s) 287 also assist in removing or evacuating the sanitizing agent into the habitable environment 100 (FIG. 1). The sanitizing subsystem 216 may optionally include one or more transducers 288 operable to place the sanitizing agent in a form more amenable to dispersion. The transducer(s) 288 may take the form of a heater, for example to vaporize the sanitizing agent. Additionally or alternatively, the transducer(s) 288 may take the form of one or more high frequency vibration elements (e.g., piezoelectric element) to pulverize or otherwise particalize either dry sanitizing agent into a very fine particulate form or to break up droplets of liquid sanitizing agent into a very fine form, for instance that does not wet surfaces. Other types of transducers 288 may be employed.

The sanitizing subsystem 216 may include one or more ports or vents 289 for dispersing the sanitizing agent. Ports or vents 289 may be built into a housing 290 of the sanitizing subsystem 216. Additionally, or alternatively, the sanitizing subsystem 216 may include one or more hoses 291 with nozzles 292 or other openings for dispersing the sanitizing agent.

The sanitizing subsystem 216 may include one or more wands selectively operable to emit electromagnetic energy or radiation, for example specific ranges of wavelengths such as UV of electromagnetic energy. The wand(s) may include one or more illumination sources, for instance UV illumination sources and may be electrically coupled to a power source 297 carried by the cart via one or more cables 298. Alternatively, illumination sources may be located in the cart, and the wand(s) optically coupled thereto via one or more cables 298.

The sanitizing subsystem 216 may include one or more illumination sources positioned so as to be exposed to the ambient environment in order to provide illumination into the habitable environment 100 directly from a housing of the sanitizing subsystem 216. The illumination sources positioned on an exterior of the cart or within the exterior of the cart and optically communicatively coupled to the exterior via one or more optical ports (not shown). This may allow the general habitable environment 100 to be optically treated, for instance with UV illumination. The wand(s) may, for instance, be used to treat areas or spaces that would not otherwise be treated via direct illumination from the illumination sources, for instance areas or spaces that are not in a direct line of sight of the illumination sources. In some implementations, the illumination sources may provide the illumination which is optically coupled to the wand(s) via the cable 298.

Sanitizing may require as little as three hours of exposure to UV illumination, dependent of a variety of factors such as type of pathogens, distance, and intensity (e.g., incident energies). Targeted pathogens may take a variety of forms, for example mold spores, and organisms such as various *bacillus*, protozoa, virus, yeast. Mold spores may include, for instance: *Aspergillius flavis, Aspergillius glaucus, Aspergillius niger, Mucor racemosus* A, *Mucor racemosus* B, *Oospora lactis, Penicillium expansum, Penicillium roqueforti, Penicillium digitatum, Rhisopus nigricans*. Illumination may occur before, after, during, or before and after application of a photocatalytic antimicrobial agent or coating. Operation may require that the habitable space be vacant during the entire period of treatment. Thus a remote control (e.g., wireless handheld transmitter and wireless receiver in the cart 203) or a delay start timer may be advantageously employed.

Data, Data Structures, and Nontransitory Storage Media

Various nontransitory media discussed above may store information such as data including configuration information in one or more data structures. Data structures may take a variety of forms, for example records associated with relational databases, a database itself, lookup tables, etc. The data structures may store a variety of different information or data.

Operation

Figure 3:
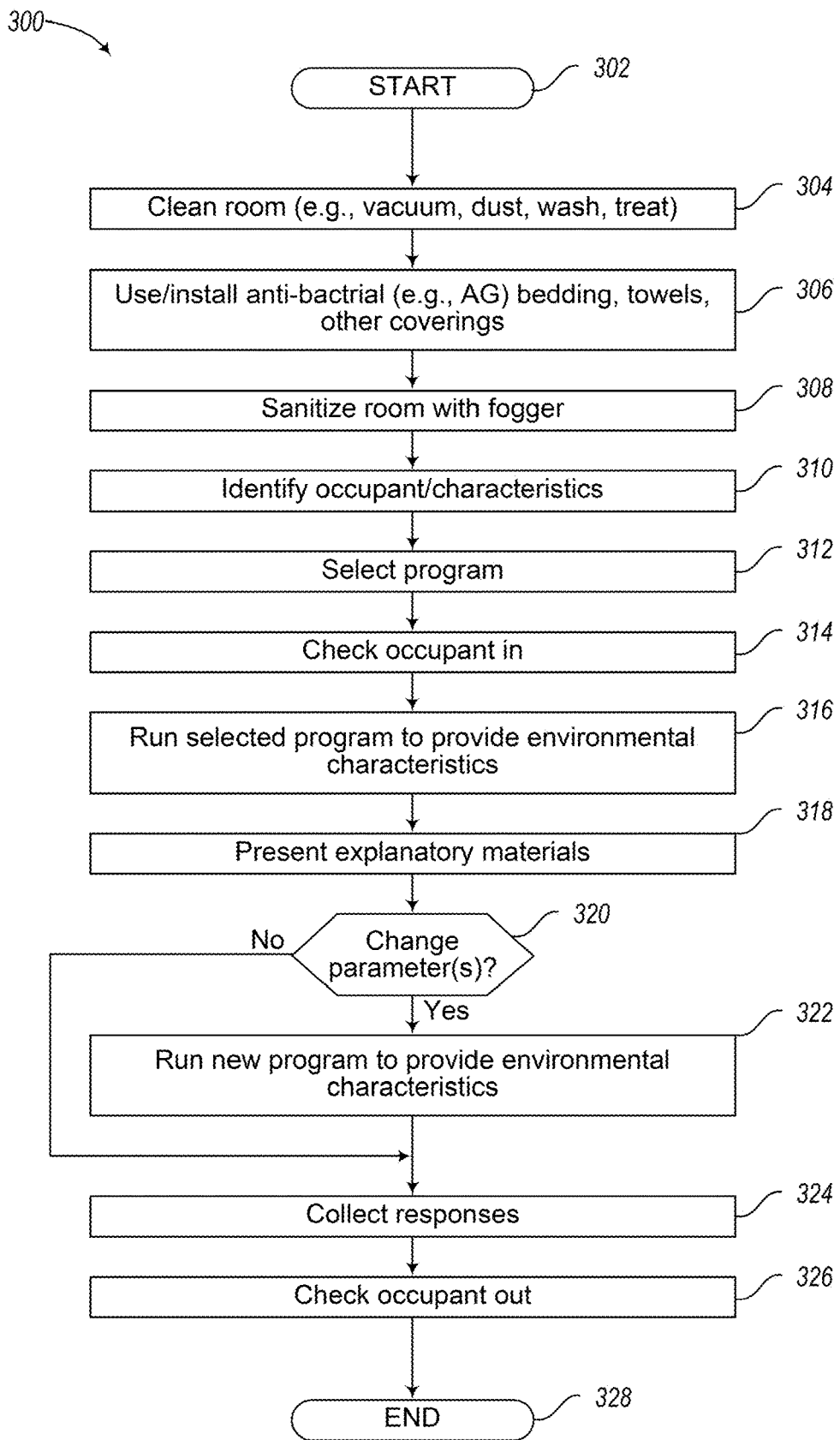
FIG. 3 is a flow diagram that shows a high level method of providing an enhanced environment in a habitable environment, according to one illustrated embodiment.

FIG. 3 shows a high level method 300 of providing an enhanced environment in a habitable environment 100, according to one illustrated embodiment. While often discussed in terms of a hotel, motel, spa or other hospitality environment, the habitable environment 100 may take the form of a home, office, hospital or any other inhabitable environment.

The method 300 starts at 302. The method 300 may, for example start on a periodic basis, for instance daily, weekly, or monthly. Alternatively, or additionally, the method 300 may start on demand, for instance in response to a checking in of a guest, or expected check in of a guest, or an entry of a guest or occupant into the habitable environment 100 (FIG. 1), for instance in response to reading an identifier from a smartcard or cardkey 114.

At 304, cleaning personnel clean the habitable environment 100. Such may include emptying waste receptacles, dusting, washing, vacuuming, cleaning and/or treating surfaces with disinfectants, and/or collecting soiled or used laundry (e.g., towels).

At 306, cleaning personnel use or install anti-bacterial bedding, towels, other coverings (e.g., drapes) in the habitable environment 100. The anti-bacterial bedding, towels, other coverings may for example be impregnated or coated with one or more anti-bacterial or anti-pathogen agents.

At 308, cleaning personnel optionally sanitize the habitable environment 100 or a portion thereof, for instance with a sanitizing subsystem 216. As previously explained, the sanitizing subsystem 216 may take a variety of forms, at least one of which is a fogger or "dry fogger" which disperses a fog or "dry fog" of a sanitizing agent into the habitable environment 100 (FIG. 1). The sanitizing agent may deposit on various surfaces, and may be left in place sufficiently long to neutralize or render pathogens or other undesirable substance harmless. As previously noted, the sanitizing agent may not "wet" the surfaces, thereby protecting the surfaces from damage. The sanitizing system 216 may then, optionally evacuate or otherwise remove the sanitizing agent from the habitable environment 100, for instance collecting such in a reservoir for disposal or recycling.

Optionally at 310, the environmental control system 200 or a portion thereof identifies one or more occupants or guests that will inhabit the habitable environment 100 (FIG. 1) and/or specific attributes, traits or characteristics of the occupant(s). For example, facility personnel may enter an occupant identifier via an input device, panel or kiosk 284. Also for example, the occupant(s) or guest(s) may enter an occupant identifier via an input device, panel or kiosk 283. As a further example, an occupant identifier may be automatically read from some piece of media, for instance a smartcard or keycard. The occupant identifier may, for example, be encoded in a magnetic stripe, machine-readable symbol, or wireless transponder (e.g., RFID transponder) of the smartcard or keycard. The occupant identifier may consist of or include the occupant's name, however preferable is an alphanumeric string which does not include the occupant's actual name. The alphanumeric string may be logically associated with the occupant's name, for example in a secure database or other secure data structure. Such an approach may enhance security.

The specific attributes, traits or characteristics of the occupant(s) may likewise be stored in a secured database or other secure data structure, or less preferably could be stored in the smartcard or cardkey. The specific attributes, traits or characteristics of the occupant(s) may specify information that allows customization of the habitable environment to the needs or desires of the occupant. For example, the specific attributes, traits or characteristics of the occupant(s) may identify one or more air temperatures, for example air or room temperatures for different times throughout a daily cycle. Also for example, the specific attributes, traits or characteristics of the occupant(s) may identify one or more air relative humidities, for example relative humidity for different times throughout a daily cycle. As another example, the specific attributes, traits or characteristics of the occupant(s) may identify one or more locations from which the occupant has traveled. Such may permit adjustment of, for example lighting, to accommodate for jet lag, SAD, etc. As a further example, the specific attributes, traits or characteristics of the occupant(s) may identify one or more syndromes, ailments or conditions for which environmental characteristics may be adjusted to alleviate or treat. These may include syndromes, ailments or conditions which may be addressed by delivery of illumination (e.g., timed delivery of different intensities and/or wavelengths). This may also include syndromes, ailments or conditions which may be addressed by delivery of humidity, for instance various skin disorders or problems. These syndromes, ailments or conditions may be specified by name or an assigned identifier. Alternatively or additionally, specific instructions or patterns may be stored for providing the desired environmental characteristics. Such may help maintain privacy for individuals, and may address regulatory issues (e.g., HIPAA) related to the care, handling and management of health-related information such as electronic medical records. Thus, for example, a pattern of illumination which specifies wavelengths and intensities at various times throughout the solar day may be stored. Patterns specifying air temperature, relative humidity, sound, scents, and other ambient environmental characteristics may likewise be stored for various times throughout the solar day. These patterns may be synchronized with one another. Thus, for example, illumination and sound may be synchronized to produce a gradual wakeup period in which light gradually increases in intensity as does soothing sounds. The wavelengths of light may likewise gradually change during this wake up period. Also for example, illumination and sound may be synchronized to produce a gradual relaxation period prior to a sleep time in which light gradually decreases in intensity as does soothing sounds. The wavelengths of light may likewise gradually change during this relaxation up period.

Optionally at 312, facility personnel, the occupant, or the environmental control system 200 or a portion thereof selects a program to execute to provide the environmental characteristics, attributes or amenities. Such may be done, for example, where no program has previously been specified or identified. Alternatively, such may be done where multiple programs are specified for a given occupant. As previously noted, the one or more programs may be stored for each perspective occupant, for example stored in a smartcard or keycard 114 or stored in a database in a nontransitory computer- or processor-readable media 246. These programs or identifiers representing these programs may be presented to the facility personnel or occupant to select from, for instance via one or more of an input device, panel or kiosk 283, 284. Alternatively, or additionally, the control subsystem 202 (FIG. 2) may select a program, for example based on certain criteria about the occupant. For instance, the control subsystem 202 (FIG. 2) may determine that the occupant has recently traveled from a location with a significantly different natural light cycle from that of the location of the habitable environment 100 (FIG. 1). Thus, the control subsystem 202 (FIG. 1) may select a program which provides specific illumination or other characteristics that alleviates or otherwise addresses symptoms or ailments associated with such changes in natural illumination due to travel, such as jet lag or SAD.

A set of patterns may be defined which accommodate changes in total amount of natural light and/or the spectral components (e.g., wavelengths) of the natural light for a large number of pairs of origination and arrival locations, where the origination location is a location from which the occupant departs (e.g., typically the occupant's home) and the arrival location is a location to which the occupant has traveled (e.g., a hotel, motel, spa). These patterns may, for example, relate each of 24 time zones (e.g., zones of longitudes) to the other 23 time zones throughout the World. These patterns may relate to various latitudes or zones of latitudes throughout the World. For instance, patterns may be established for each pair of latitude zones (e.g., 5 degree increments of latitude) north and south of the equator. Thus, each latitude zone may be related to each other latitude zone by a respective pattern. Patterns may likewise be defined for various pairs of geographical locations (e.g., longitude or time zone, and latitude) to simultaneously accommodate for both time zone changes and changes in length of solar day. Patterns do not have to be established for all possible pairs of geographic locations since most occupants will arrive from a relatively small number of geographic locations, and since the geographic location of the arrival location is presumably known for any given inhabitable environment 100 (FIG. 1). Likewise, grouping longitudes by, for instance time zone, and/or latitudes into bands (e.g., 5 degrees) will also limit the total number of stored patterns. While described as being stored, in some implementations, patterns may be generated dynamically or "on the fly" via one or more algorithms or equations using geographic locations as input.

Optionally at 314, facility personnel may check in or register one or more occupants, for use of the habitable environment 100 (FIG. 1), in a similar or identical manner as that performed at most hotels, motels, spas or hospitals. The identification of the occupant or guest at 310 and/or the selection of the program at 312 may be performed as part of this check or registration. Alternatively, identification of the occupant or guest at 310 and/or the selection of the program at 312 may be performed prior to this check in or registration 314, for example as part of booking or reserving the habitable environment 100 (FIG. 1) as an accommodation.

At 316, the control subsystem 202 (FIG. 2) runs the selected program to cause the various subsystems 202-214 to provide the environmental characteristics or amenities in the habitable environment 100 (FIG. 1).

Optionally at 318, the control subsystem 202 or a portion of the environmental control system 200 present explanatory materials which explain the operation and benefits of the habitable space including the various active and passive components. Such may include presentation of a tutorial, for instance in a video form, explaining how a user may operate or otherwise interact with the environmental control system 200.

At 320, from time-to-time the control subsystem 202 or a portion of the environmental control system 200 determines whether a change has been made to any of the operational parameters. Changes may, for example, be made by occupant(s) and/or facility personnel, or via sensed or detected conditions in the habitable environment 100 (FIG. 1). For example, the occupant(s) or facility personnel may change a setting for air temperature, relative humidity, illumination, scent dispersal, or other parameter. The change(s) may be temporary or one time changes, or may be more permanent changes that will be stored for use on another occasion or for use with another habitable environment 100 (FIG. 1). Thus, the control subsystem 202 or a portion of the environmental control system 200 may generate a new program, or execute an existing program with new or modified parameters, hence in effect constituting a new program.

If a change has been made, at 322 the control subsystem 202 or a portion of the environmental control system 200 runs the new program or program with new parameters to provide environmental characteristics. Execution of the new program causes the various subsystems 202-214 to provide the environmental characteristics or amenities in the habitable environment 100 (FIG. 1) in accordance with the new parameters.

Optionally at 324, the control subsystem 202 or a portion of the environmental control system 200 collects responses from the occupant(s) with respect to the habitable environment 100 (FIG. 1). In particular, the control subsystem 202 or a portion of the environmental control system 200 may provide an opinion survey and/or questions regarding the occupant(s) objective and/or subjective impressions of the effect of the accommodations on their overall health and/or wellness or sense of wellness. Such may also inquire regarding actual operation of the environmental control system 200, as well as the ease of use or interaction with the same. The survey or questions may provide a scale for rating the occupant's experience, and in particular sense of wellbeing.

Optionally at 326, facility personnel check out the occupant or guest. The facility personnel preferably actively inquire about the occupant's or guest's sense of wellbeing and experience with the amenities of the habitable environment 100 (FIG. 1). At this time, the facility personnel may update patterns, store new patterns, and/or delete old patterns associated with the particular occupant or guest, providing a refined experience on the occupant's next visit or use of the habitable environment 100 (FIG. 1) or other inhabitable environment 100 (FIG. 1) for instance at another location.

The high level method 300 may terminate at 328 until started again, or may continually repeat. Alternatively, the high level method 300 may run concurrently with other methods or processes.

Figure 4:
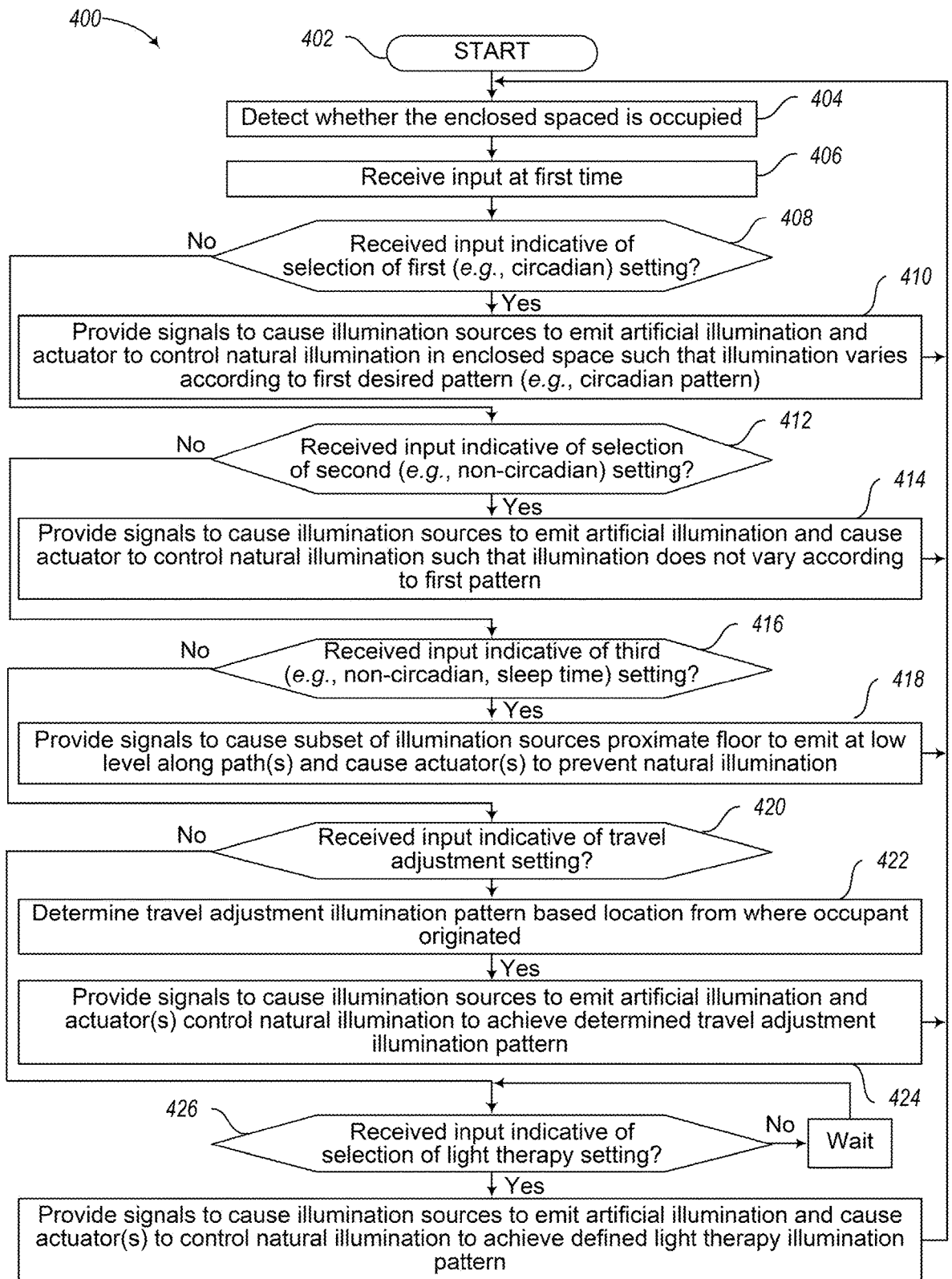
FIG. 4 is a flow diagram that shows a low level method of operating one or more components of a habitable environment enhancement system for providing illumination, according to one illustrated embodiment, which may be useful in performing at least a portion of the method illustrated in FIG. 3.

FIG. 4 shows a low level method 400 of operating one or more components of a habitable environment enhancement system for providing illumination, according to one illustrated embodiment, which may be useful in performing at least a portion of the method 300 illustrated in FIG. 3.

The low level method 400 starts at 402. The method 400 may, for example run continuously, or may start on a periodic basis, for instance every few minutes, hourly, daily, weekly, monthly. Alternatively, or additionally, the method 400, or portions thereof, may start on demand, for instance in response to detection of an occupant of the habitable environment 100, or in response to a request by a guest or operator of a facility (e.g., hotel, spa, resort, hospital).

Optionally at 404, a sensor or detector senses or detects whether the enclosed spaced is occupied. The sensor(s) may, for example, provide signals to the control subsystem indicative of whether the enclosed space is occupied. One or more of the following acts may be selectively performed based on the signals. For example, it may be more energy efficient to avoid providing active illumination when the habitable environment is not occupied.

At 406, a control subsystem receives an input, for example at a first time. The input may be indicative of any of a number of settings, for instance settings related to illumination to be provided in an enclosed space. The input may be received via at least one user actuatable input device located within the enclosed space or at an entrance to the enclosed space. Additionally or alternatively, input may be received via at least one user actuatable input device located remotely from the enclosed space. For example, located at a reception, concierge, building maintenance or other centralized location associated with the building.

At 408, the control subsystem determines whether the received input is indicative of a selection of a first setting. The first setting may, for example, be a circadian setting, that is a setting or pattern of illumination that is consistent with and establishes a natural circadian rhythm or cycle in a human. Such may, for example, mimic the intensity and chromatic makeup of natural sunlight and darkness over a solar day at some given location on the Earth.

At 410, in response to determining the first input indicates a first setting, the control subsystem provide signals to cause at least some of the illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination varies over a first period of time according to a first pattern. The first pattern may, for example be a circadian pattern (e.g., pattern consistent with and which establishes a natural circadian rhythm or cycle in a human).

At 412, the control subsystem determines whether the received input is indicative of a selection of a second setting. The second setting may be a first non-circadian setting, that is any setting or pattern of illumination other than a setting or pattern of illumination that is consistent with and establishes a natural circadian rhythm or cycle in a human.

At 414, in response to the second input the control subsystem provides signals to cause the illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination does not vary over a second period of time according to a non-circadian pattern (e.g., any pattern other than a pattern consistent with and which establishes a natural circadian rhythm or cycle in a human). For example, in response to the second input, the control subsystem may provide signals to the illumination sources and the actuator(s) such that the combination of the artificial and the natural illumination remains constant over the second period of time.

At 416, the control subsystem determines whether the received input is indicative of a selection of a second non-circadian setting that is a sleep time setting at a third time.

At 418, in response to the third input the control subsystem provides signals to cause a subset of the illumination sources proximate to a floor in the enclosed space to emit artificial illumination at a low illumination level along at least one path. The signals may further cause the at least one actuator to prevent natural illumination from being received into the enclosed space via the one or more windows.

At 420, the control subsystem determines whether the received input is indicative of a selection of a travel adjustment setting.

At 422, in response to the fourth input the control subsystem determines a travel adjustment illumination pattern based at least in part on a geographic location from where an occupant of the enclosed space originated to accommodate a change in circadian rhythm due to travel by the occupant.

At 424, also in response to the fourth input, the control subsystem provides signals to cause the illumination sources to emit artificial illumination at the levels and the wavelengths and to cause the at least one actuator to control at least the level of natural illumination received into the enclosed space via the one or more windows such that the combination of the artificial and the natural illumination achieves the determined travel adjustment illumination pattern in the enclosed space.

At 426, the control subsystem determines whether the received input is indicative of a selection of a light therapy setting at a fourth time.

At 428, in response to the fourth input indicative of the light setting, providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the defined light therapy illumination pattern in the enclosed space over a therapeutic period of time.

The method 400 may repeat as indicated by arrow 430. Alternatively, the method 400 may terminate until called again or otherwise restarted.

FIG. 5 shows a low level method 500 of operating one or more components of a habitable environment enhancement system to adjust an amount of natural light received in the habitable environment using electrochromatic panes, according to one illustrated embodiment, which may be useful in performing at least a portion of the method 400 illustrated in FIG. 4.

At 502, a control subsystem provides signals to control an actuator (e.g., voltage or current supply) drivingly coupled to the electrochromatic panes to adjust illumination passed thereby. For example, the signals may cause the drape(s)/shade(s)/curtain(s) (collectively window coverings) to move to a fully closed position which completely or substantially blocks natural light from entering the habitable environment 100 or portion thereof via the window(s). Alternatively, the signals may cause the drape(s)/shade(s)/curtain(s) to move to a fully open position which allows a maximum amount of natural light to enter the habitable environment 100 or a portion thereof via the window(s). The signals may cause the drape(s)/shade(s)/curtain(s) to move to a variety of intermediate positions between the fully closed and fully open positions, which intermediate positions allow respective amounts of natural light to enter the habitable environment 100 or a portion thereof via the window(s).

Since the intensity of natural light in the ambient environment varies throughout the day, and from day to day, control may be based at least in part to one information from one or more light sensors or detectors. The light sensors or detectors may sensor or detect natural light in the exterior ambient environment and provide the control subsystem with signals indicative of an intensity or spectral power distribution thereof. Additionally or alternatively, the light sensors or detectors may sensor or detect light in the habitable environment 100 or a portion thereof and provide the control subsystem with signals indicative of an intensity thereof.

FIG. 6 shows a low level method 600 of operating one or more components of a habitable environment enhancement system to adjust an amount of natural light received in the habitable environment using drapes or shades or curtains or other window coverings, according to one illustrated embodiment, which may be useful in performing at least a portion of the method 400 illustrated in FIG. 4.

At 602, a control subsystem provides signals to control an actuator (e.g., electrical motor, solenoid) drivingly coupled via a transmission to move drape(s)/shade(s)/curtain(s) relative to a window. For example, the signals may cause the drape(s)/shade(s)/curtain(s) to move to a fully closed position which completely or substantially blocks natural light from entering the habitable environment 100 or a portion thereof via the window(s). Alternatively, the signals may cause the drape(s)/shade(s)/curtain(s) to move to a fully open position which allows a maximum amount of natural light to enter the habitable environment 100 or a portion thereof via the window(s). The signals may cause the drape(s)/shade(s)/curtain(s) to move to a variety of intermediate positions between the fully closed and fully open positions, which intermediate positions allow respective amounts of natural light to enter the habitable environment 100 or a portion thereof via the window(s).

Since the intensity of natural light in the ambient environment varies throughout the day, and from day to day, control may be based at least in part on one information from one or more light sensors or detectors. The light sensors or detectors may sensor or detect natural light in the exterior ambient environment and provide the control subsystem with signals indicative of an intensity thereof. Additionally or alternatively, the light sensors or detectors may sensor or detect light in the habitable environment 100 or a portion thereof and provide the control subsystem with signals indicative of an intensity thereof.

Figure 7:
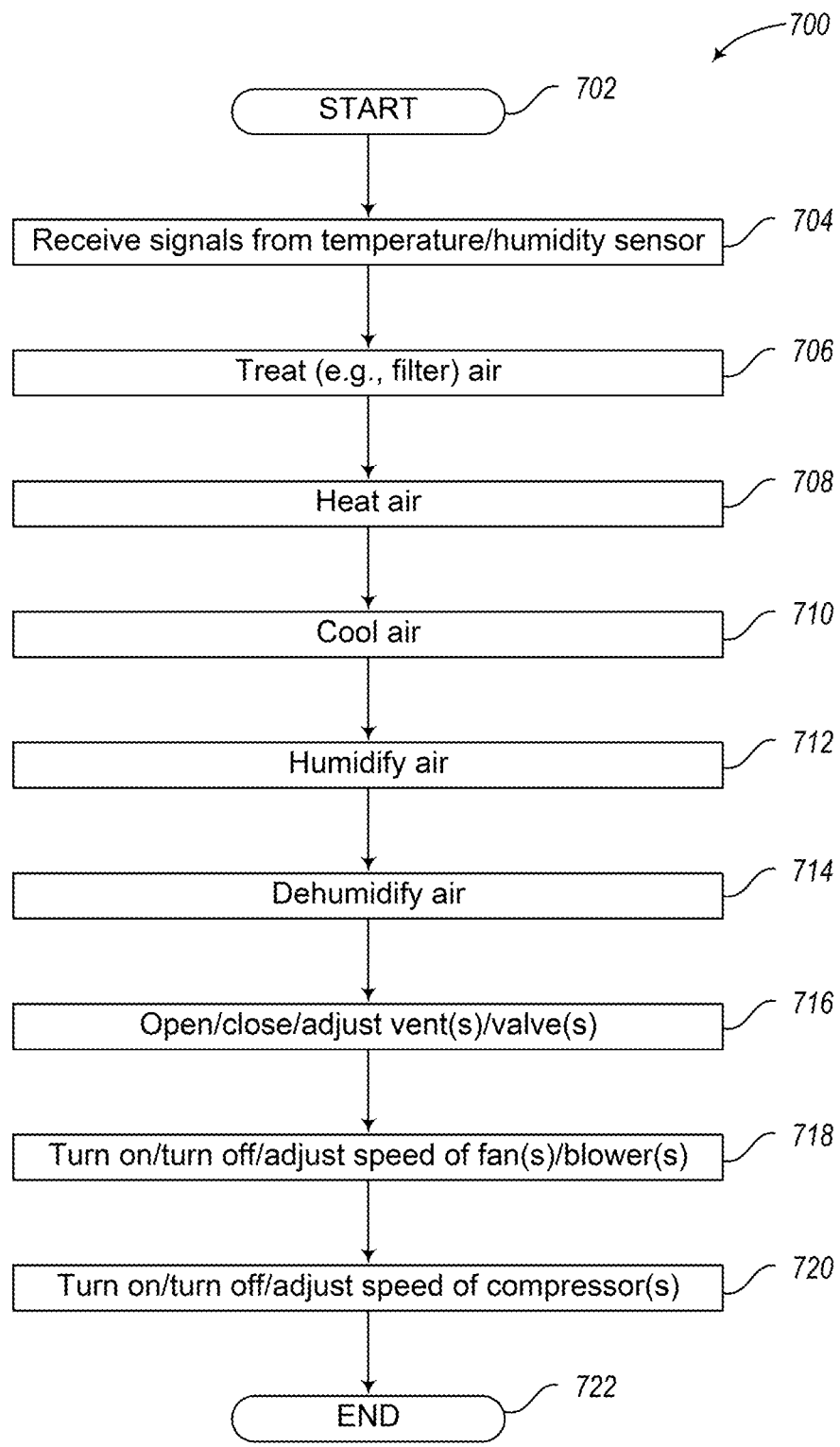
FIG. 7 is a flow diagram that shows a low level method of operating one or more components of a habitable environment enhancement system for providing heating, ventilation and cooling of a habitable environment, according to one illustrated embodiment, which may be useful in performing at least a portion of the method illustrated in FIG. 3.

FIG. 7 shows a low level method 700 of operating one or more components of a habitable environment enhancement system for providing heating, ventilation and cooling of a habitable environment 100, according to one illustrated embodiment, which may be useful in performing at least a portion of the method 300 illustrated in FIG. 3. Typically only a few of the acts identified in method 700 will be performed in any single pass. For example, cooling of air is unlikely to be performed if the air has just been heated, or dehumidifying is unlikely to be performed in humidification was just performed. Thus, method 700 provides more of a comprehensive illustration of the acts that may be performed.

The low level method 700 starts at 702. The method 700 may, for example run continuously, or may start on a periodic basis, for instance every few minutes, hourly, or daily. Alternatively, or additionally, the method 700 may start on demand, for instance in response to an adjustment of a thermostat, entry into a user input device, or sensed or detected presence of an occupant in the habitable environment 100 or a portion thereof.

At 704, the control subsystem receives signals from at least one of a temperature or humidity sensor or detector which signals are indicative of a sensed or detected temperature and/or humidity in habitable environment 100 or a portion thereof. The signals may be used in order to adjust at least one of a temperature and/or humidity of the air in the habitable environment 100, for example based at least in part on a circadian pattern over a period of time.

At 706, the control subsystem provides signals that cause air to be treated. The signals may, for example, turn ON, turn OFF, and/or adjust a speed of one or more fans or blowers. The signals may additionally or alternatively, adjust a position of a vent, damper, valve or manifold. Such may circulate or otherwise cause air to be treated by filtering via one or more mechanical (HEPA) air filters. Such may circulate or otherwise cause air to be treated by filtering via one or more electrostatic particle air filters, a voltage being supplied according to the signals. Such may circulate or otherwise cause air to be treated by exposure to ultraviolet illumination via an air ultraviolet sanitizer.

At 708, the control subsystem provides control signals which cause air to be heated. For example, the control subsystem may provide signals to a heater (e.g., forced air furnace, steam radiator) to heat air. Also for example, the control subsystem may provide signals to open, close or adjust an opening of a vent, damper, valve or manifold which routes warm air to the habitable environment 100 or a portion thereof.

At 710, the control subsystem provides control signals which cause air to be cooled. For example, the control subsystem may provide signals to a cooler (e.g., air conditioning, swamp cooler) to cool (i.e., remove heat from) the air. Also for example, the control subsystem may provide signals to open, close or adjust an opening of a vent, damper, valve or manifold which routes cool air to the habitable environment 100 or a portion thereof.

At 712, the control subsystem provides control signals which cause air to be humidified. For example, the control subsystem may provide signals to a humidifier to humidify (i.e., add moisture) to the air. Also for example, the control subsystem may provide signals to open, close or adjust an opening of a vent, damper, valve or manifold which routes humidified air to the habitable environment 100 or a portion thereof.

At 714, the control subsystem provides control signals which cause air to be dehumidified. For example, the control subsystem may provide signals to a dehumidifier to dehumidify (i.e., remove moisture) from the air. Also for example, the control subsystem may provide signals to open, close or adjust an opening of a vent, damper, valve or manifold which routes dehumidified air to the habitable environment 100 or a portion thereof.

At 716, the control subsystem opens, closes, or otherwise adjusts one or more vents or dampers or valves or manifolds. Operation of various vents, dampers, valves or manifolds may provide fresh air, conditioned air, and/or scents or aromas to the habitable environment 100 or a portion thereof. The vents or dampers or valves or manifolds may be operated via one or more actuators, for example electric motors or solenoids, or shape memory alloy actuators, spring loaded actuators and/or magnetic actuators.

At 718, the control subsystem provides control signals which cause air to be moved or circulated. For example, the control subsystem may provide signals to one or more fans or blowers to move or circulate the air. The signals may turn ON, turn OFF and/or adjust a speed of a fan or blower.

At 720, the control subsystem provides control signals which cause air to be compressed. For example, the control subsystem may provide signals to one or more compressors to compress air, for instance to remove moisture or as part of removing heat. The signals may turn ON, turn OFF, or otherwise adjust a speed of a compressor.

The low level method 700 may terminate at 722 until called again, or may continually repeat. Alternatively, the low level method 700 may run concurrently with other methods or processes, for example, as one of multiple threads on a multi-threaded processor system.

Figure 8:
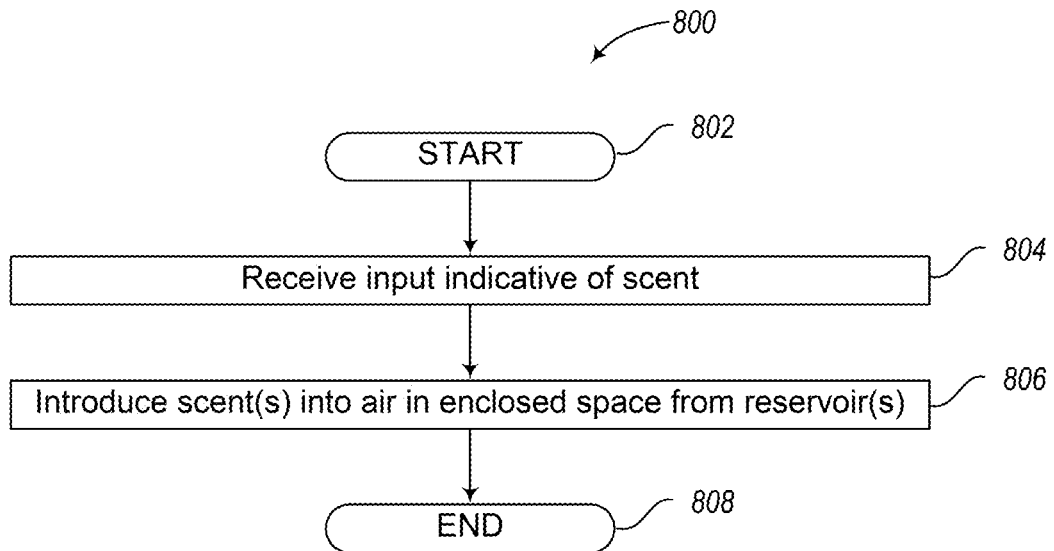
FIG. 8 is a flow diagram that shows a low level method of operating one or more components of a habitable environment enhancement system for introducing scents or aromas into a habitable environment, according to one illustrated embodiment, which may be useful in performing at least a portion of the method illustrated in FIG. 3.

FIG. 8 shows a low level method 800 of operating one or more components of a habitable environment enhancement system for introducing scents or aromas into a habitable environment, according to one illustrated embodiment, which may be useful in performing at least a portion of the method 300 illustrated in FIG. 3.

The low level method 800 starts at 802. The method 800 may, for example start on a periodic basis, for instance every few minutes, hourly, or daily. Alternatively, or additionally, the method 800 may start on demand, for instance in response to a request by a guest or operator of a facility (e.g., hotel, spa).

At 804, the control subsystem receives input indicative of a scent to be dispersed in the habitable environment 100 or a portion thereof. The input may come from an in room control panel, a remote control panel, a handheld device (e.g., smart phone, tablet computer, or personal digital assistant), or may be generated as part of execution of a program by a control subsystem.

At 806, the control subsystem provides signals which cause one or more scents to be introduced into air in the habitable environment 100 or a portion thereof. The scent(s) may be delivered from one or more reservoirs. The signals may cause a vent, damper, valve, or manifold to open, or alternatively close, allow scent to enter the habitable environment 100 or a portion thereof. The signals may additionally or alternatively cause one or more fans or blowers to cause the scent(s) to be delivered in the habitable environment 100 or a portion thereof or dispersed or circulated therein. Additionally or alternatively, the signals may cause a heater to heat scented material, for instance to vaporize the material to cause the scent to be dispersed into air which is circulated into the habitable environment 100 or a portion thereof.

The control subsystem may provide the signals to cause the scent(s) to be introduced according to or based on a defined schedule. Alternatively or additionally, the control subsystem may provide the signals to cause the scent(s) to be introduced on demand, for example in response to a user input.

The low level method 800 may terminate at 808 until called again, or may continually repeat. Alternatively, the low level method 800 may run concurrently with other methods or processes, for example, as one of multiple threads on a multi-threaded processor system.

Figure 9:
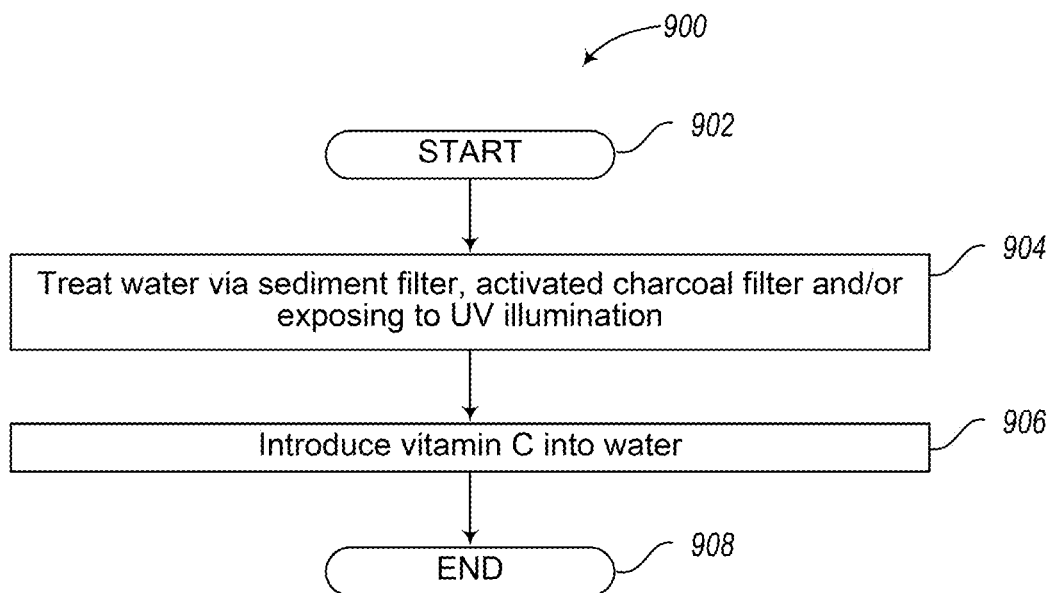
FIG. 9 is a flow diagram that shows a low level method of operating one or more components of a habitable environment enhancement system for treating water for use in a habitable environment, according to one illustrated embodiment, which may be useful in performing at least a portion of the method illustrated in FIG. 3.

FIG. 9 shows a low level method 900 of operating one or more components of a habitable environment enhancement system for treating water for use in a habitable environment, according to one illustrated embodiment, which may be useful in performing at least a portion of the method 300 illustrated in FIG. 3.

The low level method 900 starts at 902. The method 900 may, for example run continuously, or may start on a periodic basis, for instance every few minutes, hourly, or daily. Alternatively, or additionally, the method 900 may start on demand, for instance in response to use of water by an occupant of the habitable environment 100.

At 904, one or more water treatment components of a water supply subsystem treat a supply of water to a faucet or a showerhead of the habitable environment 100. Treating water may, for example include filtering water using one or more sediment or coarse particle filters. Treating water may additionally or alternatively include fine filtering of water, for example, using one or more activated charcoal filters. Treating water may additionally or alternatively include exposing the water to ultraviolet illumination of sufficient intensity and duration as to sanitize the water.

At 906, one or more water treatment components of the water supply subsystem introduce vitamin C into at least some of the water. For example, one or more valves or manifold may release vitamin C from a reservoir of vitamin C into water that is to be supplied to the showerhead of the habitable environment 100.

The low level method 900 may terminate at 908 until called again, or may continually repeat. Alternatively, the low level method 900 may run concurrently with other methods or processes, for example, as one of multiple threads on a multi-threaded processor system.

Figure 10:
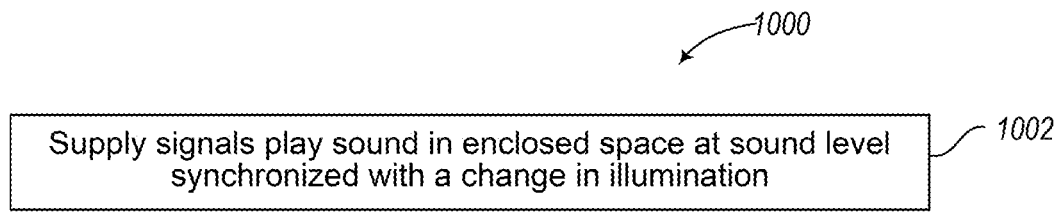
FIG. 10 is a flow diagram that shows a low level method of operating one or more components of a habitable environment enhancement system for adjusting an acoustical aspect of a habitable environment, according to one illustrated embodiment, which may be useful in performing at least a portion of the method illustrated in FIG. 3.

FIG. 10 shows a low level method 1000 of operating one or more components of a habitable environment enhancement system for adjusting an acoustical aspect of a habitable environment, according to one illustrated embodiment, which may be useful in performing at least a portion of the method 300 illustrated in FIG. 3.

The method 1000 may, for example start on a periodic basis, for instance every few minutes, hourly, or daily. Alternatively, or additionally, the method 1000 may start on demand, for instance in response to a request by a guest or operator of a facility (e.g., hotel, spa). Alternatively or additionally, the method 1000 may start in response to a call or signal from a program executed by the control subsystem, for instance in synchronization with some other aspect of the environment. For instance, sound may be triggered by an alarm clock setting, which is synchronized with light levels and/or spectrum.

In particular, the control subsystem provides signals which cause at least one speaker to play sound in the enclosed space at a sound level that changes in synchronization with a change in a level of illumination emitted by the illumination sources at 1004.

The low level method 1000 may terminate until called again, or may continually repeat. Alternatively, the method 1000 may run concurrently with other methods or processes, for example, as one of multiple threads on a multi-threaded processor system.

Modifications

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems, not necessarily the exemplary system generally described above.

The control subsystem or some other processor-based system such as a personal computer, may be programmed to evaluate a "wellness" of a given space. The system may assess various amenities provided in the environmental space, including type and effectiveness of the amenities. For instance, the system may assign points for particular types of amenities and/or effectiveness. For example, points may be assigned for having an active lighting subsystem, which additional points for active lighting can positively influence circadian patterns. Also for example, points may be assigned for air treatment, with a total number of points based on effectiveness of the air treatment. Also for example, points may be assigned for water treatment, with a total number of points based on effectiveness of the water treatment. Points may be required in each possible category (e.g., lighting, air, water, sound, reduced use of VOC leaching materials, use of sound absorbent or damping materials, use of materials that cushion or absorb shocks to protect the occupant). Alternatively, points may be required for a subset of categories. Additionally, or alternatively, a minimum number of points may be required in each of a number of categories, or a minimum cumulative score required to obtain a given rank or wellness rating. Ranks or wellness ratings may be certified and used in advertising. Wellness may be reassessed from time to time.

Wellness may be assessed based on self-reported scores or scores assigned by a reviewer or examiner. The scores may be reported via various user input devices, for instance a keyboard, keypad, touch panel associated with a GUI. The scores may, for instance, be entered via a Webpage user interface, and communicated to the system for evaluation. The system may perform comparisons of a given facility from year to year, or between different facilities. The evaluation may be compared or scored against a defined set of wellness standards in each of a number of categories or pathways.

Wellness scores need not be dependent on self-reports, but may be inferred from environmental sensors and occupant-based biometrics. For example, data gathered passively or actively from devices in the built environment, furniture or other biometric-reading devices, can contribute to a personal wellness score, that can be used to directly or indirectly control elements in the built environment including lighting, sound, HVAC or other categories previously discussed. Relevant biometrics may include any health or wellness-related measurements, including but not limited to heart rate, heart-rate variability, sleep phase, sleep length, or respiration rate, walking steps per day, body weight, or BMI.

The control system may cause a display of a dashboard which provides a concise representation of environmental information to occupants of the habitable environment 100 and/or to personnel of the facility (e.g., hotel) which houses the habitable environment 100 (e.g., room or suite). The dashboard may additionally present tips, suggestions, questionnaires, suggested settings, interventions, activities, health/wellness educational information, etc. The dashboard may be presented via a Website or Webpage and/or may be stored "in the cloud". The dashboard may be accessible via any type of processor-based device including mobile devices (e.g., smart phones, tablet computers) as a Webpage or a dedicated application. Such devices may include transducers that act based on the information and/or to control various environmental aspects of the habitable environment via the control subsystem. For example, the Webpage or application may communicatively integrate the mobile device with the lighting subsystem and/or other environmental systems and controls.

For instance, a habitable environment may include any combination of one or more of the passive or active components. Some components may reside in or be controlled as part of a different subsystem than illustrated.

Also for instance, while various methods and/or algorithms have been described, some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays or programmable logic circuits (PLCs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of nontransitory signal bearing media include, but are not limited to, the following: recordable type media such as portable disks and memory, hard disk drives, CD/DVD ROMs, digital tape, computer memory, and other non-transitory computer-readable storage media.

U.S. provisional patent application Ser. No. 61/694,125, filed Aug. 28, 2012 and U.S. patent application Ser. No. 14/012,444, filed Aug. 28, 2013 are incorporated herein by reference in their entirety. The various embodiments described above can be combined to provide further embodiments. Aspects of the embodiments can be modified, if necessary or desirable to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operation in an environmental control system which includes at least one processor, at least one nontransitory processor-readable medium communicatively coupled to the at least one processor and which stores at least one of instructions or data executable by the at least one processor, and a plurality of active subsystems operable to effect a condition in a habitable space, the method comprising:
  identifying a particular occupant present in or scheduled to occupy the habitable space;
  identifying at least one trait associated with the particular occupant;
  selecting at least one of a plurality of programs from a database based the at least one trait of the particular occupant, the programs including instructions to cause the at least one processor to automatically generate signals to control at least two of the plurality of active subsystems;
  collecting habitable space wellness data that includes at least one wellness parameter indicative of a wellness associated with the respective habitable space; and
  adjusting, by the at least one processor, an operational parameter of at least two of the active subsystems based on both the collected habitable space wellness data and the at least one selected program.

2. The method of claim 1, further comprising:
  storing the plurality of programs in a database.

3. The method of claim 1 wherein the at least one trait associated with the occupant includes one or more syndromes, aliments, or conditions for which the condition in the habitable space may be adjusted to alleviate or treat, and
  wherein the program further includes instructions to cause the at least one processor to automatically generate signals to control at least one of the plurality of active subsystems to alleviate the one or more syndromes, aliments, or conditions.

4. The method of claim 1 wherein the program specifies at least one pattern for at least one of air temperature, relative humidity, sound, or scents for different times throughout a daily cycle.

5. The method of claim 4 wherein the program specifies two or more patterns that are synchronized with one another.

6. The method of claim 1 wherein identifying the particular occupant includes entering an occupant identifier via an input device, panel, or kiosk.

7. The method of claim 1 wherein identifying the particular occupant includes reading an occupant identifier from a piece of media.

8. The method of claim 1, further comprising:
  determining whether a change has been made to an operational parameter of at least one of the active subsystems; and
  generating a new program including the changed operational parameter of the at least one of the active subsystems.

9. The method of claim 8, further comprising:
  adjusting at least one operational parameter of at least one of the active subsystems based, at least in part, on the changed operational parameter in the new program.

10. The method of claim 1 wherein collecting habitable space wellness data includes receiving, by the at least one processor, information automatically collected by at least one sensor in the respective habitable space.

11. The method of claim 1, further comprising
  collecting personal wellness data that includes, for the particular occupant, at least one wellness parameter indicative of a wellness associated with the particular occupant; and
  adjusting, by the at least one processor, the operational parameters of the at least two of the active subsystems based, in part, on the collected personal wellness data.

12. The method of claim 11, further comprising:
  determining, by the at least one processor, at least one adjustment to at least one operational parameter based on the personal wellness data.

13. The method of claim 11 wherein the personal wellness data includes occupant-based biometrics gathered from a biometric reading device.

14. The method of claim 11 wherein collecting personal wellness data includes collecting personal wellness data via at least one survey completed by the particular occupant.

15. The method of claim 1, further comprising:
  collecting personal wellness data that includes, for the particular occupant, at least one wellness parameter indicative of a wellness associated with the particular occupant; and
  updating at least one program, by the at least one processor, based on the collected personal wellness data.

16. The method of claim 15, wherein personal wellness data is collected via a survey completed by the particular occupant.

17. A method of operation in an environmental control system which includes at least one processor, at least one nontransitory processor-readable medium communicatively coupled to the at least one processor and which stores at least one of instructions or data executable by the at least one processor, and a plurality of active subsystems operable to effect a condition in a habitable space, the method comprising:
  identifying a particular occupant present in or scheduled to occupy the habitable space;
  identifying at least one trait associated with the particular occupant;
  collecting habitable space wellness data that includes at least one wellness parameter indicative of a wellness associated with the respective habitable space; and
  adjusting, by the at least one processor, an operational parameter of at least two of the active subsystems based on both the collected habitable space wellness data and the at least one identified trait associated with the particular occupant.

18. The method of claim 17, further comprising:
  collecting personal wellness data that includes, for the particular occupant, at least one wellness parameter indicative of a wellness associated with the respective individual; and
  adjusting, by the at least one processor, the operational parameters of the at least two of the active subsystems based, in part, on the collected personal wellness data.

19. The method of claim 17 wherein the operational parameters of the at least two active subsystems include one or more of air temperature, relative humidity, sound, scent, light intensity, amount of natural light, and spectral components of light.

20. A method of operation in an environmental control system which includes at least one processor, at least one nontransitory processor-readable medium communicatively coupled to the at least one processor and which stores at least one of instructions or data executable by the at least one processor, and a plurality of active subsystems operable to effect a condition in a habitable space, the method comprising:
  identifying a particular occupant present in or scheduled to occupy the habitable space;

identifying at least one trait associated with the particular occupant;

selecting at least one operational parameter for at least two of the plurality of active subsystems based the at least one trait of the particular occupant;

collecting habitable space wellness data that includes at least one wellness parameter indicative of a wellness associated with the respective habitable space; and adjusting, by the at least one processor, at least one operational parameter of the at least two of the active subsystems based on both the collected habitable space wellness data and the selected operational parameters.

21. The method of claim 20 wherein identifying the particular occupant present in or scheduled to occupy the habitable space includes reading an occupant identifier from a piece of media.

22. The method of claim 20 further comprising:

associating the at least one trait associated with the particular occupant with an occupant identifier;

storing the at least one trait and the occupant identifier in an occupant database; and wherein the processor identifies the at least one trait associated with the particular occupant by reading the occupant identifier from a piece of media and selecting the at least one trait associated with the occupant identifier from the occupant database.

\* \* \* \* \*